(12) United States Patent
Kobayashi et al.

(10) Patent No.: US 9,499,744 B2
(45) Date of Patent: *Nov. 22, 2016

(54) DIHYDROPYRAN COMPOUND, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Takahiro Kobayashi, Ichihara (JP); Takahiro Kubo, Ichihara (JP); Yasuyuki Sasada, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/737,223

(22) Filed: Jun. 11, 2015

(65) Prior Publication Data

US 2015/0361344 A1 Dec. 17, 2015

(30) Foreign Application Priority Data

Jun. 13, 2014 (JP) .................. 2014-122225

(51) Int. Cl.
C09K 19/40 (2006.01)
C09K 19/34 (2006.01)
C07D 309/22 (2006.01)
C07D 309/18 (2006.01)
C09K 19/32 (2006.01)

(52) U.S. Cl.
CPC ......... *C09K 19/3402* (2013.01); *C07D 309/18* (2013.01); *C07D 309/22* (2013.01); *C09K 19/32* (2013.01); *C09K 19/3447* (2013.01); *C09K 19/3455* (2013.01); *C09K 19/3458* (2013.01); *C09K 19/406* (2013.01); *C09K 2019/3422* (2013.01); *C09K 2019/3425* (2013.01)

(58) Field of Classification Search
CPC .................................................. C07D 493/08
See application file for complete search history.

(56) References Cited

U.S. PATENT DOCUMENTS

2011/0297881 A1 12/2011 Hirata et al.
2015/0252264 A1* 9/2015 Goto .................. C09K 19/3402
252/299.61

FOREIGN PATENT DOCUMENTS

WO 2010-095506 A 8/2010

* cited by examiner

*Primary Examiner* — Chanceity Robinson
(74) *Attorney, Agent, or Firm* — Hogan Lovells US LLP

(57) ABSTRACT

A liquid crystal compound is provided that satisfies at least one physical property, including high stability to ultraviolet light and heat, a high clearing point, low minimum temperature of a liquid crystal phase, small viscosity, suitable optical anisotropy, large dielectric anisotropy and excellent compatibility with other liquid crystal compounds. A liquid crystal composition containing the compound, and a liquid crystal display device including the composition is also provided. The composition contains the compound, and the liquid-crystal display device includes the composition:

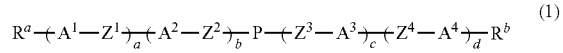

wherein, for example, $R^a$ and $R^b$ are alkyl; rings $A^1$, $A^2$, $A^3$ and $A^4$ are 1,4-cyclohexylene or 1,4-phenylene; and P is a divalent group represented by formula (pr-1) or (pr-2):

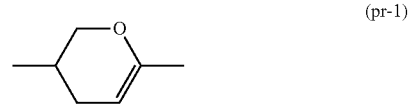

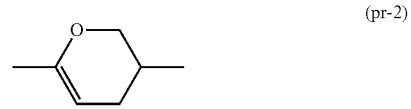

wherein, for example, $Z^1$, $Z^2$, $Z^3$ and $Z^4$ are a single bond or alkylene; and a, b, c and d are 0, 1 or 2, and a sum of a, b, c and d is 5 or less.

17 Claims, No Drawings

DIHYDROPYRAN COMPOUND, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a dihydropyran compound, a liquid crystal composition containing the compound, and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field induced photo-reactive alignment (FPA) mode. A classification based on a driving mode in the device includes a passive matrix (PM) and an active matrix (AM). The PM is classified into static and multiplex and so forth. The AM is classified into a thin film transistor (TFT), a metal insulator metal (MIM) and so forth.

A liquid crystal composition is sealed into the device. Physical properties required for the composition are different depending on the modes. Specific examples of the physical properties include stability to ultraviolet light and heat, a temperature range of a nematic phase, viscosity, optical anisotropy, dielectric anisotropy, specific resistance and an elastic constant. The composition is prepared by mixing many liquid crystal compounds. The physical properties required for the compound include a high stability to an environment such as water, air, heat and light, a wide temperature range of a liquid crystal phase, a small viscosity, a suitable optical anisotropy, a large (or small) dielectric anisotropy and a good compatibility with other compounds. The compound having a high maximum temperature of the nematic phase is preferred. The compound having a low minimum temperature in the liquid crystal phase such as the nematic phase and a smectic phase is preferred. The compound having the small viscosity contributes to the device having a short response time. A suitable value of optical anisotropy is different depending on a device mode. The compound having a large positive (or large negative) dielectric anisotropy is preferred for driving the device at low voltage. The compound having a small dielectric anisotropy is suitable for adjusting the viscosity or the like. The compound having a good compatibility with other compounds is preferred for preparing the composition. The device may be occasionally used at a temperature below a freezing point, and therefore the compound having a good compatibility at a low temperature is preferred.

A variety of liquid crystal compounds have so far been prepared. Development of a new liquid crystal compound has been so far continued because excellent characteristics that are not found in a conventional compound are expected. The reason is that a suitable balance between two of the characteristics required upon preparing the liquid crystal composition is expected for a new compound. Only limited examples of reports exist on a compound having a divalent group described below.

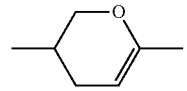
(pr-1)

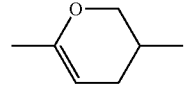
(pr-2)

Tetrahydropyran compound (R-1) below is disclosed in TABLE 2 of MOL. Cryst. Liq. Cryst., Vol. 494, pp. 58-67, 2008.

Dihydropyran compound (No. 160) in the invention has a larger negative dielectric anisotropy and a higher maximum temperature of the liquid crystal phase, and is superior in the characteristics in comparison with compound (R-1).

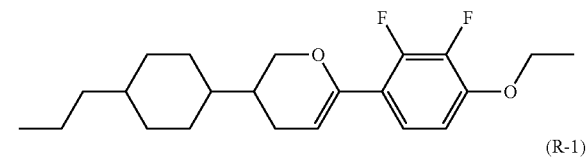
(No. 160)

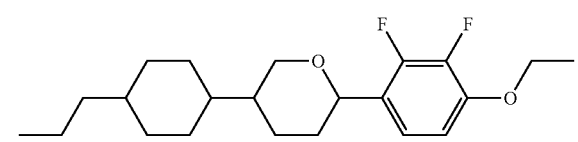
(R-1)

CITATION LIST

Patent Literature

Patent literature No. 1: WO 2010/095506 A.

SUMMARY OF INVENTION

Technical Problem

A first object of the invention is to provide a liquid crystal composition satisfying at least one of physical properties such as a high stability to an environment, a high clearing point, a low minimum temperature of a liquid crystal phase, a small viscosity, a suitable optical anisotropy, a large dielectric anisotropy (or small dielectric anisotropy) and an excellent compatibility with other liquid crystal compounds. A second object is to provide a liquid crystal composition containing the compound and satisfying at least one of physical properties such as a high stability to ultraviolet light and heat, a high maximum temperature of a nematic phase, a low minimum temperature of the nematic phase, a small viscosity, a suitable optical anisotropy, a large dielectric anisotropy, a large specific resistance and a suitable elastic constant. The object is to provide a liquid crystal composition having a suitable balance regarding at least two of the physical properties. A third object is to provide a liquid crystal display device that includes the composition and has a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition:

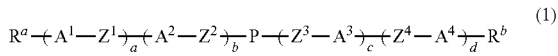 (1)

wherein, in formula (1), $R^a$ and $R^b$ are independently alkyl having 1 to 10 carbons, and in the alkyl, at least one of —$CH_2$— may be replaced by —O—, —S—, —CO— or —$SiH_2$—, and at least one of —$CH_2CH_2$— may be replaced by —CH=CH— or —C≡C—;

ring $A^1$, $A^2$, $A^3$ and $A^4$ are independently 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one of —$CH_2$— may be replaced by —O—, —S—, —CO— or —$SiH_2$—, at least one of —$CH_2CH_2$— may be replaced by —CH=CH— or —CH=N—, and in the divalent groups, at least one of hydrogen may be replaced by fluorine, chlorine, —C≡N, —$CF_2$, —$CHF_2$, —$CH_2F$, —$OCF_3$, —$OCHF_2$ or —$OCH_2F$; and P is a divalent group represented by formula (pr-1) or (pr-2):

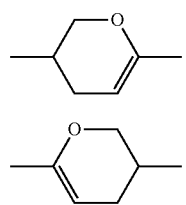

wherein, $Z^1$, $Z^2$, $Z^3$ and $Z^4$ are independently a single bond or alkylene having 1 to 6 carbons, and in the alkylene, at least one of —$CH_2$— may be replaced by —O—, —S—, —CO— or —$SiH_2$—, one or two of —$CH_2CH_2$— may be replaced by —CH=CH— or —C≡C—, and in the divalent groups, at least one of hydrogen may be replaced by fluorine or chlorine;

a, b, c and d are independently 0, 1 or 2, and a sum of a, b, c and d is 5 or less;

however, when P is represented by formula (pr-1), $R^a$ is alkyl, $R^b$ is alkoxy, a is 1, b is 0, c and d are 1, $A^1$ is cyclohexylene, $A^3$ and $A^4$ are 2,3-difluorophenylene, $Z^1$ and $Z^4$ are a single bond and $Z^3$ is alkylene having 2 carbons, in the alkylene, at least one of —$CH_2$— is replaced by —O—, —S—, —CO— or —$SiH_2$—, or one of —$CH_2CH_2$— is replaced by —CH=CH— or —C≡C—, and in the divalent groups, at least one of hydrogen is replaced by fluorine or chlorine;

moreover, when P is represented by formula (pr-2), $R^a$ is alkoxy, $R^b$ is alkyl, a and b are 1, c is 1, d is 0, $A^1$ and $A^2$ are 2,3-difluorophenylene, $A^3$ is cyclohexylene, $Z^1$ and $Z^3$ are a single bond and $Z^2$ is alkylene having 2 carbons, in the alkylene, at least one of —$CH_2$— is replaced by —O—, —S—, —CO— or —$SiH_2$—, or one of —$CH_2CH_2$— is replaced by —CH=CH— or —C≡C—, and in the divalent groups, at least one of hydrogen is replaced by fluorine or chlorine.

The invention also concerns use of the liquid crystal composition in a liquid crystal display device.

The invention further concerns use of the liquid crystal composition in a polymer sustained alignment mode liquid crystal display device.

Advantageous Effects of Invention

A first advantage of the invention is to provide a liquid crystal compound satisfying at least one of physical properties such as a high stability to an environment, a high clearing point, a low minimum temperature of a liquid crystal phase, a small viscosity, a suitable optical anisotropy and a large dielectric anisotropy (or small dielectric anisotropy), and an excellent compatibility with other liquid crystal compounds. A second advantage of the invention is to provide a liquid crystal composition containing the compound and satisfying at least one of physical properties such as a high stability to ultraviolet light and heat, a high maximum temperature of a nematic phase, a low minimum temperature of the nematic phase, a small viscosity, a suitable optical anisotropy, a large dielectric anisotropy, a large specific resistance and a suitable elastic constant. The advantage is to provide a liquid crystal composition having a suitable balance regarding at least two of the physical properties. A third advantage of the invention is to provide a liquid crystal display device that includes the composition and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase or a smectic phase, and also a compound having no liquid crystal phase but being added for adjusting physical properties such as a maximum temperature, a minimum temperature, viscosity and dielectric anisotropy. The liquid crystal compound, a liquid crystal composition and a liquid crystal display device may be occasionally abbreviated as "compound," "composition" and "device," respectively. The liquid crystal display device is a generic term for a liquid crystal display panel and a liquid crystal display module. A clearing point is a transition temperature between the liquid crystal phase and an isotropic phase in the liquid crystal compound. The minimum temperature of the liquid crystal phase is a transition temperature between a solid and the liquid crystal phase (the smectic phase, the nematic phase or the like) in the liquid crystal compound. A higher limit of a temperature range of the nematic phase is a transition temperature between the nematic phase and the isotropic phase in the liquid crystal composition, and may be occasionally abbreviated as the maximum temperature. A lower limit of the temperature range of the nematic phase may be occasionally abbreviated as the minimum temperature.

A compound represented by formula (1) may be occasionally abbreviated as "compound (1)." The abbreviation may also apply occasionally to a compound represented by formula (2) or the like. In formulas (2) to (15), a symbol $B^1$, $C^1$ or the like surrounded by a hexagonal shape corresponds to ring $B^1$, ring $C^1$ or the like, respectively. A plurality of $R^a$ are described in different formulas. In the compounds, two groups represented by two of arbitrary $R^a$ may be identical or different. In one case, for example, $R^a$ of compound (1-1) is ethyl and $R^a$ of compound (1-2) is ethyl. In another case, $R^a$ of compound (1-1) is ethyl and $R^a$ of compound (1-2) is propyl. A same rule applies also to a symbol such as $R^b$, $A^1$ and $Z^1$. In formula (8), when i is 2, two of ring $D^1$ exist. In the compound, two groups represented by two of ring $D^1$ may be identical or different. A same rule applies also to two of arbitrary ring $D^1$ when n is larger than 2. A same rule further applies to a symbol of any other ring, a bonding group or the like.

The liquid crystal compound has a six-membered ring such as 1,4-cyclohexylene and 1,4-phenylene, and rod-like molecular structure. The liquid crystal composition is prepared by mixing such liquid crystal compounds. A ratio (content) of the liquid crystal compound is expressed in terms of weight percent (% by weight) based on the weight of the liquid crystal composition. An additive such as an optically active compound, an antioxidant, an ultraviolet light absorber, a light stabilizer, a heat stabilizer, an antifoaming agent, a polymerization initiator and a polymerization inhibitor is added to the liquid crystal composition, when necessary. A ratio (content) of the additive is expressed in terms of weight percent (% by weight) based on the weight of the liquid crystal composition in a manner similar to the ratio of the liquid crystal compound. Weight parts per million (ppm) may be occasionally used. However, a ratio of the polymerization initiator and the polymerization inhibitor is expressed based on the weight of the polymerizable compound.

An expression "at least one of "A" may be replaced by "B"" means that a position of "A" when the number of "A" is 1 is arbitrary, and that the positions can be freely selected without restriction when the number of "A" is 2 or more. An expression "at least one of A may be replaced by B, C or D" means inclusion of a case where at least one of A is replaced by B, a case where at least one of A is replaced by C, and a case where at least one of A is replaced by D, and also a case where a plurality of A are replaced by at least two of B, C and D. For example, alkyl in which at least one of —CH$_2$— (or —CH$_2$CH$_2$—) may be replaced by —O— (or —CH=CH—) includes alkyl, alkenyl, alkoxy, alkoxyalkyl, alkoxyalkenyl and alkenyloxyalkyl. In addition, a case where replacement of two consecutive —CH$_2$— by —O— results in forming-O—O— is not preferred. In the alkyl or the like, a case where replacement of —CH$_2$— of a methyl part (—CH$_2$—H) by —O— results in forming —O—H is not preferred, either.

Then, 2-fluoro-1,4-phenylene means two divalent rings described below. In a chemical formula, fluorine may be leftward (L) or rightward (R). A same rule applies also to an asymmetrical divalent group derived from a ring, such as tetrahydropyran-2,5-diyl.

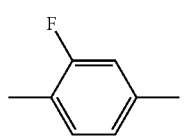

(L)

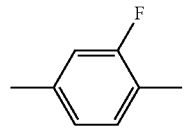

(R)

The invention includes a content described in items as described below.

Item 1. A compound represented by formula (1):

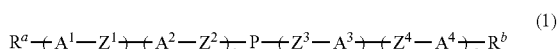

(1)

wherein, in formula (1), $R^a$ and $R^b$ are independently alkyl having 1 to 10 carbons, and in the alkyl, at least one of —CH$_2$— may be replaced by —O—, —S—, —CO— or —SiH$_2$—, and at least one of —CH$_2$CH$_2$— may be replaced by —CH=CH— or —C≡C—;

ring $A^1$, $A^2$, $A^3$ and $A^4$ are independently 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one of —CH$_2$— may be replaced by —O—, —S—, —CO— or —SiH$_2$—, at least one of —CH$_2$CH$_2$— may be replaced by —CH=CH— or —CH=N—, and in the divalent groups, at least one of hydrogen may be replaced by fluorine, chlorine, —C≡N, —CF$_3$, —CHF$_2$, —CH$_2$F, —OCF$_3$, —OCHF$_2$ or —OCH$_2$F; and P is a divalent group represented by formula (pr-1) or (pr-2):

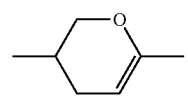

(pr-1)

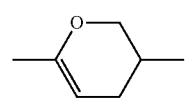

(pr-2)

wherein, $Z^1$, $Z^2$, $Z^3$ and $Z^4$ are independently a single bond or alkylene having 1 to 6 carbons, and in the alkylene, at least one of —CH$_2$— may be replaced by —O—, —S—, —CO— or —SiH$_2$—, one or two of —CH$_2$CH$_2$— may be replaced by —CH=CH— or —C≡C—, and in the divalent groups, at least one of hydrogen may be replaced by fluorine or chlorine;

a, b, c and d are independently 0, 1 or 2, and a sum of a, b, c and d is 5 or less;

however, when P is represented by formula (pr-1), $R^a$ is alkyl, $R^b$ is alkoxy, a is 1, b is 0, c and d are 1, $A^1$ is cyclohexylene, $A^3$ and $A^4$ are 2,3-difluorophenylene, $Z^1$ and $Z^4$ are a single bond and $Z^3$ is alkylene having 2 carbons, in the alkylene, at least one of —CH$_2$— is replaced by —O—, —S—, —CO— or —SiH$_2$—, or one of —CH$_2$CH$_2$— is replaced by —CH=CH— or —C≡C—, and in the divalent groups, at least one of hydrogen is replaced by fluorine or chlorine;

moreover, when P is represented by formula (pr-2), $R^a$ is alkoxy, $R^b$ is alkyl, a and b are 1, c is 1, d is 0, $A^1$ and $A^2$ are 2,3-difluorophenylene, $A^3$ is cyclohexylene, $Z^1$ and $Z^3$ are a single bond and $Z^2$ is alkylene having 2 carbons, in the alkylene, at least one of —$CH_2$— is replaced by —O—, —S—, —CO— or —$SiH_2$—, or one of —$CH_2CH_2$— is replaced by —CH=CH— or —C≡C—, and in the divalent groups, at least one of hydrogen is replaced by fluorine or chlorine.

Item 2. The compound according to item 1, represented by formulas (1-1) to (1-3):

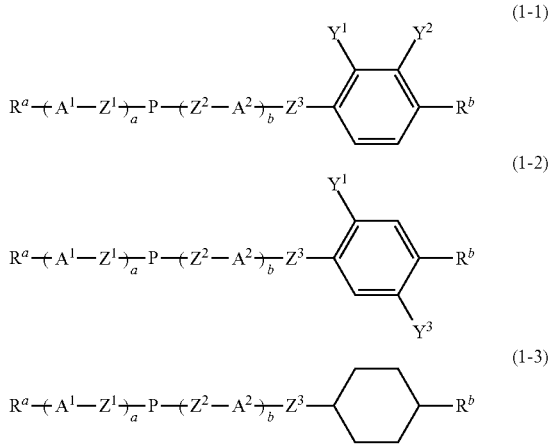

(1-1)

(1-2)

(1-3)

wherein, in formulas (1-1) to (1-3), $R^a$ and $R^b$ are independently hydrogen or alkyl having 1 to 10 carbons, and in the alkyl, at least one of —$CH_2$— may be replaced by —O— or —S—, at least one of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, tetrahydro-2H-pyran-2-one-3,6-diyl, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene, 2,3-dichloro-1,4-phenylene, pyridine-2,5-diyl, pyrimidine-2,5-diyl, or naphthalene-2,6-diyl, and in the divalent groups, at least one of hydrogen may be replaced by fluorine, chlorine, —$CF_3$, —$CHF_2$, —$CH_2F$, —$OCF_3$, —$OCHF_2$ or —$OCH_2F$; and P is a divalent group represented by formula (pr-1) or (pr-2):

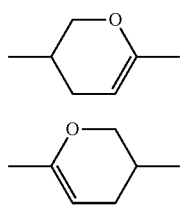

(pr-1)

(pr-2)

wherein, $Z^1$, $Z^2$ and $Z^3$ are independently a single bond, —COO—, —OCO—, —$CH_2O$—, —$OCH_2$—, —$CF_2O$—, —$OCF_2$—, —$CH_2CH_2$—, —CH=CH—, —CF=CH—, —CH=CF—, —CF=CF—, —C≡C—, —$CH_2CO$—, —$COCH_2$—, —$CH_2SiH_2$—, —$SiH_2CH_2$—, —$(CH_2)_4$—, —$(CH_2)_2COO$—, —$(CH_2)_2OCO$—, —$OCO(CH_2)_2$—, —$COO(CH_2)_2$—, —$(CH_2)_2CF_2O$—, —$(CH_2)_2OCF_2$—, —$OCF_2(CH_2)_2$—, —$CF_2O(CH_2)_2$—, —$(CH_2)_3O$— or —$O(CH_2)_3$—;

$Y^1$, $Y^2$ and $Y^3$ are independently hydrogen, fluorine, chlorine, —$CF_3$, —$CHF_2$, —$CH_2F$, —$OCF_3$, —$OCHF_2$ or —$OCH_2F$; and a and b are independently 0, 1, 2 or 3, and a sum of a and b is 4 or less; and in formula (1-1), when $R^a$ is alkyl, $R^b$ is alkoxy, a and b are 1, $A^1$ is cyclohexylene, $A^2$ is 2,3-difluorophenylene, $Z^1$ and $Z^3$ are a single bond, $Z^2$ is —$CH_2CH_2$— and $Y^1$ and $Y^2$ are fluorine, P is a divalent group represented by formula (pr-2).

Item 3. The compound according to item 1 or 2, represented by any one of formulas (1-11a) to (1-13a) and formulas (1-11b) to (1-13b):

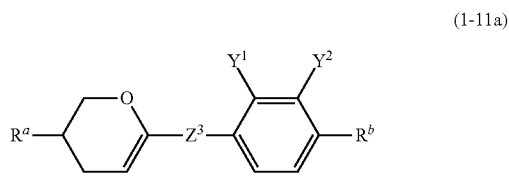

(1-11a)

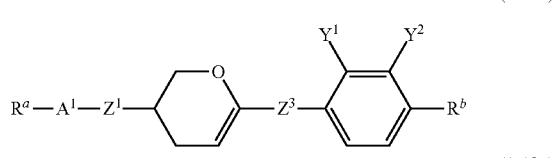

(1-12a)

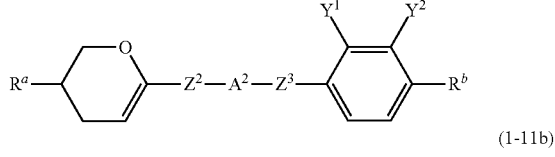

(1-13a)

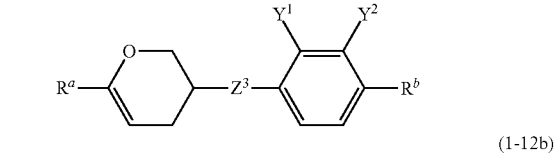

(1-11b)

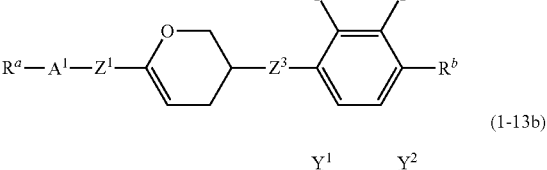

(1-12b)

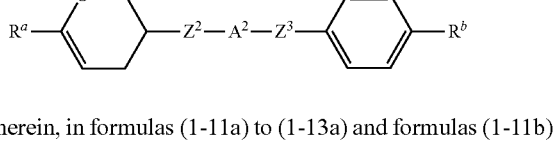

(1-13b)

wherein, in formulas (1-11a) to (1-13a) and formulas (1-11b) to (1-13b), $R^a$ and $R^b$ are independently alkyl having 1 to 10 carbons, and in the alkyl, one or two of —$CH_2$— may be replaced by —O— or —S—, and one or two of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene, pyridine-2,5-diyl, pyrimidine-2,5-diyl or naphthalene-2,6-diyl;

$Z^1$, $Z^2$ and $Z^3$ are independently a single bond, —CH$_2$CH$_2$—, —COO—, —OCO—, —CH$_2$O—, —OCH$_2$—, —CF$_2$O—, —OCF$_2$—, —CH=CH—, —CF=CH—, —CH=CF—, —CF=CF—, —C≡C—, —(CH$_2$)$_4$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—; and $Y^1$ and $Y^2$ are independently fluorine or chlorine.

Item 4. The compound according to item 3, wherein, in formulas (1-11a) to (1-13a) and formulas (1-11b) to (1-13b), $R^a$ and $R^b$ are independently alkyl having 1 to 10 carbons, alkenyl having 2 to 10 carbons or alkoxy having 1 to 9 carbons;

ring $A^1$ and $A^2$ are independently 1,4-cyclohexylene, tetrahydropyran-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene or pyrimidine-2,5-diyl;

$Z^1$, $Z^2$ and $Z^3$ are independently a single bond, —CH$_2$CH$_2$—, —COO—, —OCO—, —CH$_2$O—, —OCH$_2$—, —CF$_2$O—, —OCF$_2$—, —CH=CH—, —CF=CF—, —C≡C— or —(CH$_2$)$_4$—; and $Y^1$ and $Y^2$ are independently fluorine or chlorine.

Item 5. The compound according to item 1 or 2, represented by any one of formulas (1-21a) to (1-23a) and formulas (1-21b) to (1-23b):

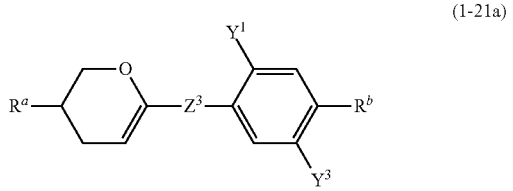

(1-21a)

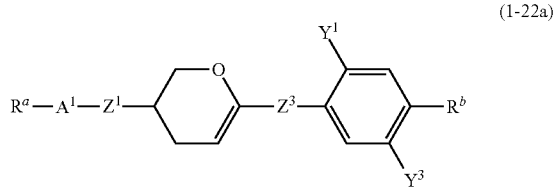

(1-22a)

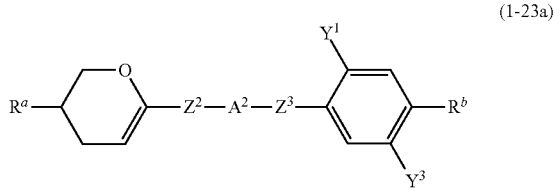

(1-23a)

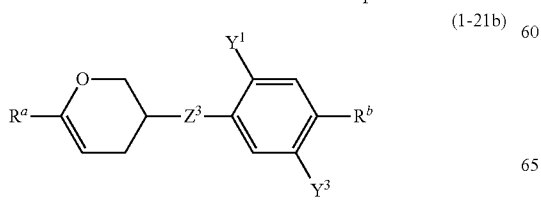

(1-21b)

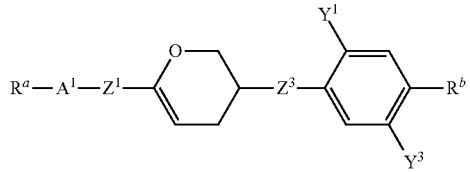

(1-22b)

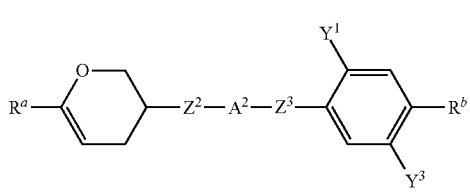

(1-23b)

wherein, in formulas (1-21a) to (1-23a) and formulas (1-21b) to (1-23b), $R^a$ and $R^b$ are independently alkyl having 1 to 10 carbons, and in the alkyl, one or two of —CH$_2$— may be replaced by —O— or —S—, and one or two of —CH$_2$CH$_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, pyridine-2,5-diyl, pyrimidine-2,5-diyl or naphthalene-2,6-diyl;

$Z^1$, $Z^2$ and $Z^3$ are independently a single bond, —CH$_2$CH$_2$—, —COO—, —OCO—, —CH$_2$O—, —OCH$_2$—, —CF$_2$O—, —OCF$_2$—, —CH=CH—, —CF=CH—, —CH=CF—, —CF=CF—, —C≡C—, —(CH$_2$)$_4$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—; and $Y^1$ and $Y^3$ are independently hydrogen, fluorine or chlorine.

Item 6. The compound according to item 5, wherein, in formulas (1-21a) to (1-23a) and formulas (1-21b) to (1-23b), $R^a$ and $R^b$ are independently alkyl having 1 to 10 carbons, alkenyl having 2 to 10 carbons or alkoxy having 1 to 9 carbons;

rings $A^1$ and $A^2$ are independently 1,4-cyclohexylene, tetrahydropyran-2,5-diyl, 1,4-phenylene, 2-fluoro-1,4-phenylene, 2,5-difluoro-1,4-phenylene, 2,6-difluoro-1,4-phenylene, 2-chloro-1,4-phenylene or pyrimidine-2,5-diyl;

$Z^1$, $Z^2$ and $Z^3$ are independently a single bond, —CH$_2$CH$_2$—, —COO—, —OCO—, —CH$_2$O—, —OCH$_2$—, —CF$_2$O—, —OCF$_2$—, —CH=CH—, —CF=CF—, —C≡C— or —(CH$_2$)$_4$—; and $Y^1$ and $Y^3$ are independently hydrogen or fluorine.

Item 7. The compound according to item 1 or 2, represented by any one of formulas (1-31) to (1-36):

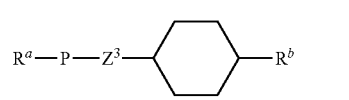

(1-31)

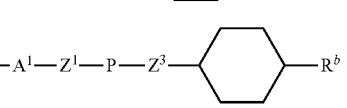

(1-32)

-continued

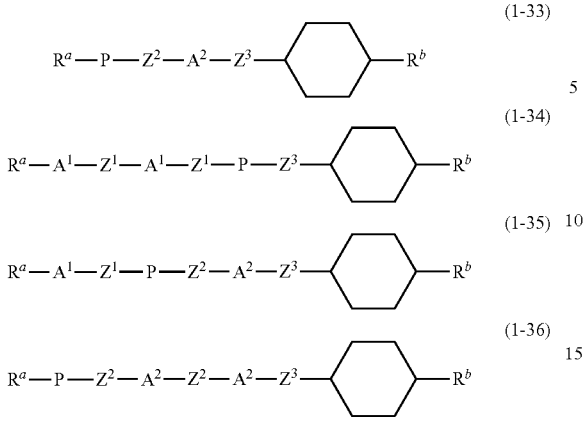

(1-33)
(1-34)
(1-35)
(1-36)

wherein, in formulas (1-31) to (1-36), $R^a$ and $R^b$ are independently alkyl having 1 to 10 carbons, and in the alkyl, one or two of —$CH_2$— may be replaced by —O— or —S—, and one or two of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene, pyridine-2,5-diyl, pyrimidine-2,5-diyl or naphthalene-2,6-diyl; and P is a divalent group represented by formula (pr-1) or (pr-2):

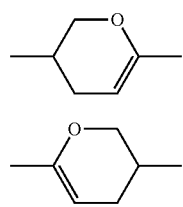

(pr-1)

(pr-2)

wherein, $Z^1$, $Z^2$ and $Z^3$ are independently a single bond, —$CH_2CH_2$—, —COO—, —OCO—, —$CH_2O$—, —$OCH_2$—, —$CF_2O$—, —$OCF_2$—, —CH=CH—, —CF=CH—, —CH=CF—, —CF=CF—, —C≡C—, —$(CH_2)_4$—, —$(CH_2)_2COO$—, —$OCO(CH_2)_2$—, —$(CH_2)_2CF_2O$—, —$OCF_2(CH_2)_2$—, —$(CH_2)_3O$— or —$O(CH_2)_3$—.

Item 8. The compound according to item 1 or 2, represented by any one of formulas (1-14) to (1-16) and formulas (1-24) to (1-26):

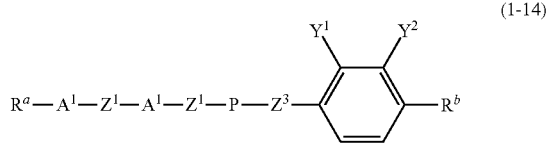

(1-14)

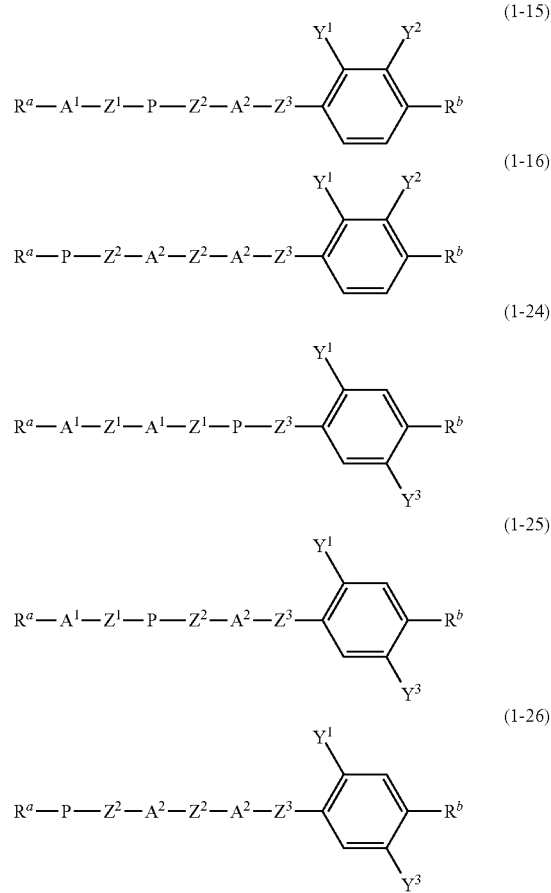

(1-15)
(1-16)
(1-24)
(1-25)
(1-26)

wherein, in formulas (1-14) to (1-16) and formulas (1-24) to (1-26), $R^a$ and $R^b$ are independently alkyl having 1 to 10 carbons, and in the alkyl, one or two of —$CH_2$— may be replaced by —O— or —S—, and one or two of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, pyridine-2,5-diyl, pyrimidine-2,5-diyl or naphthalene-2,6-diyl; and P is a divalent group represented by formula (pr-1) or (pr-2):

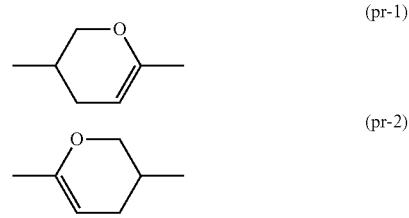

(pr-1)

(pr-2)

wherein, $Z^1$, $Z^2$ and $Z^3$ are independently a single bond, —$CH_2CH_2$—, —COO—, —OCO—, —$CH_2O$—, —$OCH_2$—, —$CF_2O$—, —$OCF_2$—, —CH=CH—, —CF=CH—, —CH=CF—, —CF=CF—, —C≡C—, —(CH$_2$)$_4$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—; and in formulas (1-14) to (1-16), Y$^1$ and Y$^2$ are independently fluorine or chlorine, and in formulas (1-24) to (1-26), Y$^1$ and Y$^3$ are independently hydrogen, fluorine or chlorine.

Item 9. The compound according to item 8, wherein, in formulas (1-14) to (1-16) and formulas (1-24) to (1-26) according to item 8, R$^a$ and R$^b$ are independently alkyl having 1 to 10 carbons, alkenyl having 2 to 10 carbons or alkoxy having 1 to 9 carbons;

ring A$^1$ and A$^2$ are independently 1,4-cyclohexylene, tetrahydropyran-2,5-diyl, 1,4-phenylene, 2-fluoro-1,4-phenylene, 2,5-difluoro-1,4-phenylene, 2,6-difluoro-1,4-phenylene, 2-chloro-1,4-phenylene or pyrimidine-2,5-diyl;

Z$^1$, Z$^2$ and Z$^3$ are independently a single bond, —CH$_2$CH$_2$—, —COO—, —OCO—, —CH$_2$O—, —OCH$_2$—, —CF$_2$O—, —OCF$_2$—, —CH=CH—, —CF=CF—, —C≡C— or —(CH$_2$)$_4$—; and Y$^1$ and Y$^2$ are independently hydrogen or fluorine.

Item 10. The compound according to any one of items 1, 2, 3 and 4, represented by any one of formula (1-111a), formula (1-121a), formula (1-131a), formula (1-141a), formula (1-151a), formula (1-161a), formula (1-111b), formula (1-121b), formula (1-131b), formula (1-141b), formula (1-151b) and formula (1-161b):

(1-111a)

(1-111b)

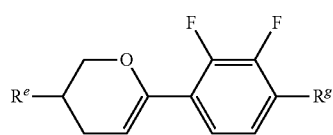
(1-121a)

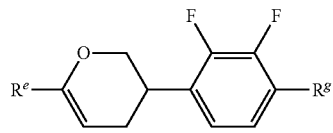
(1-121b)

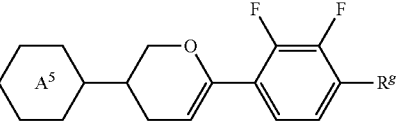
(1-131a)

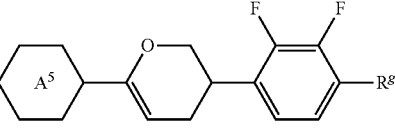
(1-131b)

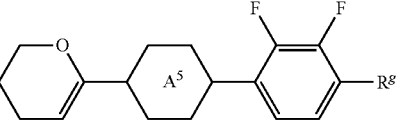
(1-141a)

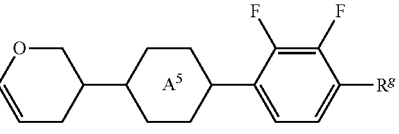
(1-141b)

-continued

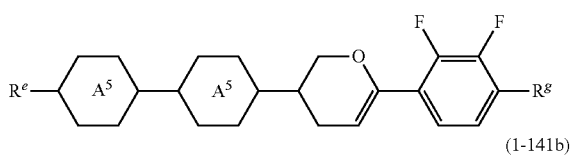
(1-141b)

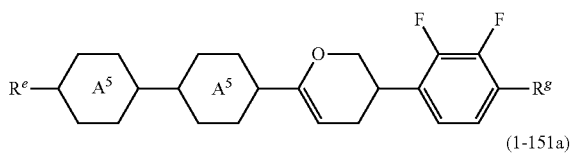
(1-151a)

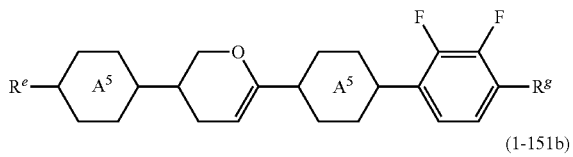
(1-151b)

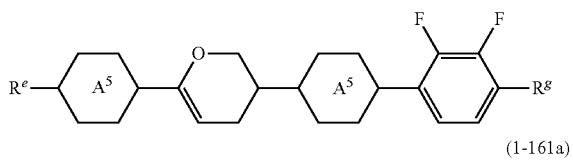
(1-161a)

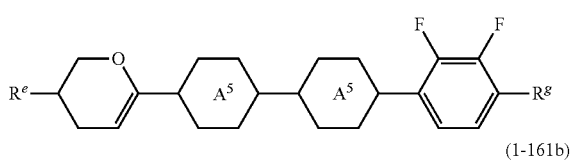
(1-161b)

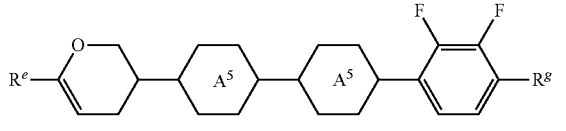

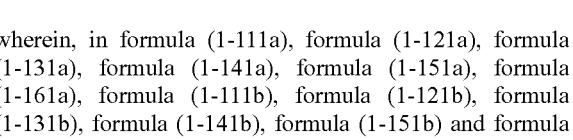

wherein, in formula (1-111a), formula (1-121a), formula (1-131a), formula (1-141a), formula (1-151a), formula (1-161a), formula (1-111b), formula (1-121b), formula (1-131b), formula (1-141b), formula (1-151b) and formula (1-161b), R$^e$ and R$^g$ are independently alkyl having 1 to 10 carbons, alkenyl having 2 to 10 carbons or alkoxy having 1 to 9 carbons; and ring A$^5$ is 1,4-cyclohexylene, 1,4-phenylene, 2-fluoro-1,4-phenylene or 2,3-difluoro-1,4-phenylene.

Item 11. The compound according to item 1 or 2, represented by any one of formula (1-211a), formula (1-212a), formula (1-213a), formula (1-231a), formula (1-311a), formula (1-331a), formula (1-361a), formula (1-211b), formula (1-212b), formula (1-213b), formula (1-231b), formula (1-311b), formula (1-331b) and formula (1-361b):

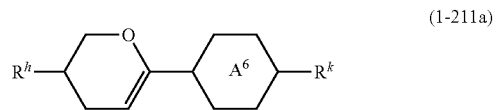
(1-211a)

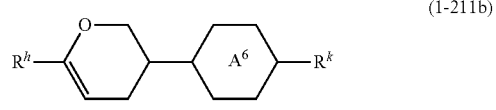
(1-211b)

-continued

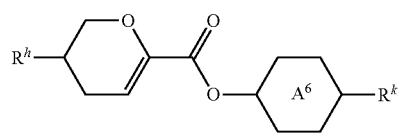
(1-212a)

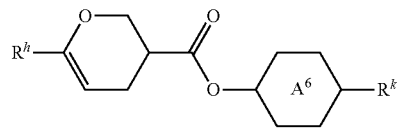
(1-212b)

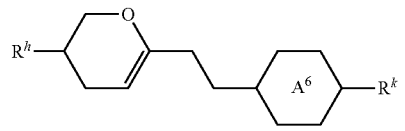
(1-213a)

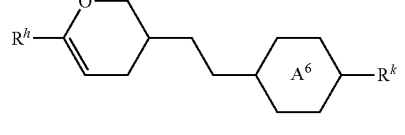
(1-213b)

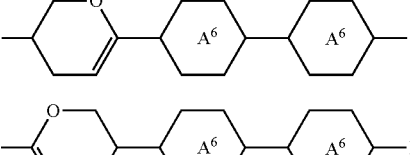
(1-231a)

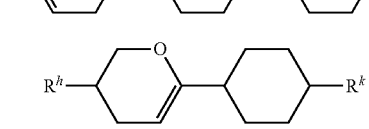
(1-231b)

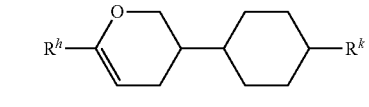
(1-311a)

(1-311b)

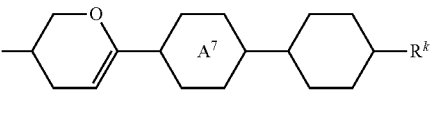
(1-331a)

(1-331b)

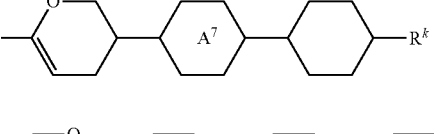
(1-361a)

(1-361b)

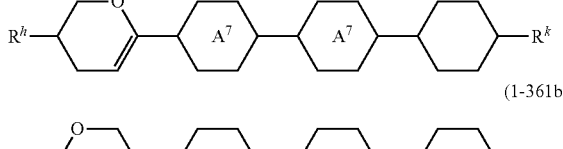

wherein, $R^h$ and $R^k$ are independently alkyl having 1 to 10 carbons, alkenyl having 2 to 10 carbons or alkoxy having 1 to 9 carbons;

ring $A^6$ is 1,4-cyclohexylene, 1,4-phenylene or 2-fluoro-1,4-phenylene; and ring $A^7$ is 1,4-phenylene or 2-fluoro-1,4-phenylene.

Item 12. A liquid crystal composition, containing the compound according to any one of items 1 to 11.

Item 13. A liquid crystal composition having a nematic phase and containing at least one compound selected from the group of compounds represented by formula (1) as a first component and at least one compound selected from the group of compounds represented by formulas (2) to (4) as a second component:

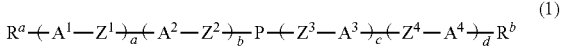
(1)

wherein, in formula (1), $R^a$ and $R^b$ are independently alkyl having 1 to 10 carbons, and in the alkyl, at least one of —CH$_2$— may be replaced by —O—, —S—, —CO— or —SiH$_2$—, and at least one of —CH$_2$CH$_2$— may be replaced by —CH=CH— or —C≡C—;

ring $A^1$, $A^2$, $A^3$ and $A^4$ are independently 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one of —CH$_2$— may be replaced by —O—, —S—, —CO— or —SiH$_2$—, at least one of —CH$_2$CH$_2$— may be replaced by —CH=CH— or —CH=N—, and in the divalent groups, at least one of hydrogen may be replaced by fluorine, chlorine, —C≡N, —CF$_3$, —CHF$_2$, —CH$_2$F, —OCF$_3$, —OCHF$_2$ or —OCH$_2$F; and P is a divalent group represented by formula (pr-1) or (pr-2):

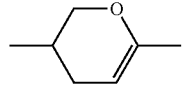
(pr-1)

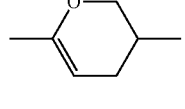
(pr-2)

wherein, $Z^1$, $Z^2$, $Z^3$ and $Z^4$ are independently a single bond or alkylene having 1 to 6 carbons, and in the alkylene, at least one of —CH$_2$— may be replaced by —O—, —S—, —CO— or —SiH$_2$—, one or two of —CH$_2$CH$_2$— may be replaced by —CH=CH— or —C≡C—, and in the divalent groups, at least one of hydrogen may be replaced by fluorine or chlorine;

a, b, c and d are independently 0, 1 or 2, and a sum of a, b, c and d is 5 or less;

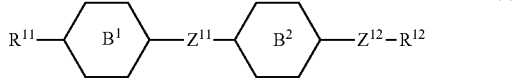
(2)

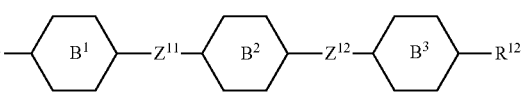
(3)

(4)

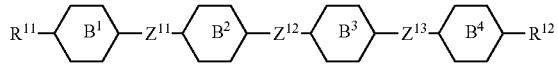

wherein, in formulas (2) to (4), $R^{11}$ and $R^{12}$ are independently alkyl having 1 to 10 carbons or alkenyl having 2 to 10 carbons, and in the alkyl or the alkenyl, at least one of —CH$_2$— may be replaced by —O—, at least one of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —CH$_2$CH$_2$—, —CH=CH—, —C≡C— or —COO—.

Item 14. The liquid crystal composition according to item 13, further containing at least one compound selected from the group of compounds represented by formulas (5) to (7) as a third component:

(5)

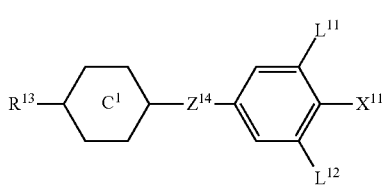

(6)

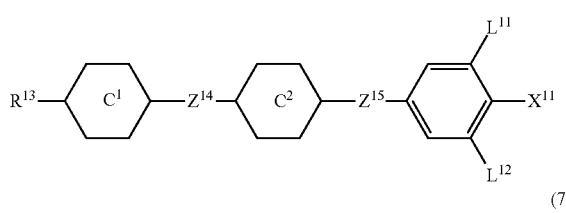

(7)

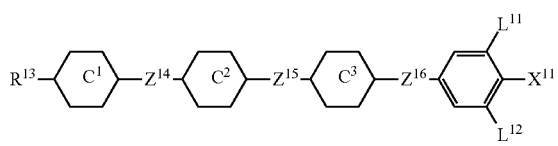

wherein, in formulas (5) to (7), $R^{13}$ is alkyl having 1 to 10 carbons or alkenyl having 2 to 10 carbons, and in the alkyl and the alkenyl, at least one of —CH$_2$— may be replaced by —O—, at least one of hydrogen may be replaced by fluorine;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

Item 15. The liquid crystal composition according to item 13, further containing at least one compound selected from the group of compounds represented by formula (8) as the third component:

(8)

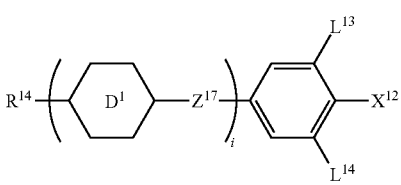

wherein, in formula (8), $R^{14}$ is alkyl having 1 to 10 carbons or alkenyl having 2 to 10 carbons, and in the alkyl and the alkenyl, at least one of —CH$_2$— may be replaced by —O—, at least one of hydrogen may be replaced by fluorine;

$X^{12}$ is —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —CH$_2$CH$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

Item 16. The liquid crystal composition according to item 13, further containing at least one compound selected from the group of compounds represented by formulas (9) to (15) as the third component:

(9)

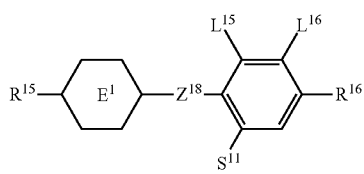

(10)

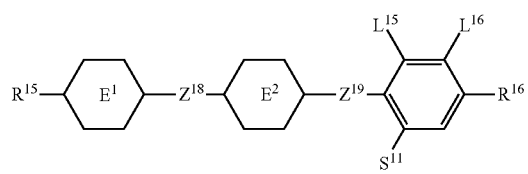

(11)

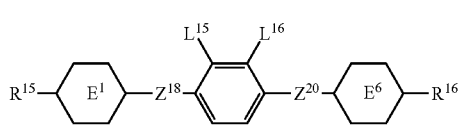

(12)

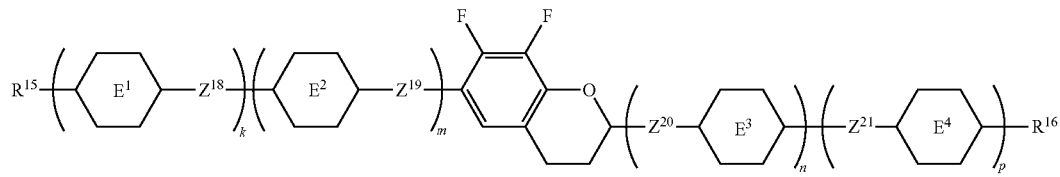

(13)

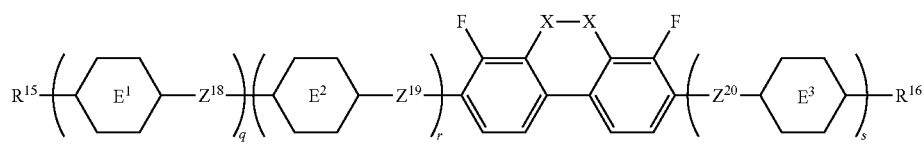

(14)

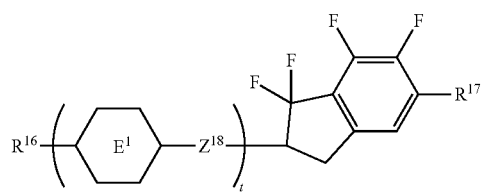

(15)

wherein, in formulas (9) to (15), $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, at least one of hydrogen may be replaced by fluorine;

$R^{17}$ is hydrogen, fluorine, alkyl having 1 to 10 carbons or alkenyl having 2 to 10 carbons, and in the alkyl and the alkenyl, at least one of —$CH_2$— may be replaced by —O—, at least one of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 17. A liquid crystal display device, including the liquid crystal composition according to any one of items 12 to 16.

The invention further includes the following items: (a) a composition having a nematic phase and containing at least one compound selected from the group of compounds represented by formula (1) as the first component, at least one compound selected from the group of compounds represented by formulas (2) to (4) as the second component, and at least one compound selected from the group of compounds represented by formulas (5) to (15) as the third component; (b) the composition according to item (a), having a large positive dielectric anisotropy, in which a ratio of the first component is in the range of 5% by weight to 60% by weight, a ratio of the second component is 30% by weight or more, and a ratio of the third component is in the range of 10% by weight to 95% by weight, based on the weight of the composition; and (c) the composition according to item (a), having a large negative dielectric anisotropy, in which a ratio of the first component is in the range of 5% by weight to 60% by weight, a ratio of the second component is 30% by weight or more, and a ratio of the third component is in the range of 10% by weight to 95% by weight, based on the weight of the composition.

The invention further includes the following items: (d) the composition, further containing at least one optically active compound, the antioxidant, ultraviolet light absorber, light stabilizer, heat stabilizer, antifoaming agent, polymerizable compound, polymerization initiator and polymerization inhibitor; (e) the composition, in which a maximum temperature of the nematic phase is 70° C. or more, optical anisotropy (measured at 25° C.) at a wavelength of 589 nanometers is 0.07 or more, and dielectric anisotropy (measured at 25° C.) at a frequency of 1 kHz is 2 or more; and (f) the composition, in which a maximum temperature of the nematic phase is 70° C. or more, optical anisotropy (measured at 25° C.) at a wavelength of 589 nanometers is 0.08 or more, and dielectric anisotropy (measured at 25° C.) at a frequency of 1 kHz is −2 or less.

The invention further includes the following items: (g) a device including the composition and having a PC mode, a TN mode, an STN mode, an ECB mode, an OCB mode, an IPS mode, a VA mode, an FFS mode, an FPA mode or a PSA mode; (h) an AM device including the composition; (i) a transmissive device, including the composition; (j) use of the composition as the composition having the nematic phase; and (k) use of an optically active composition by adding the optically active compound to the composition.

Compound (1) will be first described and then description will be made in the order of a synthetic method, the liquid crystal composition and the liquid crystal display device.

1. Compound (1)

Compound (1) has a feature of having a divalent group represented by formula (pr-1) or (pr-2) described below.

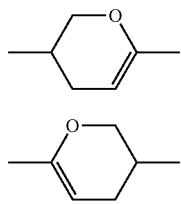

(pr-1)

(pr-2)

The compound is physically and chemically significantly stable under conditions in which a device is ordinarily used and has good compatibility with other liquid crystal compounds. A composition containing the compound is stable under conditions in which the device is ordinarily used. Even if the composition is stored at a low temperature, no compound precipitates in the form of crystals (or a smectic phase). The compound has general physical properties required for the compound, such as a suitable optical anisotropy and a suitable dielectric anisotropy.

Preferred examples of terminal groups $R^a$ and $R^b$, rings $A^1$, $A^2$, $A^3$ and $A^4$, and bonding groups $Z^1$, $Z^2$, $Z^3$ and $Z^4$ in compound (1) are as described below. The examples also apply to a subordinate formula of formula (1) for compound (1).

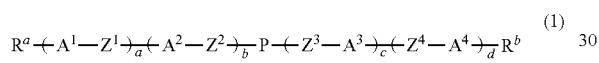

(1)

In formula (1), $R^a$ and $R^b$ are independently alkyl having 1 to 10 carbons, and in the alkyl, at least one of —CH$_2$— may be replaced by —O—, —S—, —CO— or —SiH$_2$—, and at least one of —CH$_2$CH$_2$— may be replaced by —CH=CH— or —C≡C—.

Preferred $R^a$ or $R^b$ is alkyl, alkoxy, alkoxyalkyl, alkoxyalkoxy, alkylthio, alkylthioalkoxy, acyl, acylalkyl, acyloxy, acyloxyalkyl, alkoxycarbonyl, alkoxycarbonylalkyl, alkenyl, alkenyloxy, alkenyloxyalkyl, alkoxyalkenyl, alkynyl, alkynyloxy, silaalkyl and disilaalkyl. In the groups, a straight chain is preferred to a branched chain. Even if $R^a$ or $R^b$ is a branched chain group, when the group is optically active, such a group is preferred. Further preferred $R^a$ or $R^b$ is alkyl, alkoxy, alkoxyalkyl and alkenyl. Most preferred $R^a$ or $R^b$ is alkyl, alkoxy and alkenyl.

A preferred configuration of —CH=CH— in the alkenyl depends on a position of a double bond. Trans is preferred in alkenyl such as 1-propenyl, 1-butenyl, 1-pentenyl, 1-hexenyl, 3-pentenyl and 3-hexenyl. Cis is preferred in alkenyl such as 2-butenyl, 2-pentenyl, and 2-hexenyl.

Specific $R^a$ or $R^b$ is methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl and 1-pentenyl.

Further preferred $R^a$ or $R^b$ is ethyl, propyl, butyl, pentyl, methoxy, ethoxy, propoxy, butoxy, pentyloxy, methoxymethyl, ethoxymethyl, propoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy and 2-pentenyloxy. Most preferred $R^a$ or $R^b$ is ethyl, propyl, butyl, pentyl, methoxy, ethoxy, propoxy, methoxymethyl, vinyl, 1-propenyl, 3-butenyl and 3-pentenyl.

In formula (1), $A^1$, $A^2$, $A^3$ and $A^4$ are independently 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or fluorene-2,7-diyl, and in the groups, at least one of —CH$_2$— may be replaced by —O—, —S—, —CO— or —SiH$_2$—, at least one of —CH$_2$CH$_2$— may be replaced by —CH=CH— or —CH=N—, and in the divalent groups, at least one of hydrogen may be replaced by fluorine, chlorine, —C≡N, —CF$_2$, —CHF$_2$, —CH$_2$F, —OCF$_3$, —OCHF$_2$ or —OCH$_2$F.

Preferred examples of groups "in the groups, at least one of —CH$_2$— may be replaced by —O—, —S—, —CO— or —SiH$_2$—, and at least one of —CH$_2$—CH$_2$— may be replaced by —CH=CH— or —CH=N—" include a divalent group represented by formulas (16-1) to (16-50) described below. Further preferred examples include a divalent group represented by formulas (16-1) to (16-4), formula (16-15), formula (16-23), formulas (16-27) to (26-29), formula (16-36), formula (16-39) and formula (16-45). Most preferred examples include a divalent group represented by formula (16-1), formula (16-2) and formulas (16-27) to (16-29).

(16-1)

(16-2)

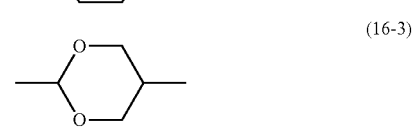

(16-3)

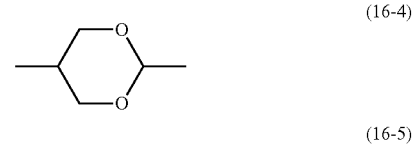

(16-4)

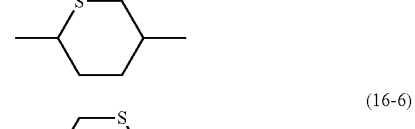

(16-5)

(16-6)

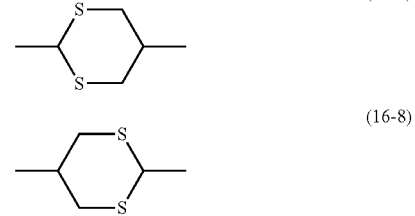

(16-7)

(16-8)

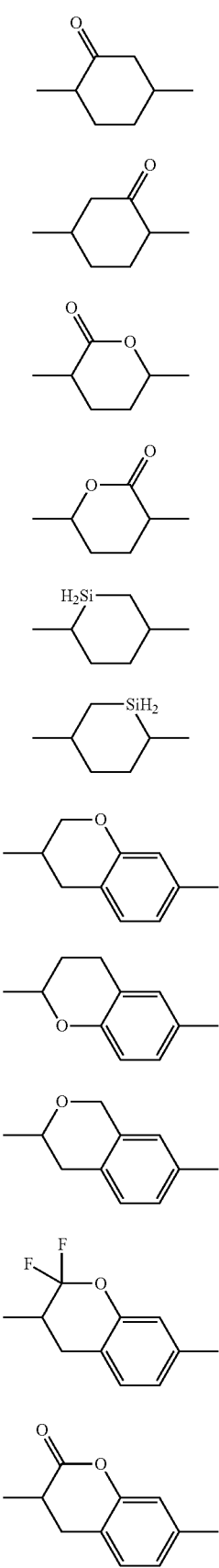
(16-9)
(16-10)
(16-11)
(16-12)
(16-13)
(16-14)
(16-15)
(16-16)
(16-17)
(16-18)
(16-19)
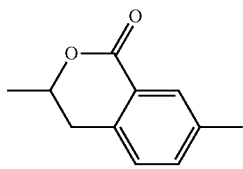
(16-20)
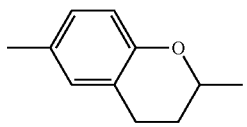
(16-21)
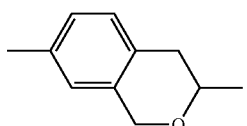
(16-22)
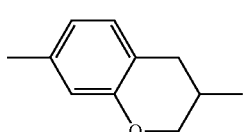
(16-23)
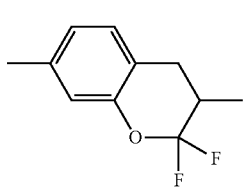
(16-24)
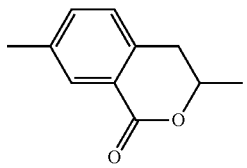
(16-25)
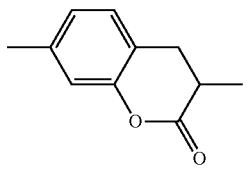
(16-26)
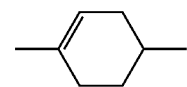
(16-27)
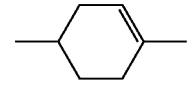
(16-28)
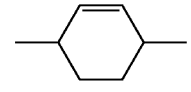
(16-29)
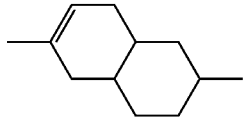
(16-30)

(16-31) 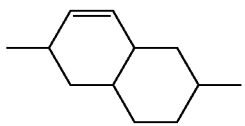

(16-32) 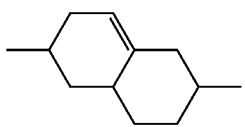

(16-33) 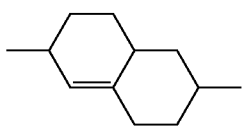

(16-34) 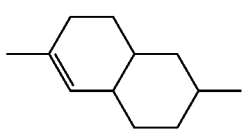

(16-35) 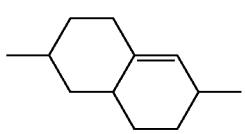

(16-36) 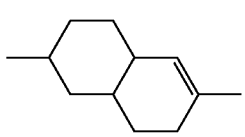

(16-37) 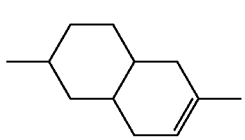

(16-38) 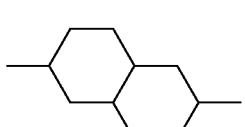

(16-39) 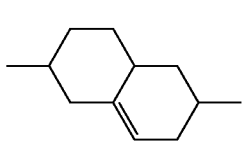

(16-40) 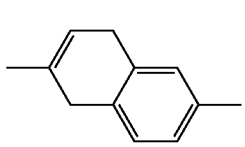

(16-41) 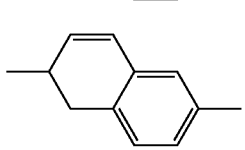

(16-42) 

(16-43) 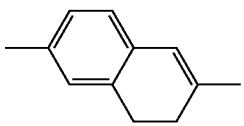

(16-44) 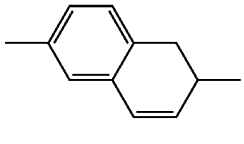

(16-45) 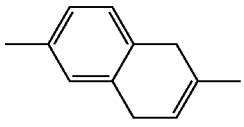

(16-46) 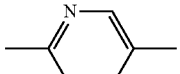

(16-47) 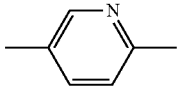

(16-48) 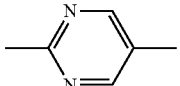

(16-49) 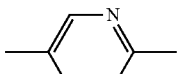

(16-50) 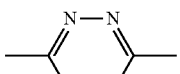

Preferred examples of groups "in the divalent groups, at least one of hydrogen may be replaced by fluorine, chlorine, —C≡N, —CF$_3$, —CHF$_2$, —CH$_2$F, —OCF$_3$, —OCHF$_2$ or —OCH$_2$F" include a divalent group represented by formulas (17-1) to (17-77) described below. Further preferred examples include a divalent group represented by formulas (17-1) to (17-6), formulas (17-10) to (17-15), formulas (17-54) to (17-59) and formulas (17-72) to (17-77). Most preferred examples include a divalent group represented by formulas (17-1) to (17-6), formulas (17-10) to (17-15), formulas (17-57) to (17-59) and formulas (17-72) to (17-77).

(17-1) 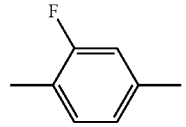

(17-2) 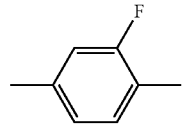

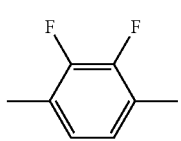 (17-3)
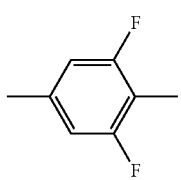 (17-4)
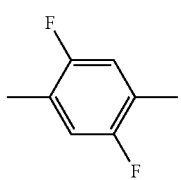 (17-5)
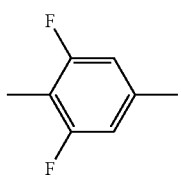 (17-6)
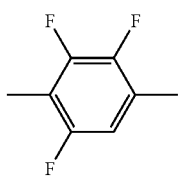 (17-7)
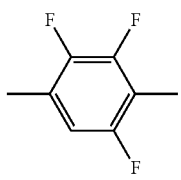 (17-8)
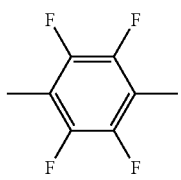 (17-9)
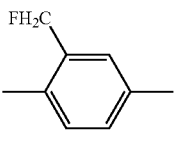 (17-10)
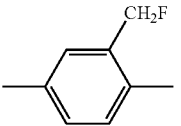 (17-11)
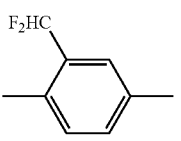 (17-12)
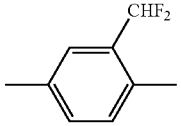 (17-13)
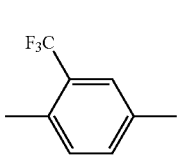 (17-14)
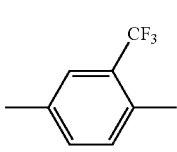 (17-15)
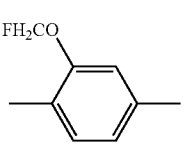 (17-16)
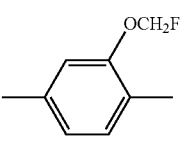 (17-17)
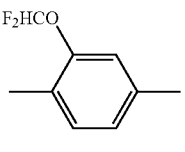 (17-18)
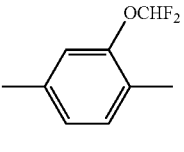 (17-19)
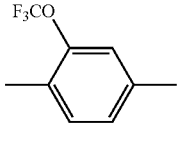 (17-20)
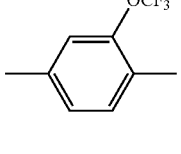 (17-21)
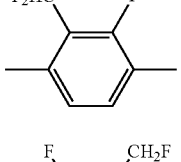 (17-22)
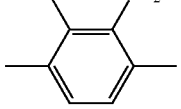 (17-23)

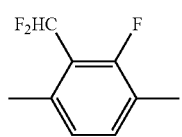 (17-24)
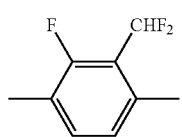 (17-25)
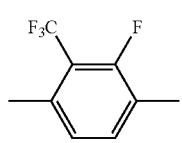 (17-26)
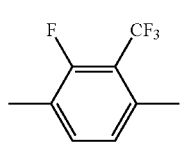 (17-27)
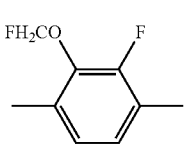 (17-28)
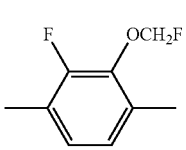 (17-29)
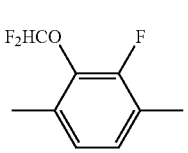 (17-30)
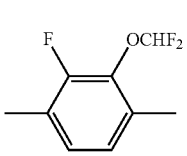 (17-31)
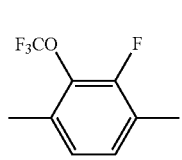 (17-32)
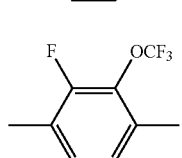 (17-33)
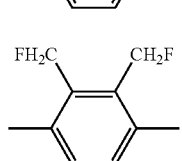 (17-34)
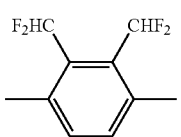 (17-35)
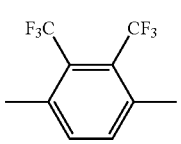 (17-36)
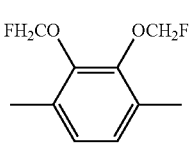 (17-37)
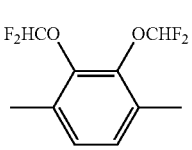 (17-38)
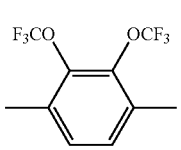 (17-39)
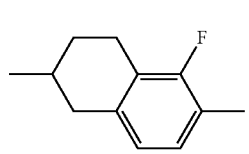 (17-40)
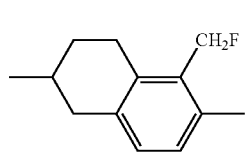 (17-41)
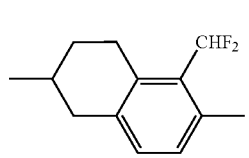 (17-42)
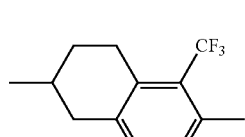 (17-43)
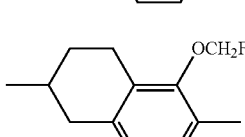 (17-44)
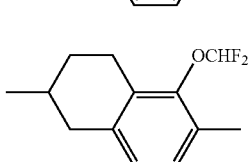 (17-45)

-continued
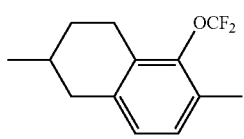 (17-46)
 (17-47)
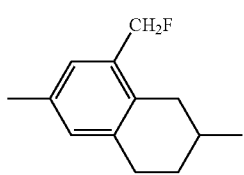 (17-48)
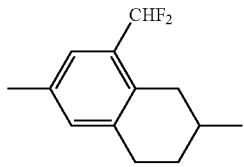 (17-49)
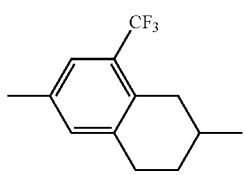 (17-50)
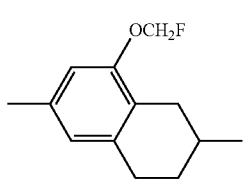 (17-51)
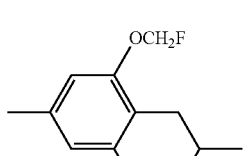 (17-52)
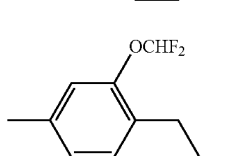 (17-53)
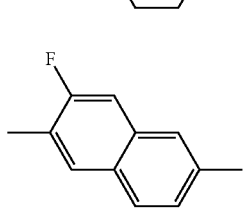 (17-54)
-continued
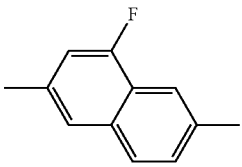 (17-55)
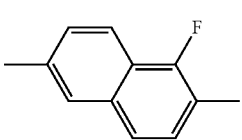 (17-56)
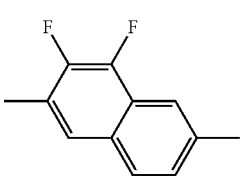 (17-57)
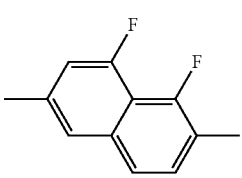 (17-58)
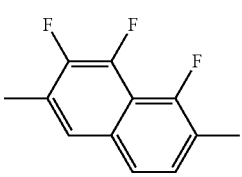 (17-59)
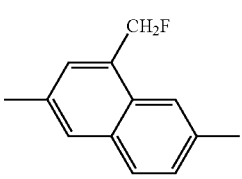 (17-60)
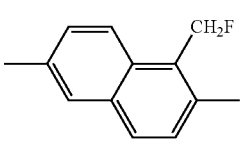 (17-61)
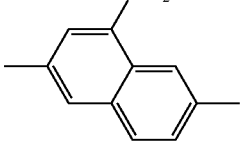 (17-62)
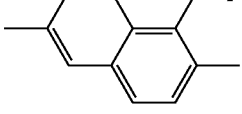 (17-63)

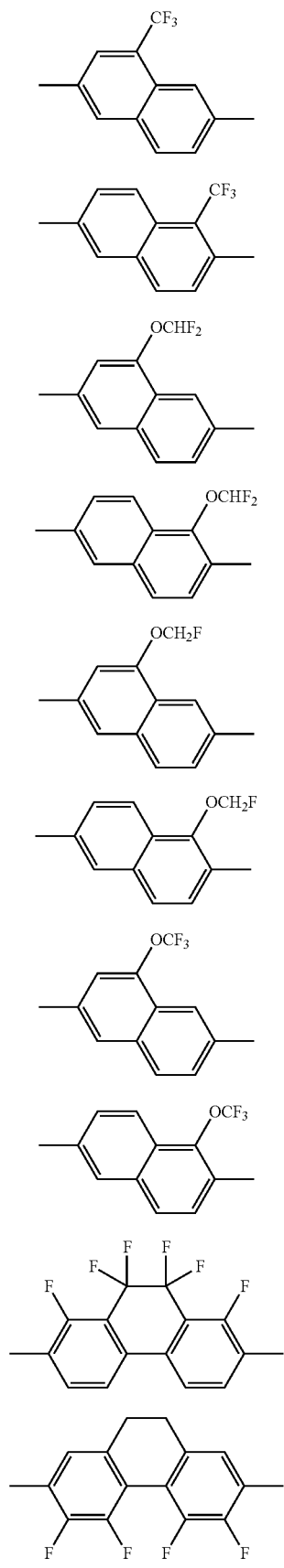

(17-64)
(17-65)
(17-66)
(17-67)
(17-68)
(17-69)
(17-70)
(17-71)
(17-72)
(17-73)

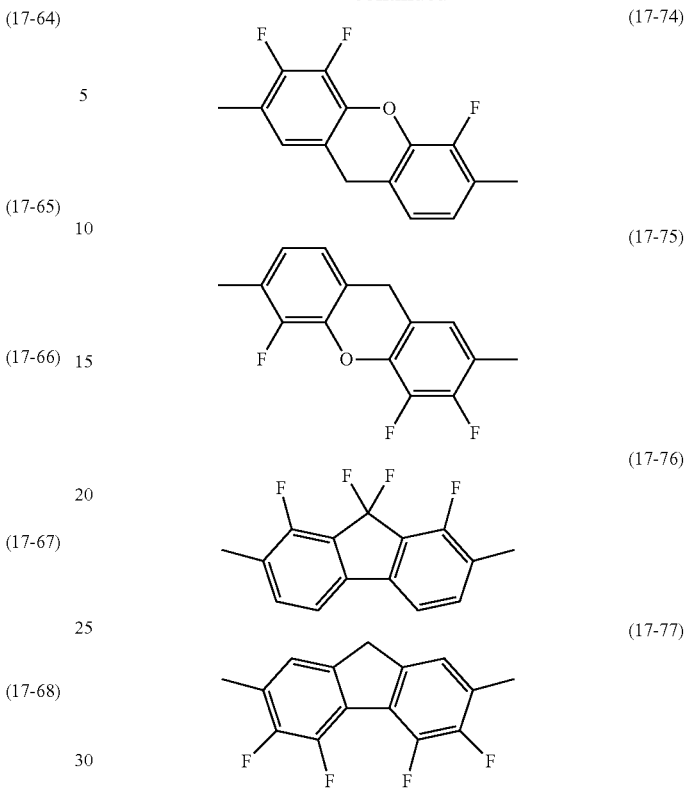

(17-74)
(17-75)
(17-76)
(17-77)

Further preferred ring $A^1$, $A^2$, $A^3$ or $A^4$ is 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene, pyridine-2,5-diyl, 3-fluoropyridine-2,5-diyl, pyrimidine-2,5-diyl, pyridazine-2,5-diyl, decahydronaphthalene-2,6-diyl, 1,2,3,4-tetrahydronaphthalene-2,6-diyl and naphthalene-2,6-diyl. With regard to a configuration of 1,4-cyclohexylene and 1,3-dioxane-2,5-diyl, trans is preferred to cis.

Most preferred ring $A^1$, $A^2$, $A^3$ or $A^4$ is 1,4-cyclohexylene, 1,4-phenylene, 2-fluoro-1,4-phenylene, 2,3-difluoro-1,4-phenylene, 2,5-difluoro-1,4-phenylene, 2,6-difluoro-1,4-phenylene, pyridine-2,5-diyl, and pyrimidine-2,5-diyl.

In formula (1), P is a divalent group represented by formula (pr-1) or (pr-2).

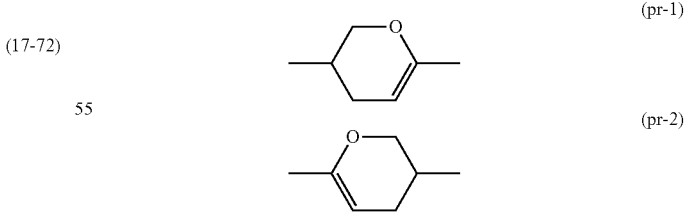

(pr-1)
(pr-2)

A compound having the divalent group represented by formula (pr-1) is preferred from a viewpoint of the large positive dielectric anisotropy. A compound having the divalent group represented by formula (pr-2) is preferred from a viewpoint of the large negative dielectric anisotropy.

In formula (1), $Z^1$, $Z^2$, $Z^3$ and $Z^4$ are independently a single bond or alkylene having 1 to 6 carbons, and in the alkylene, at least one of —CH$_2$— may be replaced by —O—, —S—, —CO— or —SiH$_2$—, one or two of —CH$_2$CH$_2$— may be replaced by —CH═CH— or —C≡C—, and in the divalent groups, at least one of hydrogen may be replaced by fluorine or chlorine.

Specific examples of Z$^1$, Z$^2$, Z$^3$ or Z$^4$ include a single bond, —COO—, —OCO—, —CH$_2$O—, —OCH$_2$—, —CF$_2$O—, —OCF$_2$—, —CH$_2$CH$_2$—, —CH═CH—, —CF═CH—, —CH═CF—, —CF═CF—, —C≡C—, —CH$_2$CO—, —COCH$_2$—, —CH$_2$SiH$_2$—, —SiH$_2$CH$_2$—, —(CH$_2$)$_4$—, —(CH$_2$)$_2$COO—, —(CH$_2$)$_2$OCO—, —OCO(CH$_2$)$_2$—, —COO(CH$_2$)$_2$—, —(CH$_2$)$_2$CF$_2$O—, —(CH$_2$)$_2$OCF$_2$—, —OCF$_2$(CH$_2$)$_2$—, —CF$_2$O(CH$_2$)$_2$—, —(CH$_2$)$_3$O— or —O(CH$_2$)$_3$—. With regard to a configuration of a double bond of a bonding group such as —CH═CH—, —CF═CF—, —CH═CH—CH$_2$O— and —OCH$_2$—CH═CH—, trans is preferred to cis.

Preferred Z$^1$, Z$^2$, Z$^3$ or Z$^4$ is a single bond, —COO—, —OCO—, —CH$_2$O—, —OCH$_2$—, —CF$_2$O—, —OCF$_2$—, —CH$_2$CH$_2$—, —CH═CH—, —CF═CF—, —C≡C— and —(CH$_2$)$_4$—. Further preferred Z$^1$, Z$^2$, Z$^3$ or Z$^4$ is a single bond, —CH$_2$CH$_2$—, —COO—, —OCO—, —CF$_2$O—, —OCF$_2$—, —CH═CH— and —C≡C—. Most preferred Z$^1$, Z$^2$, Z$^3$ or Z$^4$ is a single bond.

In formula (1), a, b, c and d are independently 0, 1 or 2, and a sum of a, b, c and d is 5 or less. Compound (1) has a bicycle to a hexacycle. The rings also include a condensed ring or a crosslinked six-membered ring in addition to an ordinary six-membered ring. When compound (1) has the bicycle, compatibility with other liquid crystal compounds is good. When compound (1) has the bicycle or tricycle, the viscosity is small. When compound (1) has the tricycle or tetracycle, the maximum temperature is high. When compound (1) has the tetracycle, the temperature range of the liquid crystal phase is wide.

The physical properties such as the optical anisotropy and the dielectric anisotropy can be arbitrarily adjusted by suitably selecting a terminal group, a ring and a bonding group of compound (1). An effect of a kind of terminal groups R$^a$ and R$^b$, rings A$^1$, A$^2$, A$^3$ and A$^4$, and bonding groups Z$^1$, Z$^2$, Z$^3$ and Z$^4$ on the physical properties of compound (1) is as described below.

Compound (1) is classified into three types in which the dielectric anisotropy is positively large, negatively large and small. The compound having a large dielectric anisotropy is a component for decreasing a threshold voltage of the device. The compound having the small dielectric anisotropy is a component for decreasing the viscosity or increasing the maximum temperature of the composition. "Large" or "small" is expressed based on a relative comparison. One example of "small" includes the dielectric anisotropy in the range from approximately −1 to approximately +2. In formula (1-1), R$^a$ and R$^b$ are alkyl, alkoxy or the like, and Y$^1$ and Y$^2$ are an electron-withdrawing group such as fluorine and —CF$_3$. The compound has the large negative dielectric anisotropy. In formula (1-2) and (1-3), R$^a$ and R$^b$ are alkyl, alkoxy or the like. The compounds have the small dielectric anisotropy.

In the compound, when R$^a$ or R$^b$ has a straight chain, the temperature range of the liquid crystal phase is wide, and the viscosity is small. When R$^a$ or R$^b$ has a branched chain, the compatibility with other liquid crystal compounds is good. A compound in which R$^a$ or R$^b$ is an optically active group is useful as a chiral dopant. A reverse twisted domain to be generated in the device can be prevented by adding the compound to the composition. A compound in which R$^a$ or R$^b$ is not an optically active group is useful as a component of the composition. When R$^a$ or R$^b$ is alkenyl, a preferred configuration depends on a position of a double bond. An alkenyl compound having a preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

When ring A$^1$, A$^2$, A$^3$ or A$^4$ is 1,4-phenylene in which at least one of hydrogen is replaced by fluorine or chlorine, pyridine-2,5-diyl or 1,3-dioxane-2,5-diyl, the dielectric anisotropy is positively large. When the ring is 1,4-phenylene in which at least one of hydrogen may be replaced by fluorine or chlorine, pyridine-2,5-diyl, pyrimidine-2,5-diyl or pyridazine-3,6-diyl, the optical anisotropy is large. When the ring is 1,4-cyclohexylene, 1,4-cyclohexenylene or 1,3-dioxane-2,5-diyl, the optical anisotropy is small.

When at least two rings are 1,4-cyclohexylene, the maximum temperature is high, the optical anisotropy is small, and the viscosity is small. When at least one ring is 1,4-phenylene, the optical anisotropy is comparatively large, and an orientational order parameter is large. When at least two rings are 1,4-phenylene, the optical anisotropy is large, the temperature range of the liquid crystal phase is wide, and the maximum temperature is high.

When a bonding group Z$^1$, Z$^2$, Z$^3$ or Z$^4$ is a single bond, —CH$_2$CH$_2$—, —CH$_2$O—, —CF$_2$O—, —OCF$_2$—, —CH═CH—, —CF═CF— or —(CH$_2$)$_4$—, the viscosity is small. When the bonding group is a single bond, —CH$_2$CH$_2$—, —OCF$_2$—, —CF$_2$O— or —CH═CH—, the viscosity is smaller. When the bonding group is —CH═CH—, the temperature range of the liquid crystal phase is wide, and an elastic constant ratio K$_{33}$/K$_{11}$ (K$_{33}$: bend elastic constant, K$_{11}$: splay elastic constant) is large. When the bonding group is —C≡C—, the optical anisotropy is large.

When compound (1) has a bicycle or a tricycle, the viscosity is small. When compound (1) has a tetracycle or a pentacycle, the maximum temperature is high. As described above, a compound having objective physical properties can be obtained by suitably selecting the kind of the terminal group, the ring and the bonding group, and the number of rings. Accordingly, compound (1) is useful as the component of the composition to be used for the device having the mode such as PC, TN, STN, ECB, OCB, IPS or VA.

In the compound having the large positive dielectric anisotropy, preferred examples of Z$^1$, Z$^2$, Z$^3$ or Z$^4$ include a single bond, —CH$_2$CH$_2$—, —CF$_2$O—, —OCF$_2$—, —CH═CH—, —CF═CF— or —C≡C—. Further preferred examples include a single bond, —CH$_2$CH$_2$—, —CF$_2$O—, —OCF$_2$— or —CH═CH—. Most preferred examples include a single bond.

In the compound having the large negative dielectric anisotropy, preferred examples of Z$^1$, Z$^2$, Z$^3$ or Z$^4$ include a single bond, —CH$_2$CH$_2$—, —CH$_2$O—, —OCH$_2$—, —CF$_2$O—, —OCF$_2$—, —CH═CH—, —CF═CF— or —C≡C—. Further preferred examples include a single bond, —CH$_2$CH$_2$—, —CH$_2$O—, —OCH$_2$— or —CH═CH—. Most preferred examples include a single bond.

In the compound having the small dielectric anisotropy, preferred examples of Z$^1$, Z$^2$, Z$^3$ or Z$^4$ include a single bond, —COO—, —CH$_2$CH$_2$—, —CH$_2$O—, —OCH$_2$—, —CH═CH— or —C≡C—. Further preferred examples include a single bond, —COO—, —CH$_2$CH$_2$—, —CH═CH— or —C≡C—. Most preferred examples include a single bond.

In formula (1-1), when $Y^1$ and $Y^2$ are fluorine, chlorine, —$CF_3$ or —$CHF_2$, the compound is preferred. When $Y^1$ and $Y^2$ are fluorine or chlorine, the compound is further preferred. When $Y^1$ and $Y^2$ are fluorine, the compound is most preferred. In formula (1-2), when $Y^1$ and $Y^3$ are hydrogen, the compound is preferred. When $Y^1$ is hydrogen and $Y^3$ is fluorine, the compound is also preferred. When $Y^1$ is fluorine and $Y^3$ is hydrogen, the compound is also preferred. When $Y^1$ and $Y^3$ are fluorine, the compound is also preferred.

Preferred examples of compound (1) include compounds (1-1) to (1-3) described in item 2. Further preferred examples are as shown in a subordinate formula described after item 2. Compound (1-1) is suitable for a device having the mode such as the VA mode and the PSA mode. Compound (1-2) and compound (1-3) can be used for all the modes because the dielectric anisotropy is small. In addition, when compound (1-2) or (1-3) has a divalent group, such as 2,3-difluoro-1,4-phenylene, the dielectric anisotropy of the compound is negatively large, and therefore the compound can be used for a device having the mode such as the VA mode and the PSA mode.

Specific Examples of Compound (1)

Preferred examples of compound (1) are represented by formulas (1-1) to (1-3) shown in item 2.

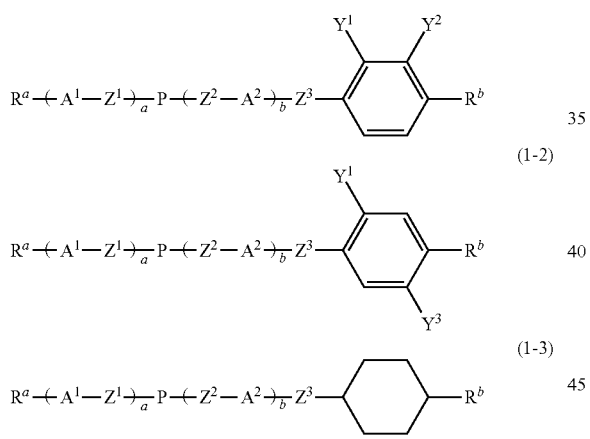

In a compound having a large negative dielectric anisotropy, further preferred examples are represented by formulas (1-11a) to (1-13a), formulas (1-11b) to (1-13b) and formulas (1-14) to (1-16) shown in item 3 and item 8. Most preferred examples are represented by formula (1-111a), formula (1-121a), formula (1-131a), formula (1-141a), formula (1-151a), formula (1-161a), formula (1-111b), formula (1-121b), formula (1-131b), formula (1-141b), formula (1-151b) and formula (1-161b) shown in item 10.

In a compound having a small dielectric anisotropy, further preferred examples are represented by formulas (1-21a) to (1-23a), formulas (1-21b) to (1-23b), formulas (1-31) to (1-36) and formulas (1-24) to (1-26) shown in item 5, 7 and 8. Most preferred examples are represented by formula (1-211a), formula (1-212a), formula (1-213a), formula (1-231a), formula (1-311a), formula (1-331a), formula (1-361a), formula (1-211b), formula (1-212b), formula (1-213b), formula (1-231b), formula (1-311b), formula (1-331b) and formula (1-361b) shown in item 11.

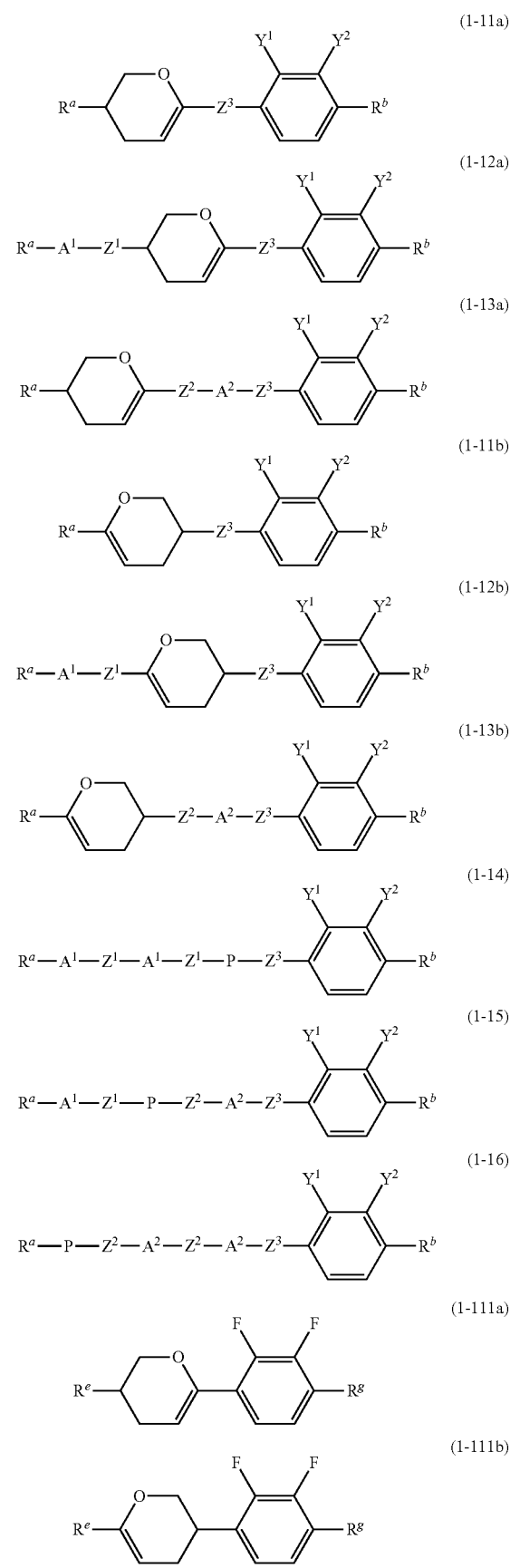

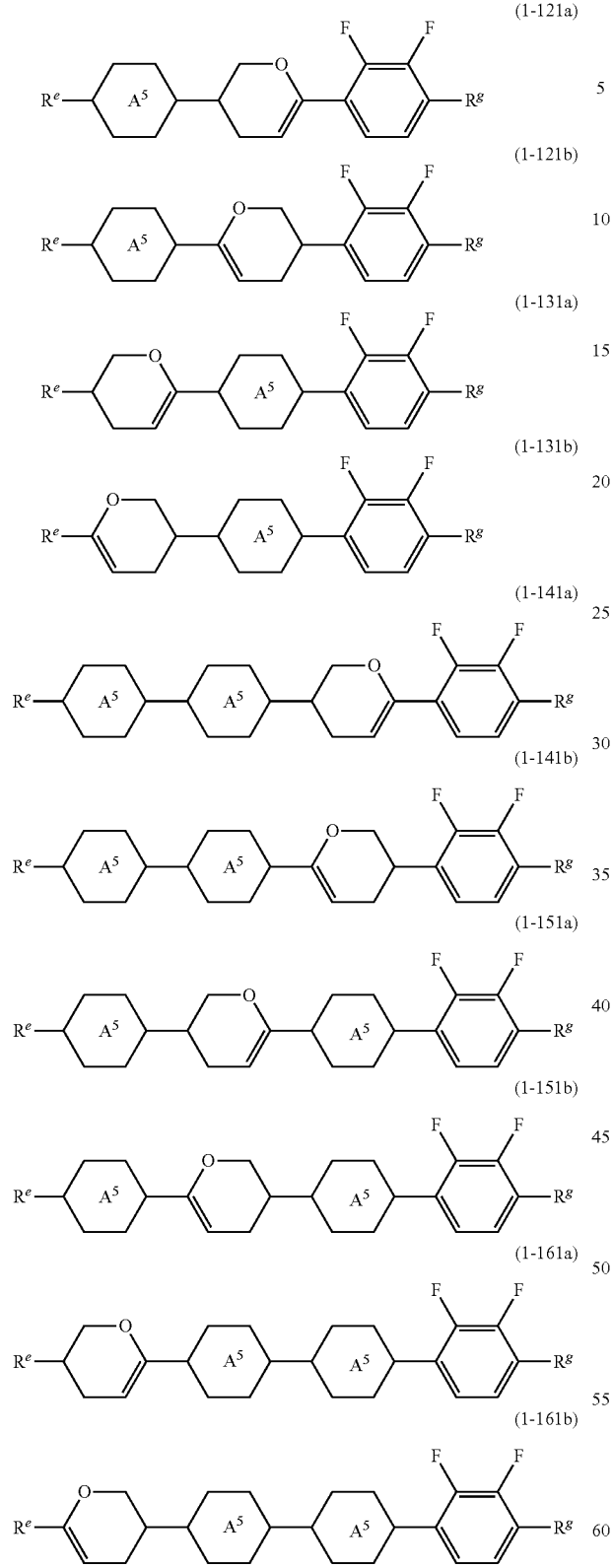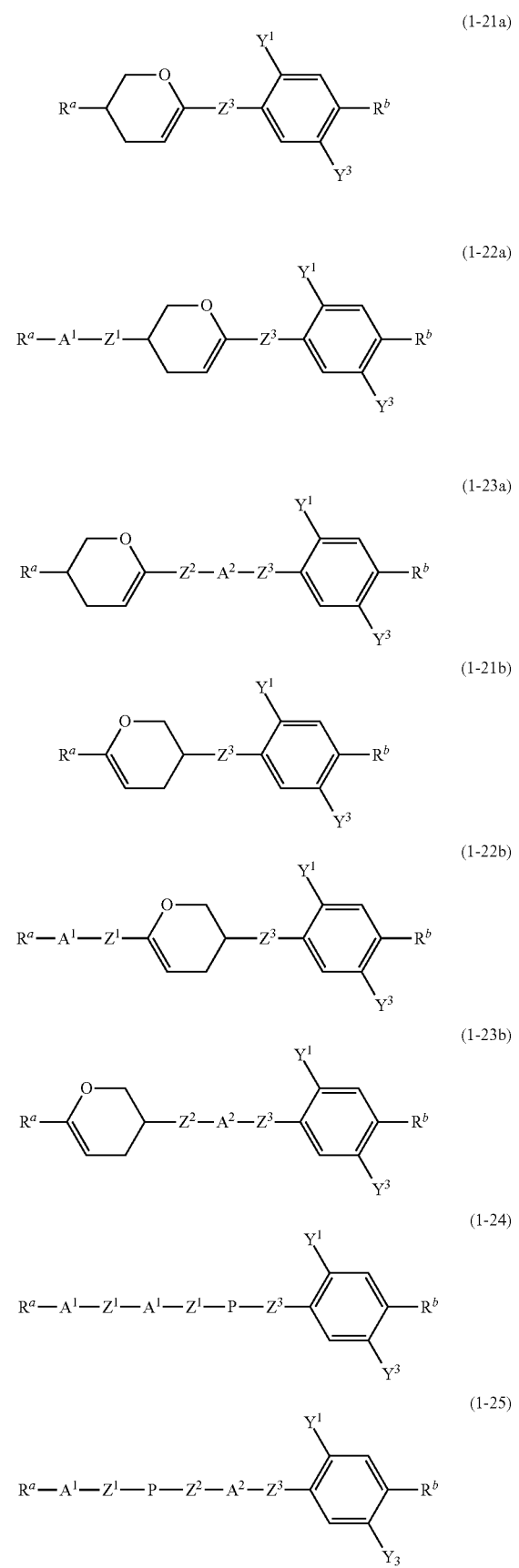
Compounds represented by formula (1-111b), formula (1-121b), formula (1-131b), formula (1-141b), formula (1-151b) and formula (1-161b) have the large negative dielectric anisotropy.

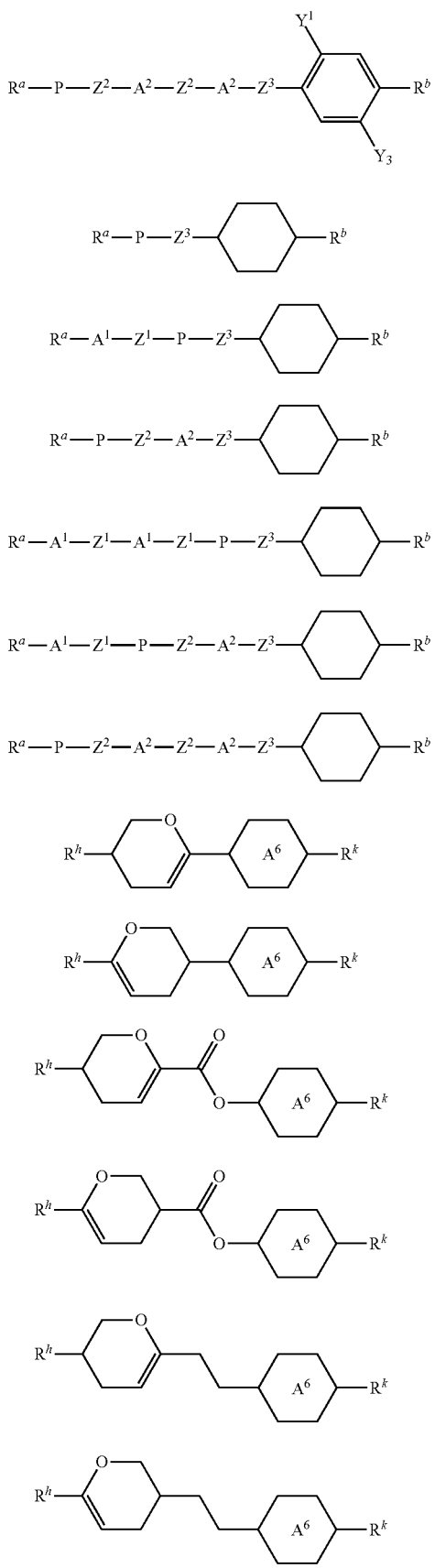

Compounds represented by formula (1-211a), formula (1-213a), formula (1-311a), formula (1-211b), formula (1-213b) and formula (1-311b) have a small viscosity, compounds represented by formula (1-361a) and formula (1-361b) have a high NI; and compounds represented by formula (1-212a), formula (1-231a), formula (1-331a), formula (1-212b), formula (1-231b) and formula (1-331b) have a good balance between the viscosity and NI.

2. Synthetic Method

Compound (1) can be prepared by suitably combining techniques in synthetic organic chemistry. A method for introducing an objective terminal group, ring and bonding group into a starting material is described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.).

First, a scheme is shown with regard to a method of synthesizing bonding groups $Z^1$ to $Z^4$. Next, a reaction according to schemes described in sections (1) to (11) will be described. In the scheme, $MSG^1$ (or $MSG^2$) is a monovalent organic group having at least one ring. A plurality of $MSG^1$ (or $MSG^2$) used in the scheme may be identical or different. Compounds (1A) to compound (1K) correspond to compound (1).

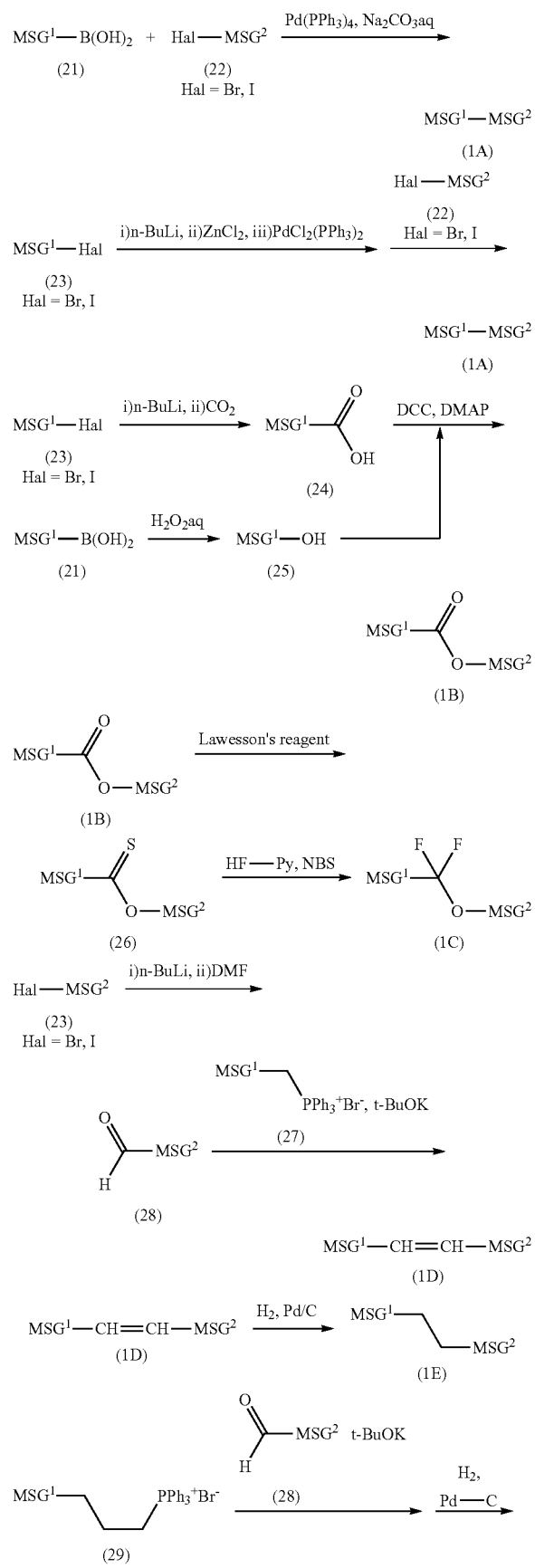
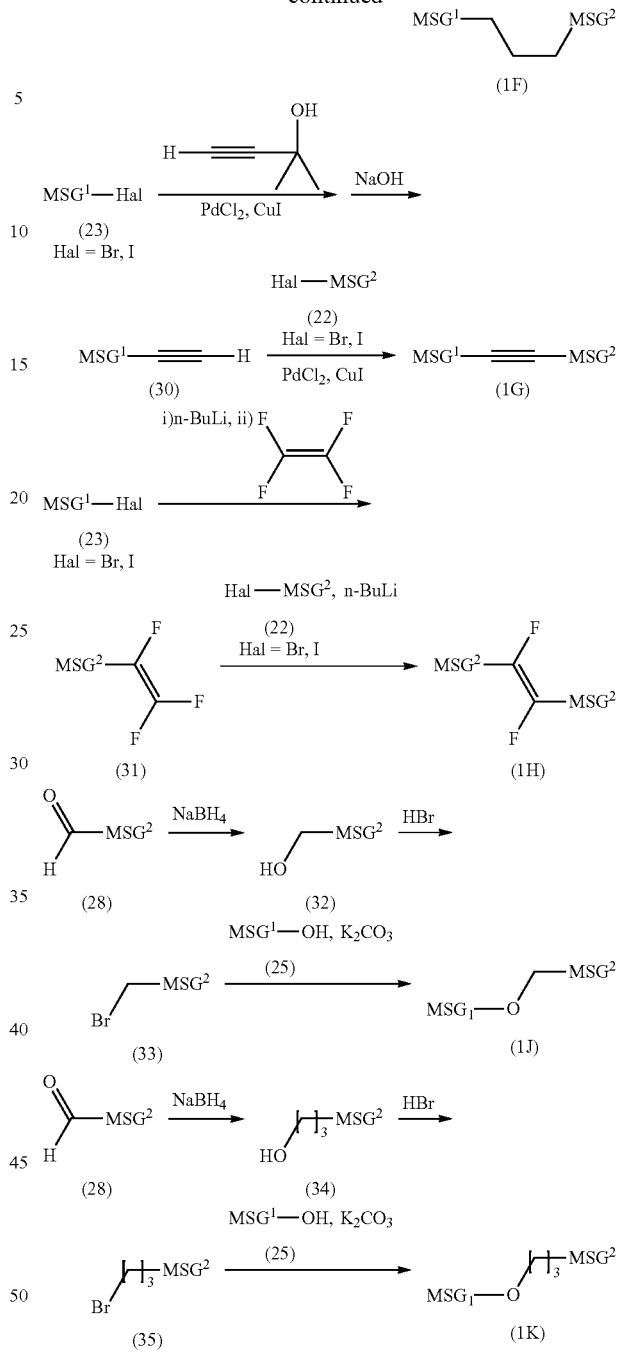

(1) Formation of a Single Bond

Compound (1A) is prepared by allowing aryl boronic acid (21) to react, in the presence of an aqueous carbonate solution and a catalyst such as tetrakis(triphenylphosphine)palladium, with compound (22) prepared according to a known method. Compound (1A) is also prepared by allowing compound (23) prepared according to a known method to react with n-butyllithium and subsequently with zinc chloride, and further with compound (22) in the presence of a catalyst such as dichlorobis(triphenylphosphine)palladium.

(2) Formation of —COO— and —OCO—

Carboxylic acid (24) is obtained by allowing compound (23) to react with n-butyllithium and subsequently with carbon dioxide. Compound (1B) having —COO— is prepared by performing dehydration of compound (24) and phenol (25) to be prepared from compound (21) according to a known method, in the presence of 1,3-dicyclohexylcarbodiimide (DCC) and 4-dimethylaminopyridine (DMAP). A compound having —COO— can also be prepared according to the method.

(3) Formation of —CF$_2$O— and —OCF$_2$—

Compound (26) is obtained by treating compound (1B) with a thiation reagent such as Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768. A compound having —OCF$_2$— can also be prepared according to the method. The bonding groups can also be formed according to the method described in Peer. Kirsch et al., Angew. Chem. Int. Ed. 2001, 40, 1480.

(4) Formation of —CH═CH—

Aldehyde (28) is obtained by treating compound (23) with n-butyllithium and then allowing the treated compound to react with formamide such as N,N-dimethylformamide (DMF). Compound (1D) is prepared by allowing phosphorus ylide generated by treating phosphonium salt (27) prepared according to a known method with a base such as potassium t-butoxide to react with aldehyde (28). A cis isomer is formed depending on reaction conditions, and therefore the cis isomer is isomerized to a trans isomer according to a known method, when necessary.

(5) Formation of —CH$_2$CH$_2$—

Compound (1E) is prepared by hydrogenating compound (1D) in the presence of a catalyst such as palladium on carbon.

(6) Formation of —(CH$_2$)$_4$—

A compound having —(CH$_2$)$_2$—CH═CH— is obtained by using phosphonium salt (29) in place of phosphonium salt (27) according to the method in section (5). Compound (1F) is prepared by performing catalytic hydrogenation of the compound obtained.

(7) Formation of —C≡C—

Compound (30) is obtained by allowing compound (23) to react with 2-methyl-3-butyn-2-ol in the presence of a catalyst including dichloropalladium and copper halide, and then performing deprotection under basic conditions. Compound (1G) is prepared by allowing compound (30) to react with compound (22) in the presence of the catalyst including dichloropalladium and copper halide.

(8) Formation of —CF═CF—

Compound (31) is obtained by treating compound (23) with n-butyllithium and then allowing the treated compound to react with tetrafluoroethylene. Compound (1H) is prepared by treating compound (22) with n-butyllithium, and then allowing the treated compound to react with compound (31).

(9) Formation of —CH$_2$O— and —OCH$_2$—

Compound (32) is obtained by reducing compound (28) with a reducing agent such as sodium borohydride. Compound (33) is obtained by halogenating the obtained compound with hydrobromic acid or the like. Compound (1J) is prepared by allowing compound (33) to react with compound (25) in the presence of potassium carbonate or the like.

(10) Formation of —(CH$_2$)$_2$O— and —O(CH$_2$)$_3$—

Compound (1K) is prepared by using compound (34) in place of compound (32) in a manner similar to the method in section (9).

(11) Formation of —(CF$_2$)$_2$—

A compound having —(CF$_2$)$_2$— is obtained by fluorinating diketone (—COCO—) with sulfur tetrafluoride, in the presence of a hydrogen fluoride catalyst, according to the method described in J. Am. Chem. Soc., 2001, 123, 5414.

Next, a method of synthesizing rings $A^1$ to $A^4$ is described. A starting material is commercially available or a synthetic method is well known with regard to a ring such as 1,4-cyclohexylene, 1,3-dioxane-2,5-diyl, 1,4-phenylene, 2-fluoro-1,4-phenylene, 2,3-difluoro-1,4-phenylene, pyridine-2,5-diyl, or pyrimidine-2,5-diyl. Thus, compounds (64), (67) and (71) described below will be described.

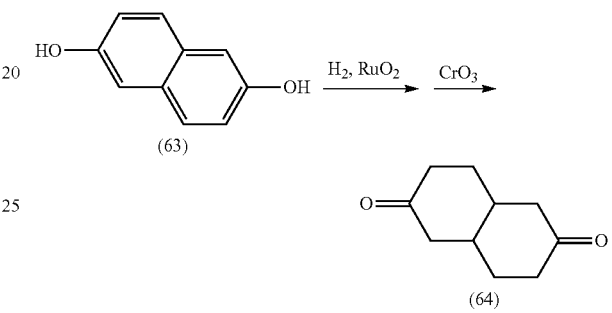

Decahydronaphthalene-2,6-dione (64) is a starting material of a compound having decahydronaphthalene-2,6-diyl. Compound (64) is prepared by reducing diol (63) with hydrogen in the presence of ruthenium oxide, and then oxidizing the resulting compound with chromic oxide, according to the method described in JP 2000-239564 A.

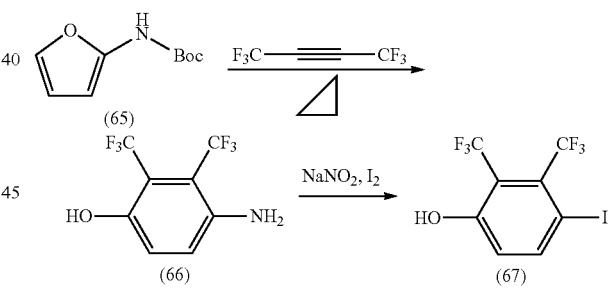

A structural unit of 2,3-(bistrifluoromethyl)phenylene is prepared by the method described in Org. Lett., 2000, 2 (21), 3345. Aniline (66) is prepared by allowing a Diels-Alder reaction between furan (65) and 1,1,1,4,4,4-hexafluoro-2-butyne at a high temperature. Iodide (67) is obtained by carrying out a Sandmeyer reaction according to the method described in Org. Synth. Coll., Vol. 2, 1943, 355. The compound is converted into compound (1) by a technique in general synthetic organic chemistry.

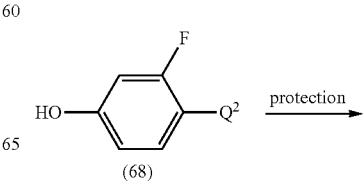

-continued

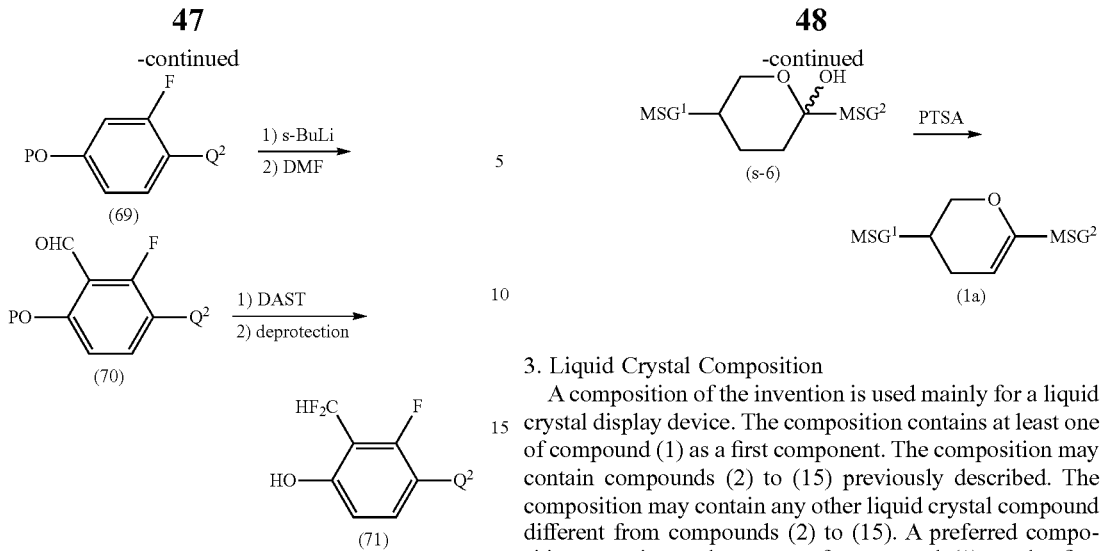

A structural unit of 2-difluoromethyl-3-fluorophenylene is prepared by a method as described below. Compound (69) is obtained by protecting a hydroxy group of compound (68) with a suitable protective group. P means a protective group. Aldehyde (70) is obtained by treating compound (69) with sec-butyllithium and then allowing the treated compound to react with formamide such as N,N-dimethylformamide (DMF). Phenol (71) is obtained by fluorinating the compound with diethylamino sulfur trifluoride (DAST) and subsequently deprotecting the resulting material. The compound is converted into compound (1) by a technique in general synthetic organic chemistry.

A method for forming a dihydropyran ring is as described below. Compound (1) in which P is a divalent group represented by formula (pr-1), namely, compound (1a) will be described. Compound (s-6) is prepared from compound (s-1) according to the method described below. Objective compound (1a) is obtained by dehydrating compound (s-6) by heating compound (s-6) under reflux in toluene in the presence of p-toluenesulfonic acid monohydrate.

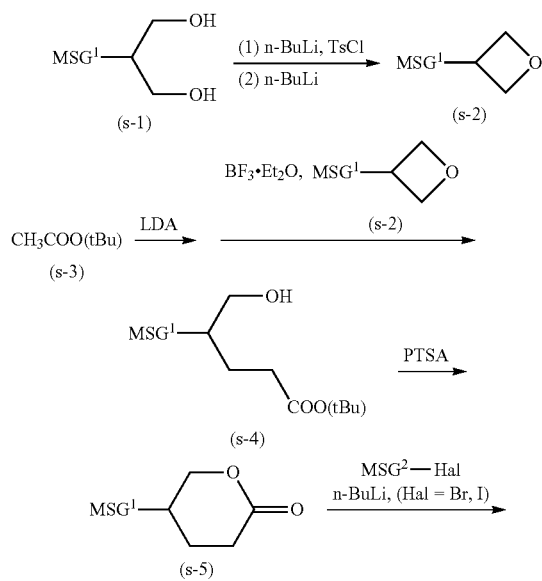

3. Liquid Crystal Composition

A composition of the invention is used mainly for a liquid crystal display device. The composition contains at least one of compound (1) as a first component. The composition may contain compounds (2) to (15) previously described. The composition may contain any other liquid crystal compound different from compounds (2) to (15). A preferred composition contains at least one of compound (1) as the first component, and at least one of compounds (2) to (4) as a second component. A third component is selected from compounds (5) to (15) based on a device mode (see Table 1). When the compound is used for a device having the mode such as the FFS mode and the PSA mode, compounds (5) to (7) are suitable as the third component. When the compound is used for a device having the mode such as the TN mode and the STN mode, compound (8) is suitable as the third component. When the compound is used for a device having the mode such as the VA mode and the PSA mode, compounds (9) to (15) are suitable as the third component. The composition may further contain a liquid crystal compound different from compounds (1) to (15). The composition may further contain an additive such as an optically active compound, an antioxidant, an ultraviolet light absorber, a light stabilizer, a heat stabilizer, an antifoaming agent, a polymerizable compound, a polymerization initiator and a polymerization inhibitor, when necessary.

TABLE 1

| Device mode and components of composition | | | |
|---|---|---|---|
| Device mode | FFS, PSA | TN, STN | VA, PSA |
| Δε of composition | Positively large | Positively large | Negatively large |
| First component | Compound (1) | Compound (1) | Compound (1) |
| Second component | Compounds (2) to (4) | Compounds (2) to (4) | Compounds (2) to (4) |
| Third component | Compounds (5) to (7) | Compound (8) | Compounds (9) to (15) |

The composition preferably contains at least one of compound (1) in the range of approximately 1% by weight to approximately 99% by weight in order to develop excellent characteristics. A further preferred ratio is in the range of approximately 3% by weight to approximately 90% by weight. Most preferred ratio is in the range of approximately 5% by weight to approximately 60% by weight.

Compounds (2) to (4) have alkyl or the like in two terminal groups, and the small dielectric anisotropy. Specific examples of preferred compounds include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine.

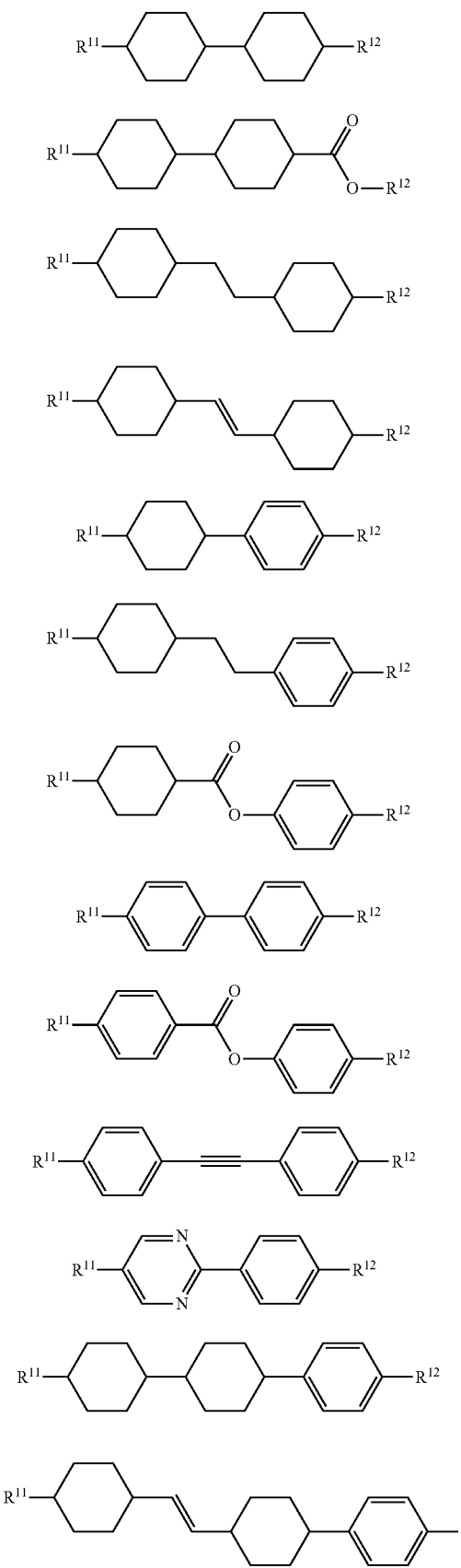
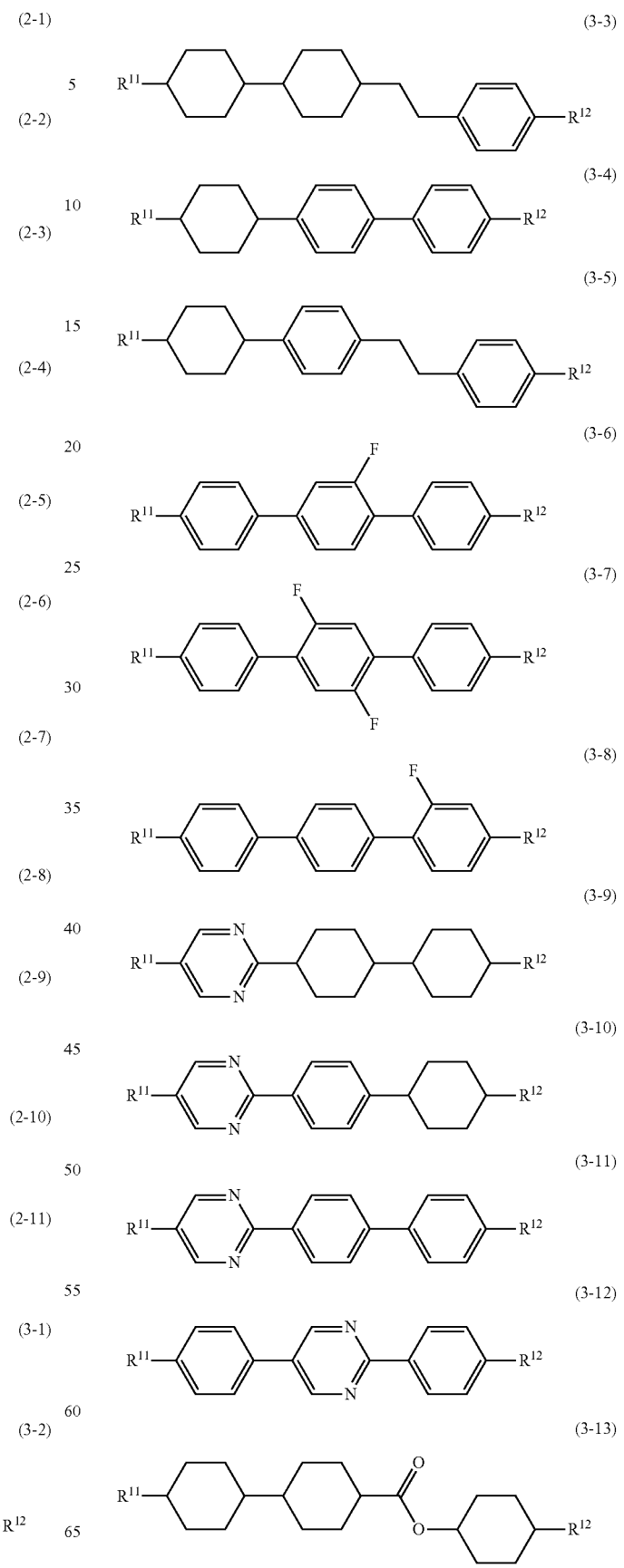

(3-14)
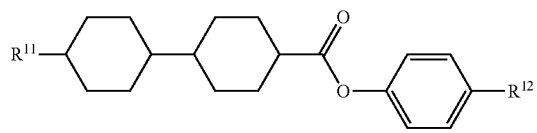

(3-15)
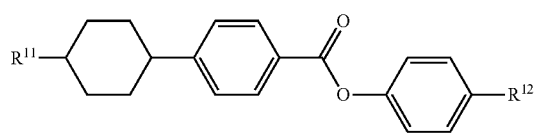

(3-16)
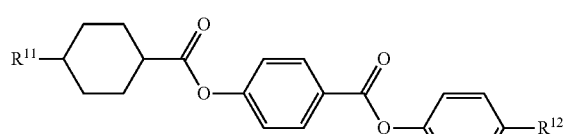

(3-17)
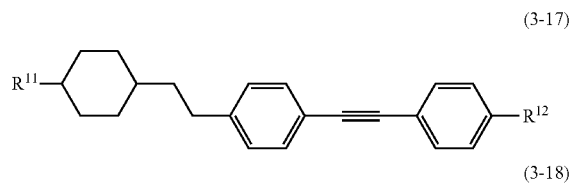

(3-18)
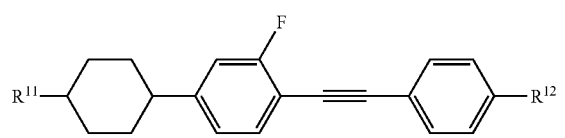

(3-19)
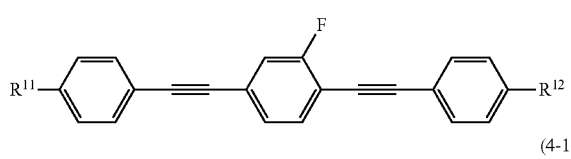

(4-1)
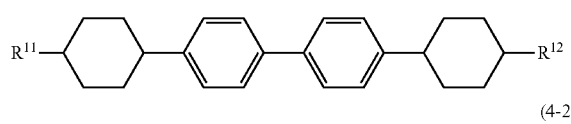

(4-2)
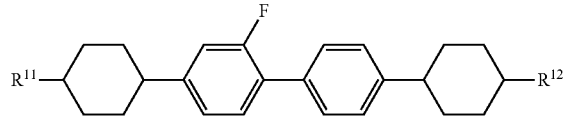

(4-3)
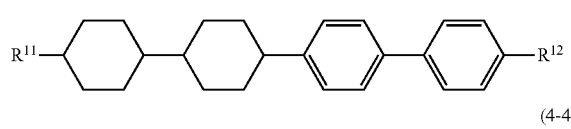

(4-4)
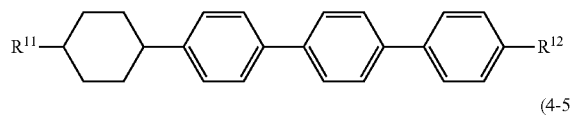

(4-5)
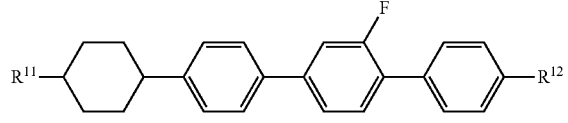

(4-6)
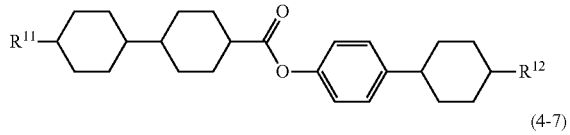

(4-7)
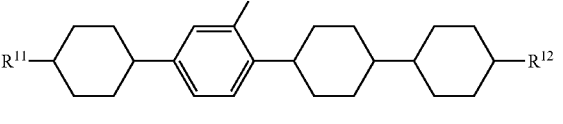

Compound (2) is effective mainly in decreasing the viscosity or adjusting the optical anisotropy. Compounds (3) and (4) are effective in extending the temperature range of the nematic phase by increasing the maximum temperature, or in adjusting the optical anisotropy.

Compounds (2) to (4) have the small dielectric anisotropy. As a content of compounds (2) to (4) increases, the viscosity of the composition decreases, but the dielectric anisotropy also decreases. Thus, as long as a desired value of threshold voltage of the device is met, the content is preferably as large as possible. Therefore, when a composition for the IPS mode, the VA mode or the like is prepared, a content of compounds (2) to (4) is preferably approximately 30% by weight or more, and further preferably approximately 40% by weight or more, based on the weight of the liquid crystal composition.

Compounds (5) to (7) have a halogen-containing group or a fluorine-containing group at a right terminal. Specific examples of preferred compounds include compounds (5-1) to (5-16), compounds (6-1) to (6-113) and compounds (7-1) to (7-57). In the compounds, $R^{13}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine; and $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$.

(5-1)
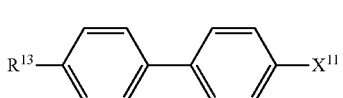

(5-2)
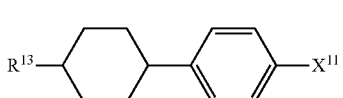

(5-3)

(5-4)
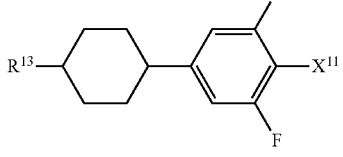

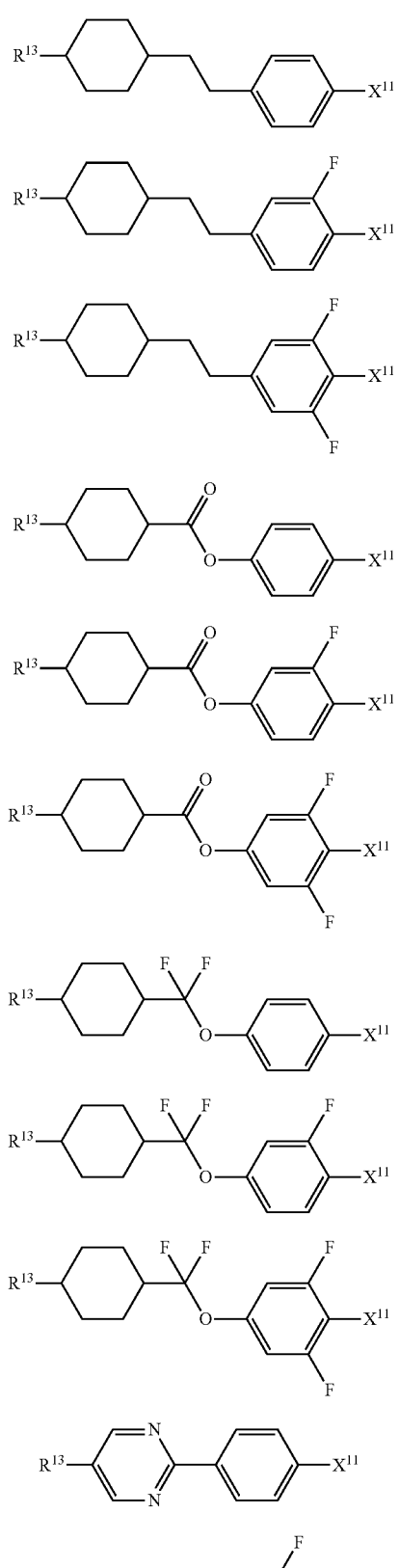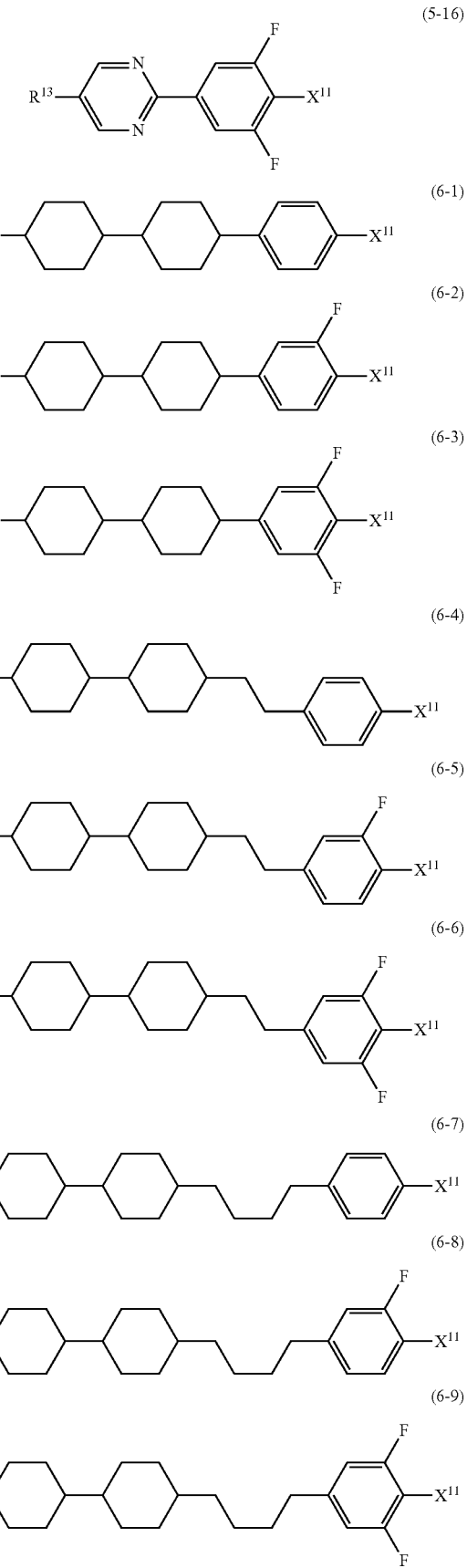

(6-10) 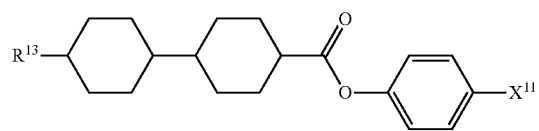
(6-11) 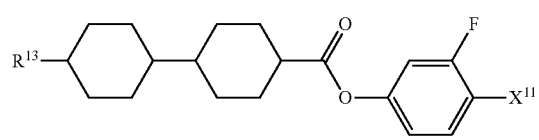
(6-12) 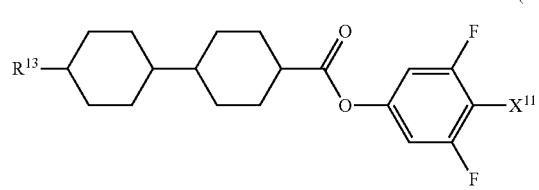
(6-13) 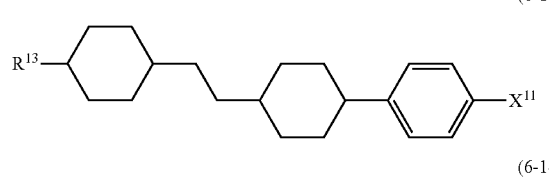
(6-14) 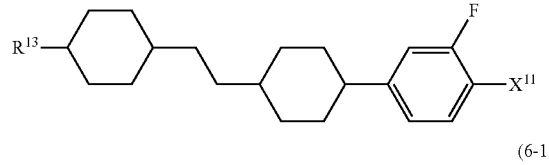
(6-15) 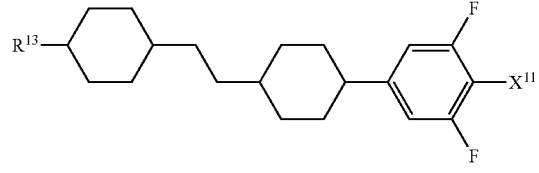
(6-16) 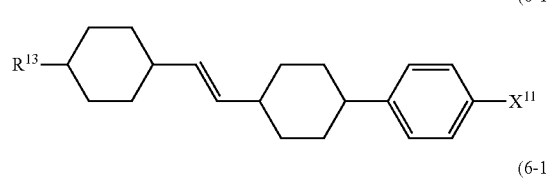
(6-17) 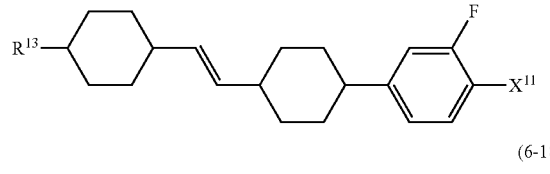
(6-18) 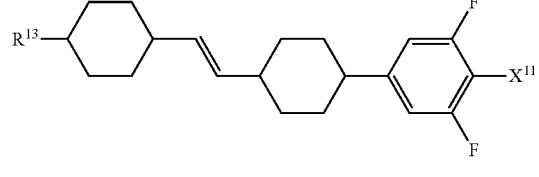
(6-19) 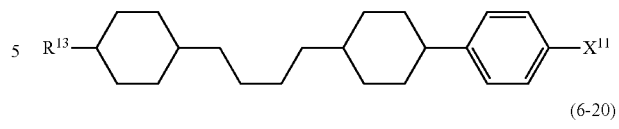
(6-20) 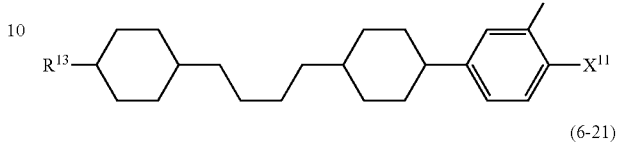
(6-21) 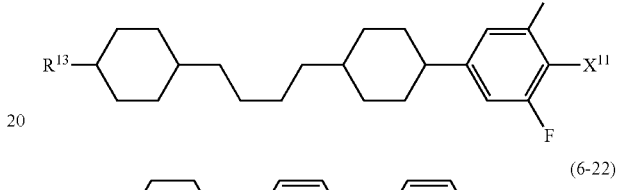
(6-22) 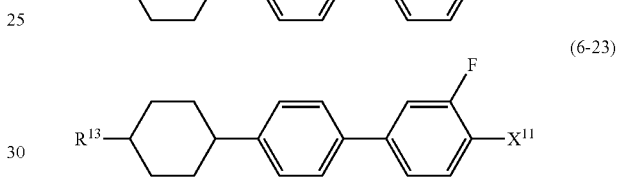
(6-23) 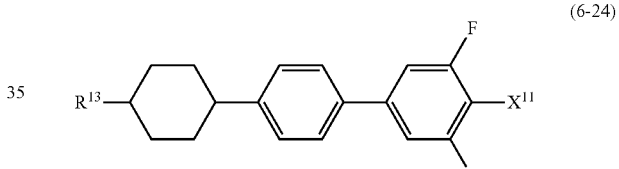
(6-24) 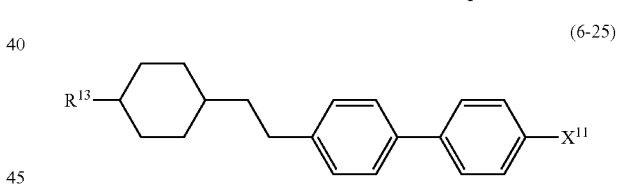
(6-25) 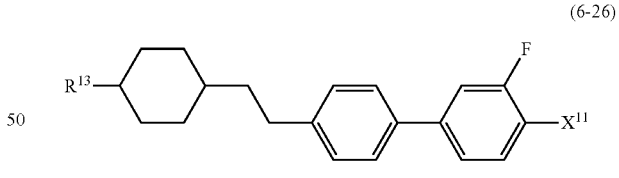
(6-26) 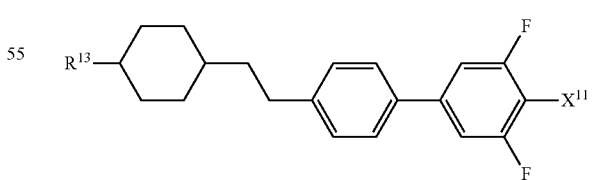
(6-27) 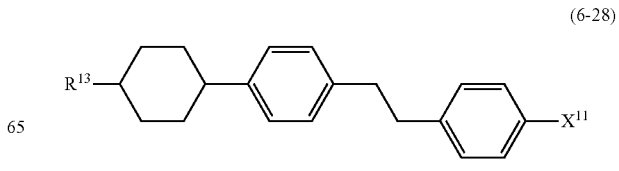
(6-28)

(6-29) 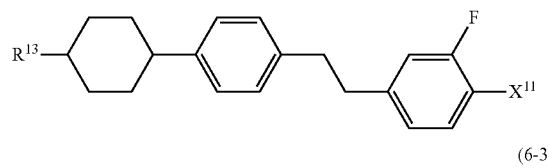
(6-30) 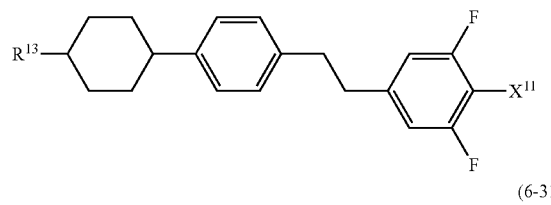
(6-31) 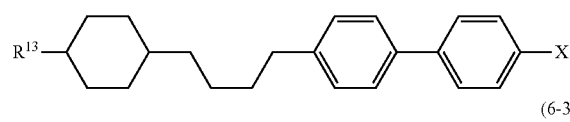
(6-32) 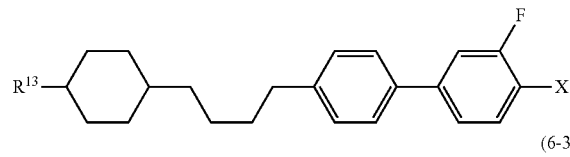
(6-33) 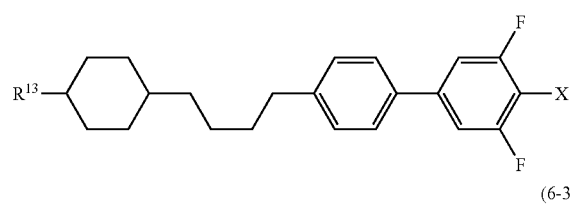
(6-34) 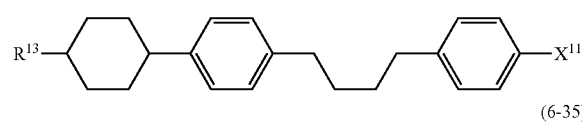
(6-35) 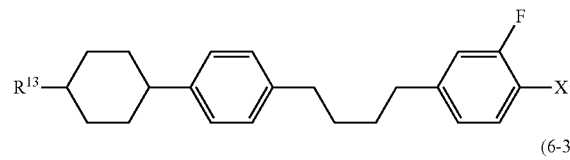
(6-36) 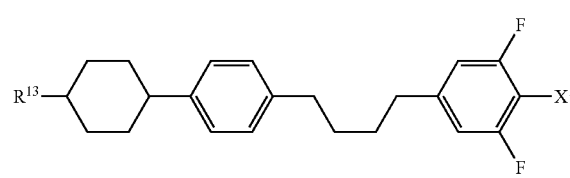
(6-37) 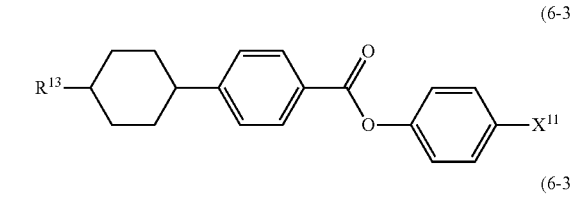
(6-38) 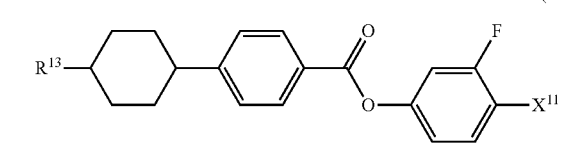
(6-39) 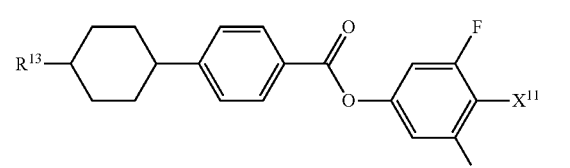
(6-40) 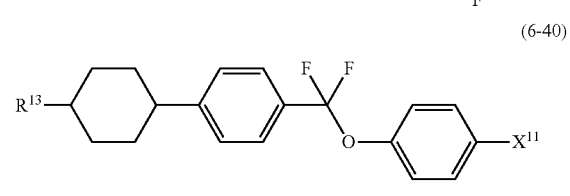
(6-41) 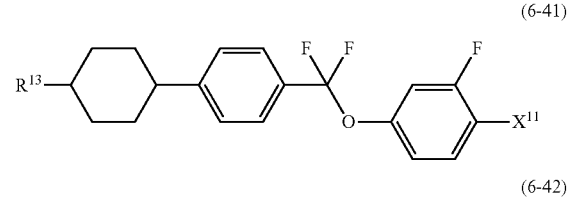
(6-42) 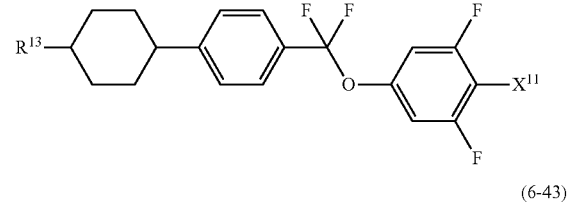
(6-43) 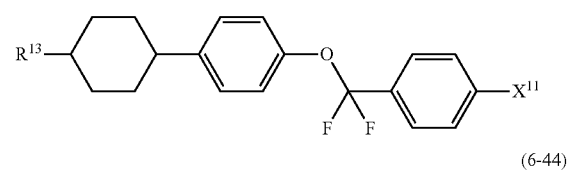
(6-44) 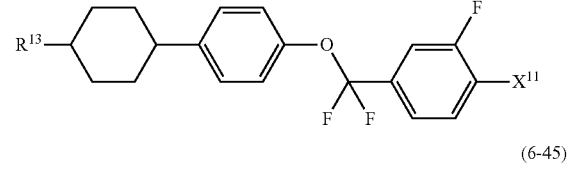
(6-45) 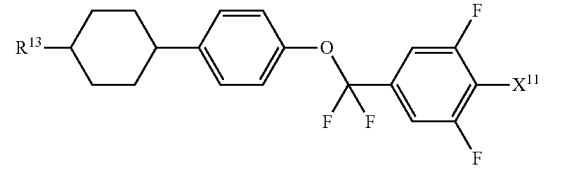
(6-46) 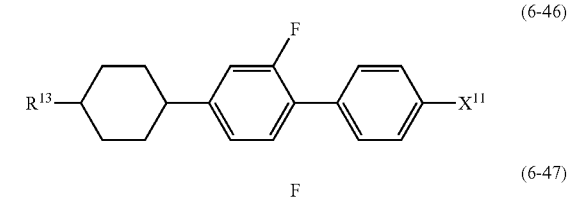
(6-47) 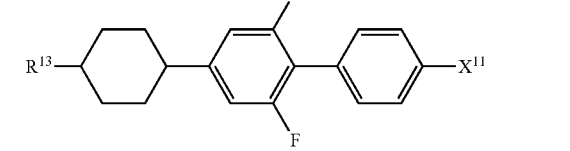

(6-48) 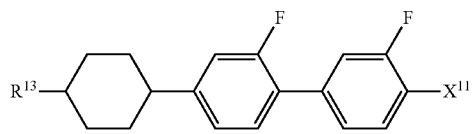
(6-49) 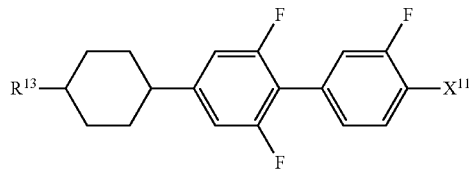
(6-50) 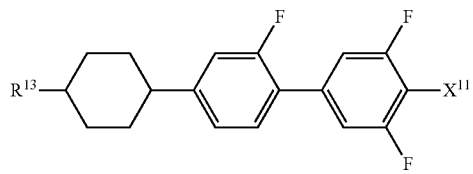
(6-51) 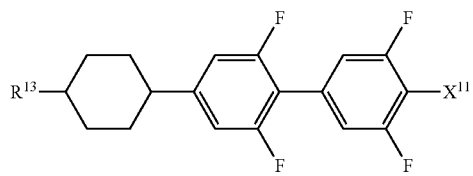
(6-52) 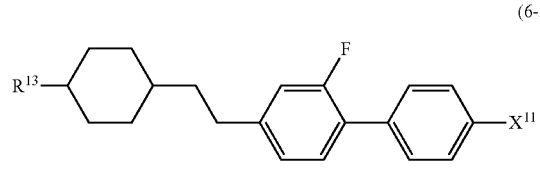
(6-53) 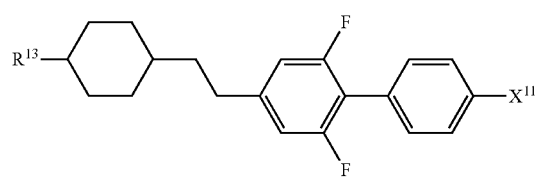
(6-54) 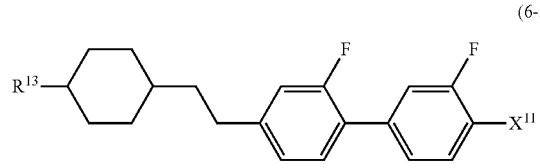
(6-55) 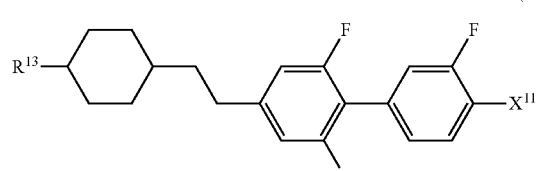
(6-56) 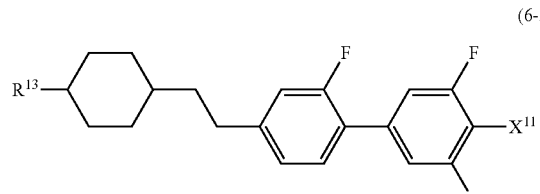
(6-57) 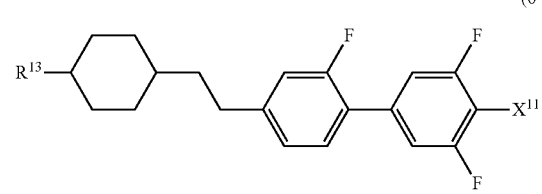
(6-58) 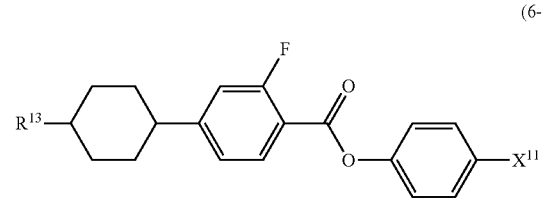
(6-59) 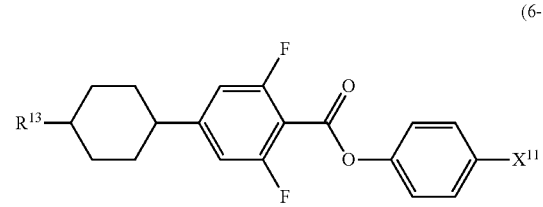
(6-60) 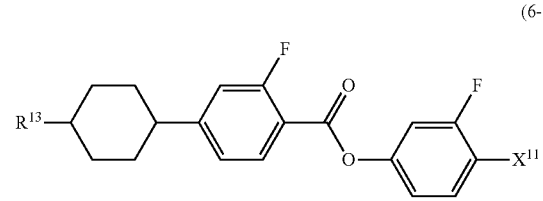
(6-61) 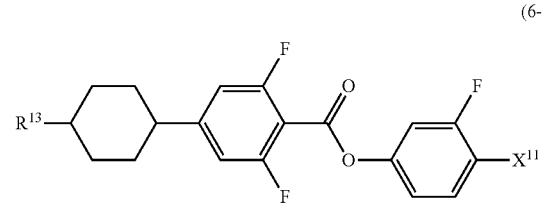
(6-62) 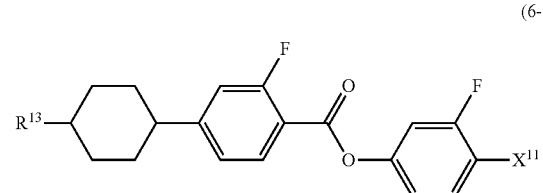
(6-63) 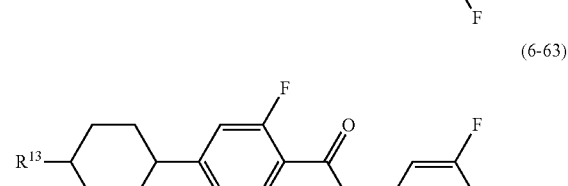
(6-64) 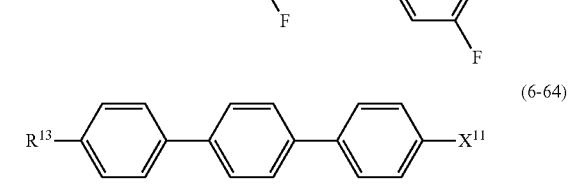

(6-65) 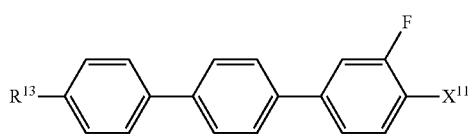
(6-66) 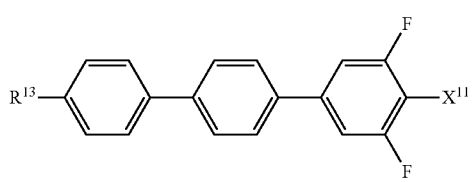
(6-67) 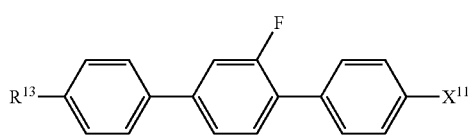
(6-68) 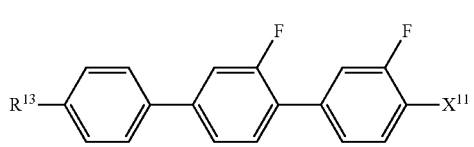
(6-69) 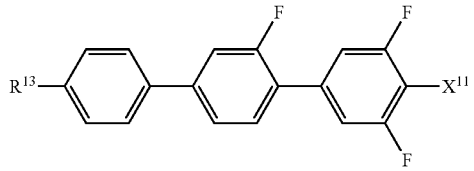
(6-70) 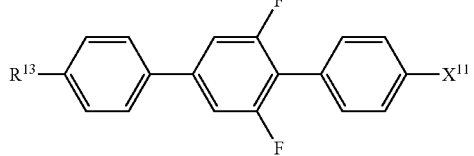
(6-71) 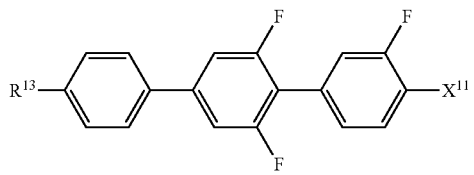
(6-72) 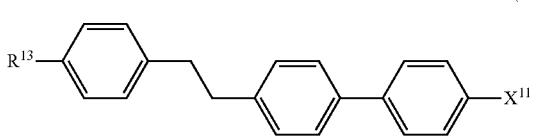
(6-73) 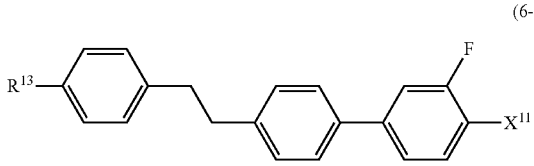
(6-74) 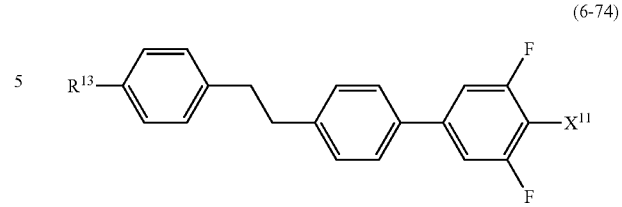
(6-75) 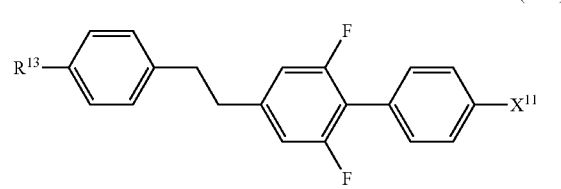
(6-76) 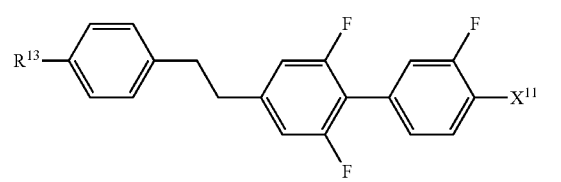
(6-77) 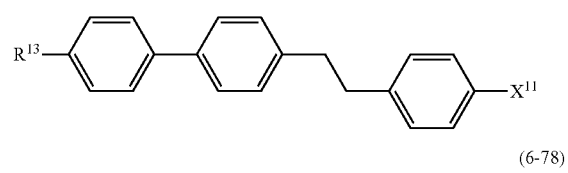
(6-78) 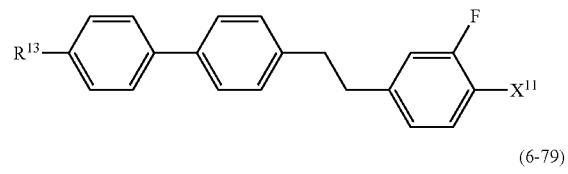
(6-79) 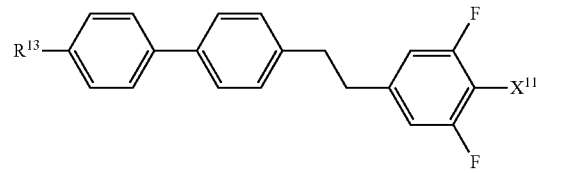
(6-80) 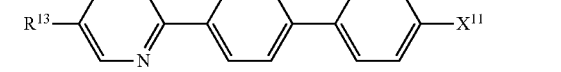
(6-81) 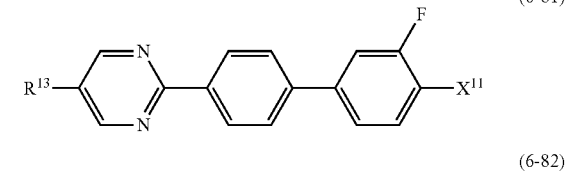
(6-82) 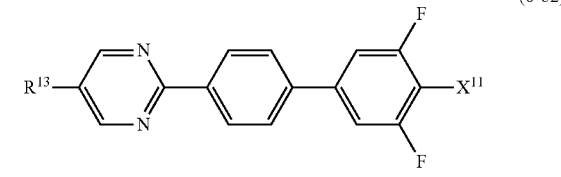

(6-83) 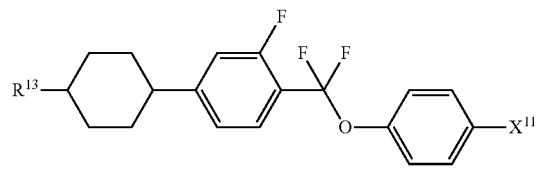
(6-84) 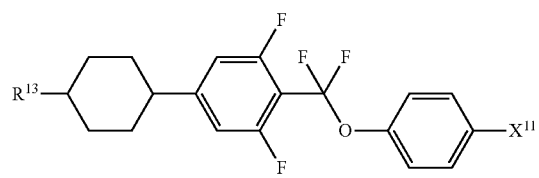
(6-85) 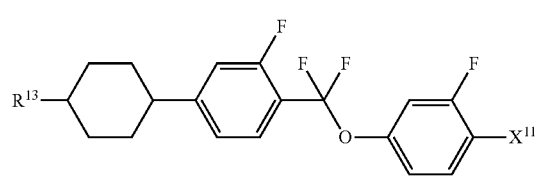
(6-86) 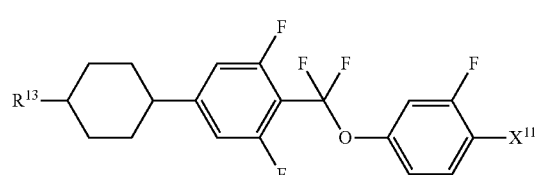
(6-87) 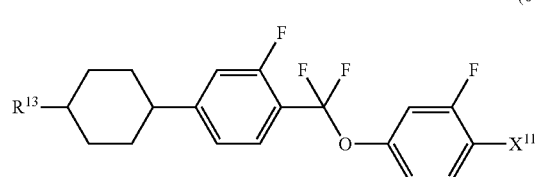
(6-88) 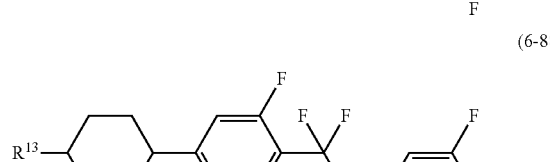
(6-89) 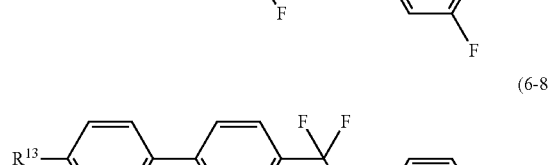
(6-90) 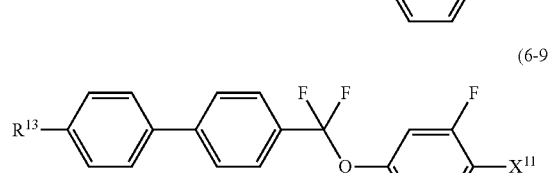
(6-91) 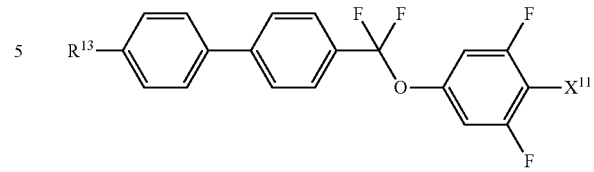
(6-92) 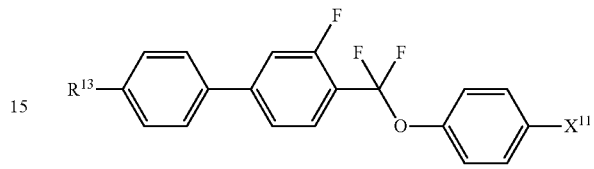
(6-93) 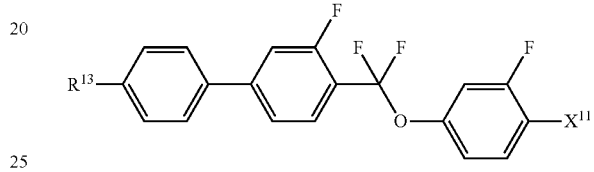
(6-94) 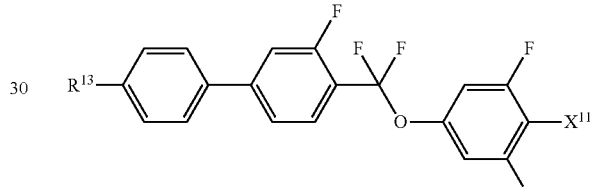
(6-95) 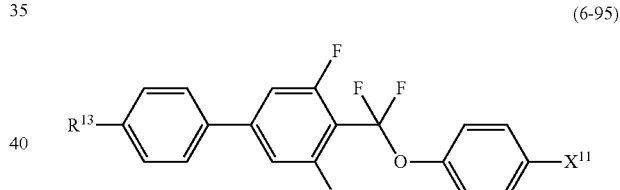
(6-96) 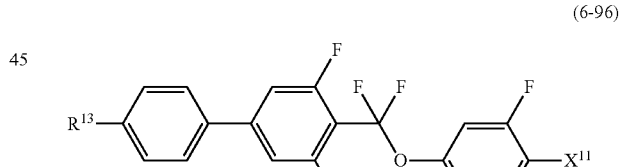
(6-97) 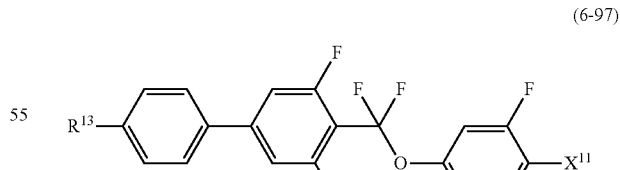
(6-98) 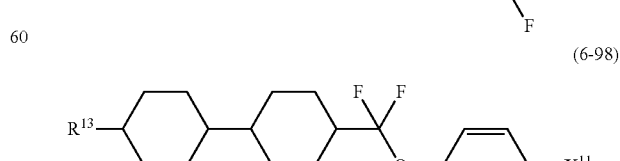

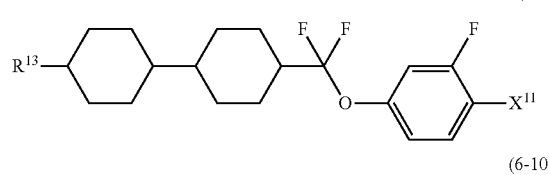 (6-99)
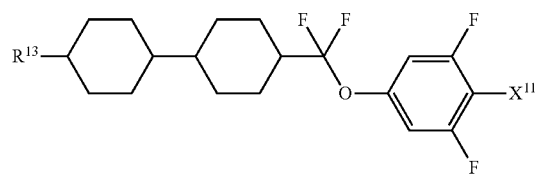 (6-100)
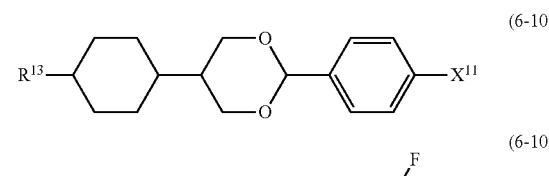 (6-101)
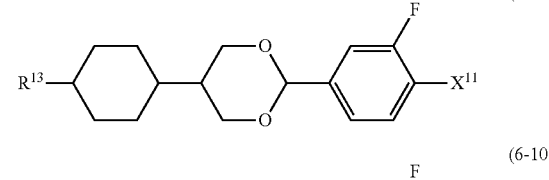 (6-102)
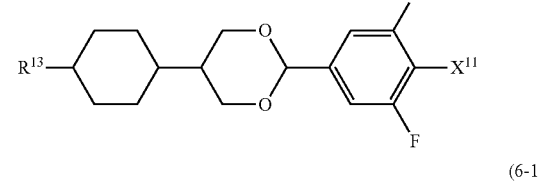 (6-103)
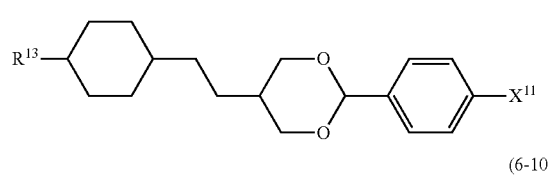 (6-104)
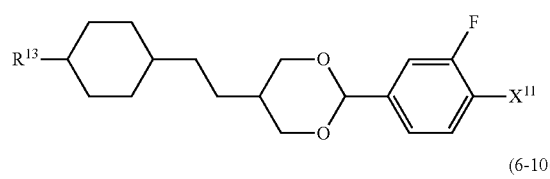 (6-105)
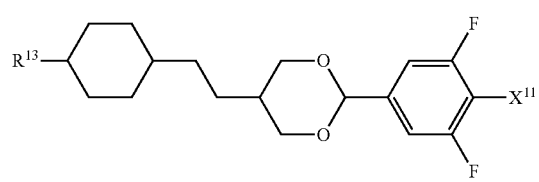 (6-106)
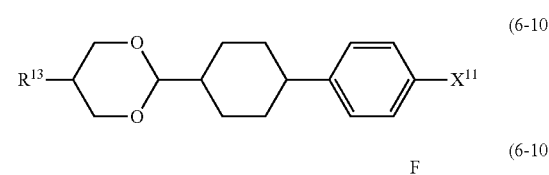 (6-107)
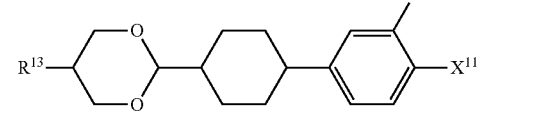 (6-108)
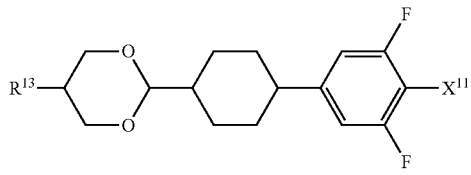 (6-109)
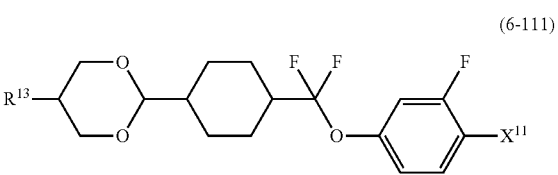 (6-110)
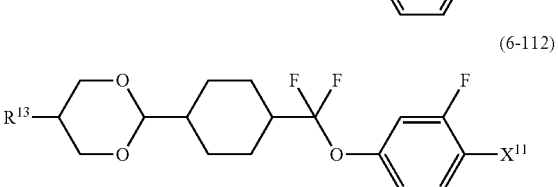 (6-111)
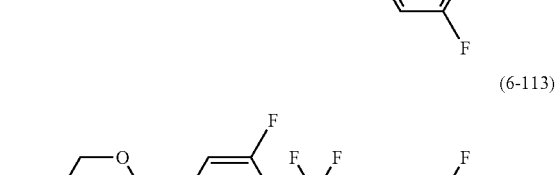 (6-112)
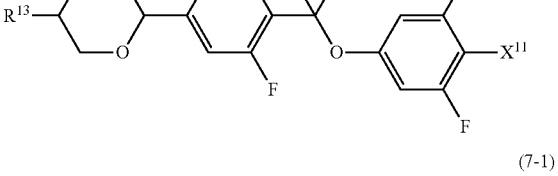 (6-113)
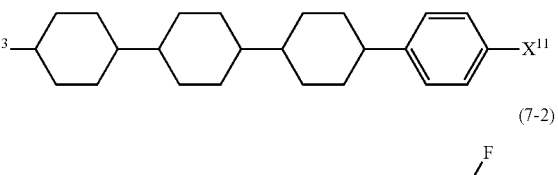 (7-1)
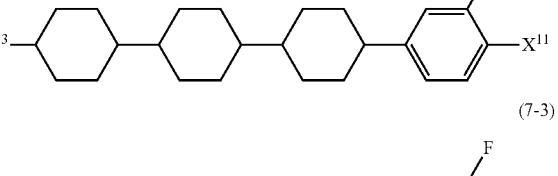 (7-2)
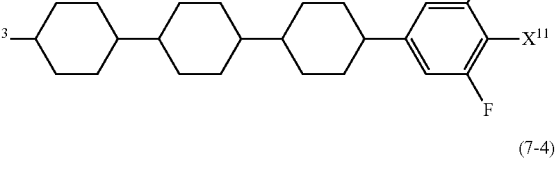 (7-3)
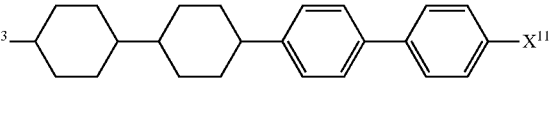 (7-4)

(7-5) 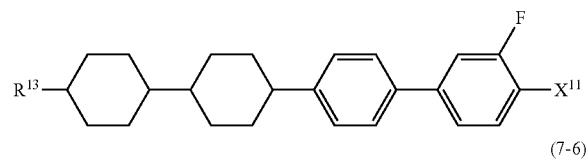
(7-6) 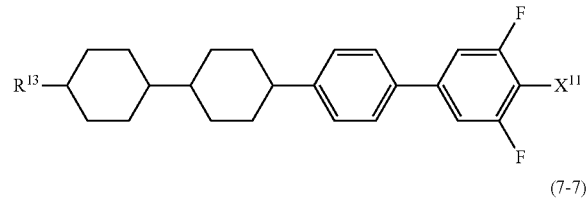
(7-7) 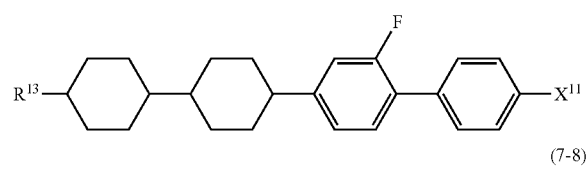
(7-8) 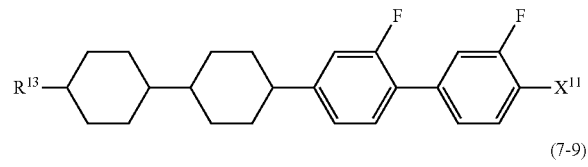
(7-9) 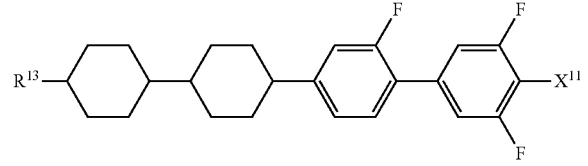
(7-10) 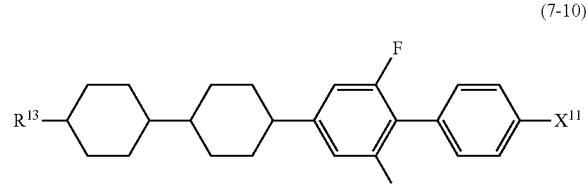
(7-11) 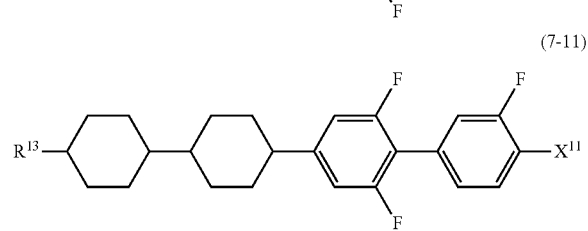
(7-12) 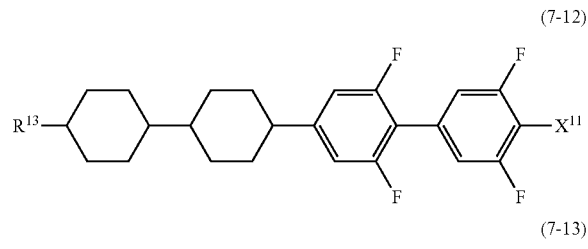
(7-13) 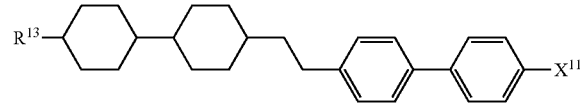
(7-14) 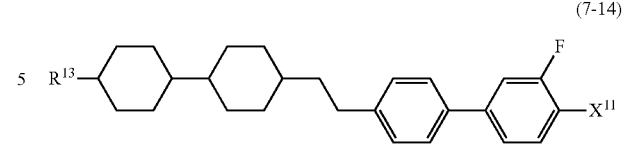
(7-15) 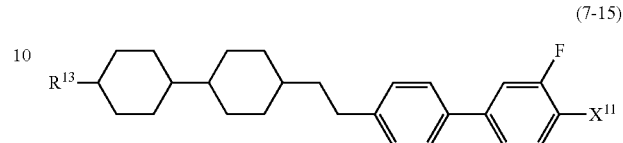
(7-16) 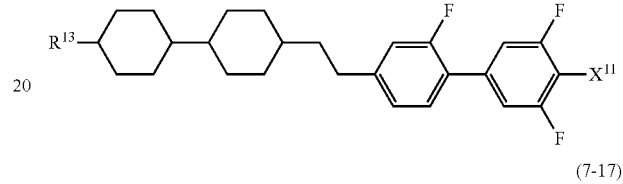
(7-17) 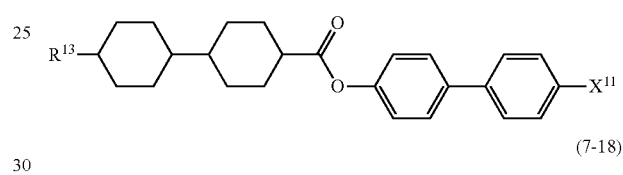
(7-18) 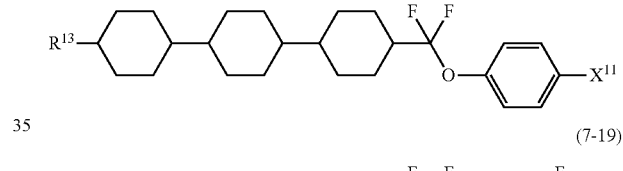
(7-19) 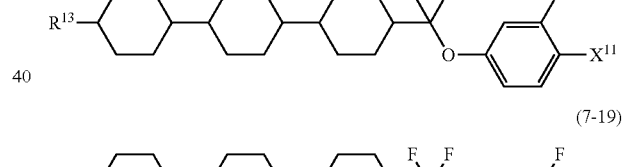
(7-19) 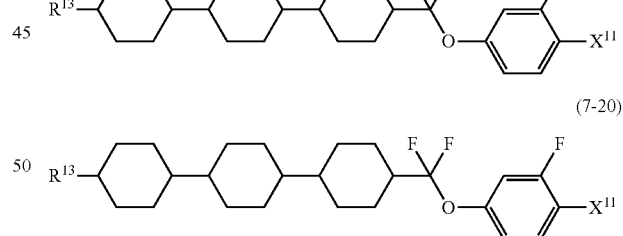
(7-20) 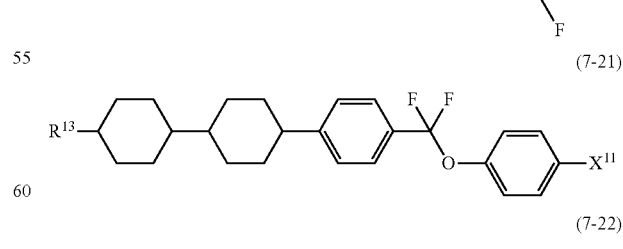
(7-21) 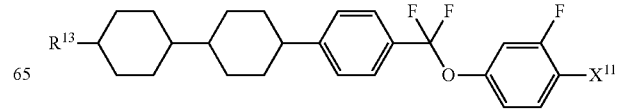
(7-22)

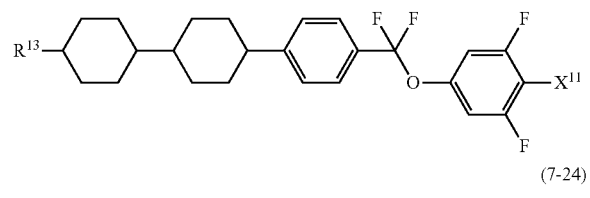
(7-23)
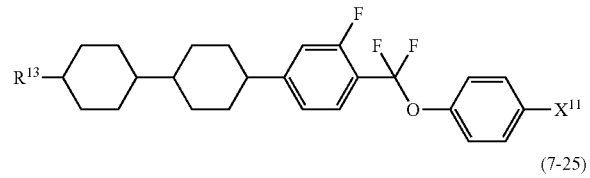
(7-24)
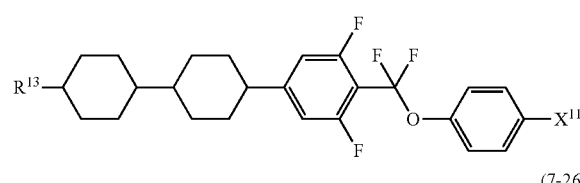
(7-25)
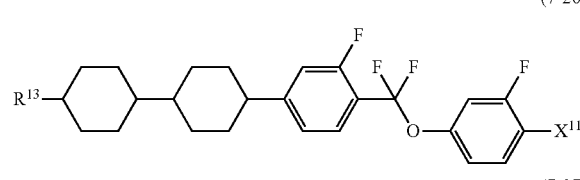
(7-26)
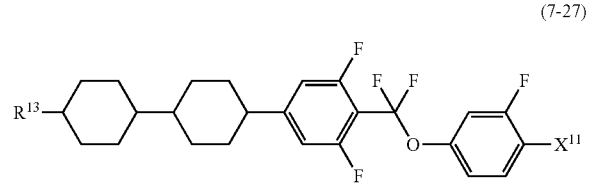
(7-27)
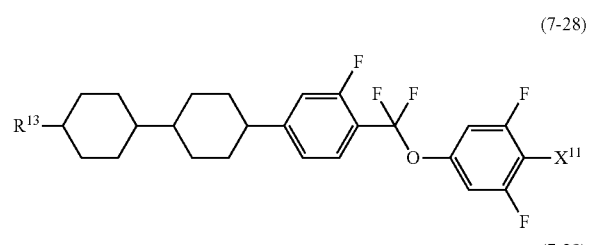
(7-28)
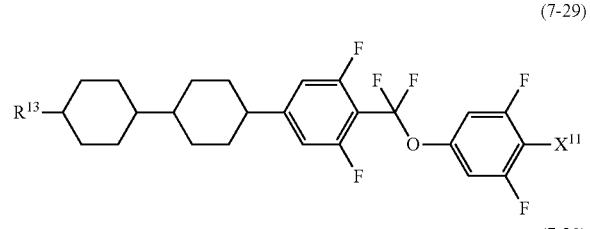
(7-29)
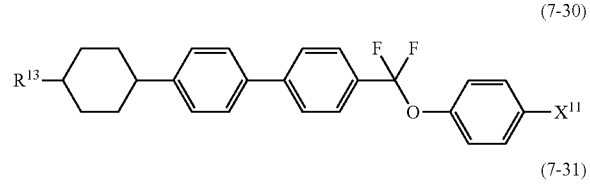
(7-30)
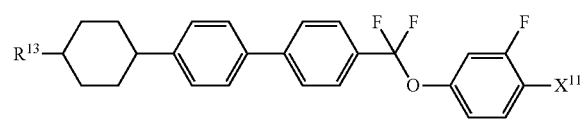
(7-31)
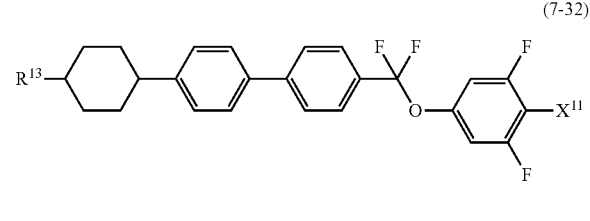
(7-32)
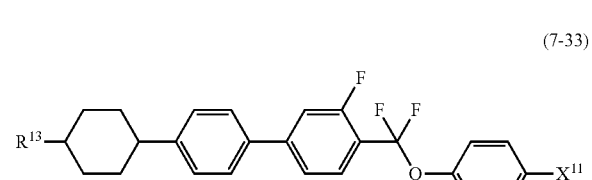
(7-33)
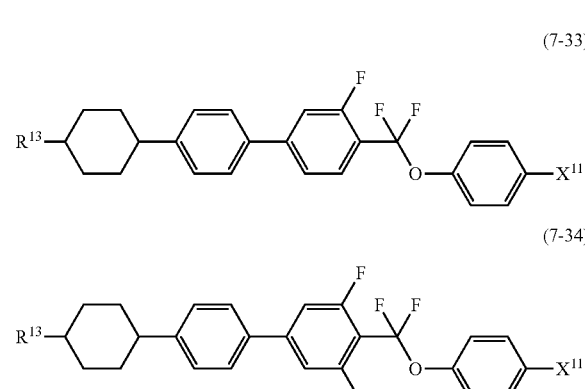
(7-34)
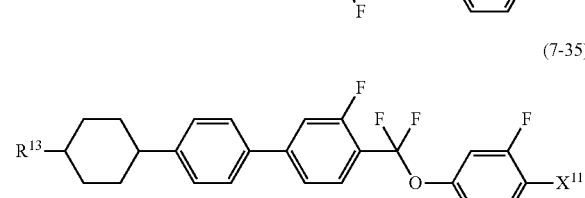
(7-35)
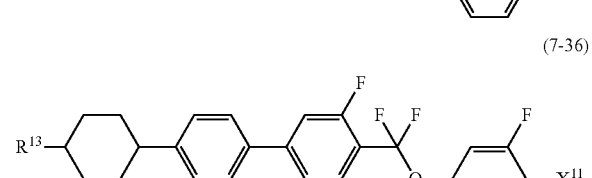
(7-36)
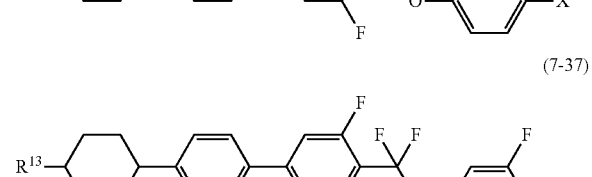
(7-37)
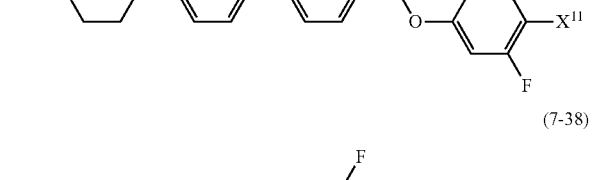
(7-38)
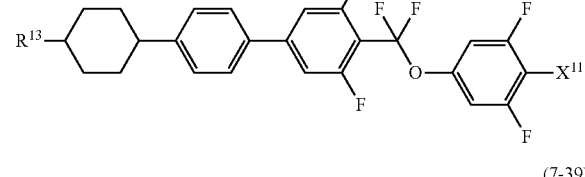
(7-39)
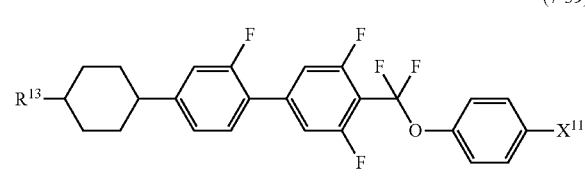

(7-40) 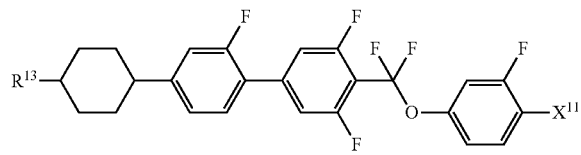
(7-41) 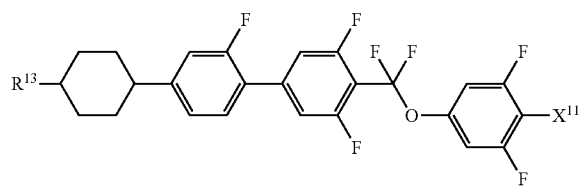
(7-42) 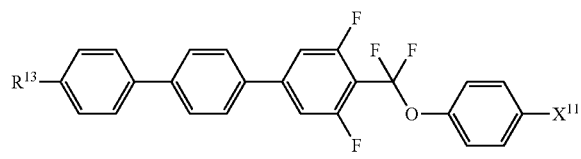
(7-43) 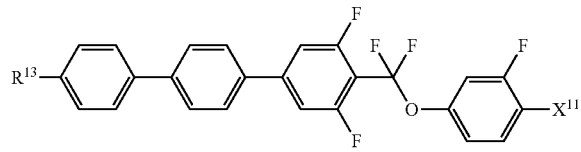
(7-44) 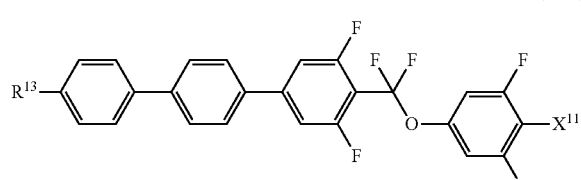
(7-45) 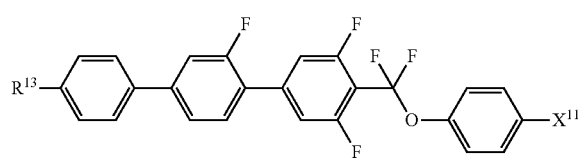
(7-46) 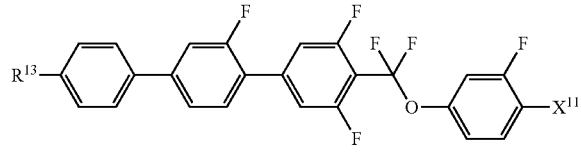
(7-47) 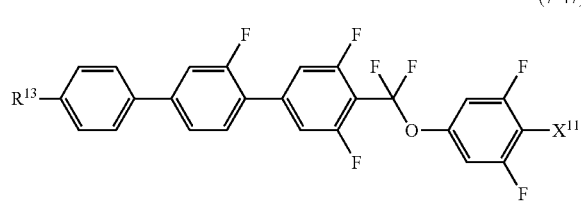
(7-48) 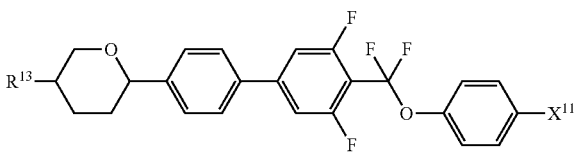
(7-49) 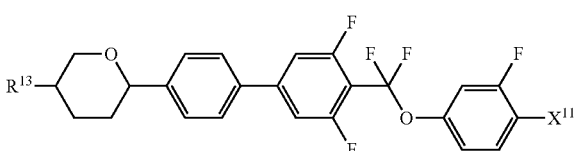
(7-50) 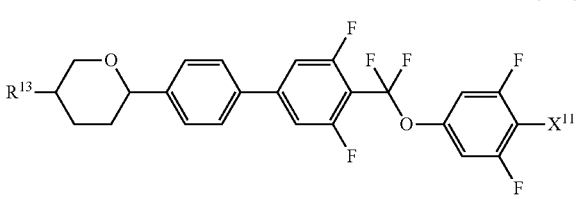
(7-51) 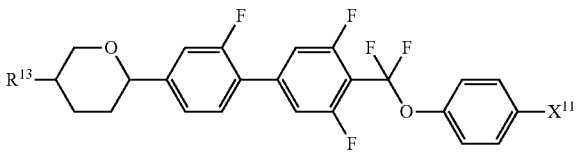
(7-52) 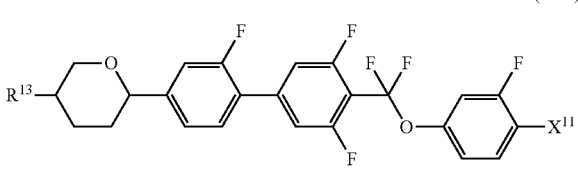
(7-53) 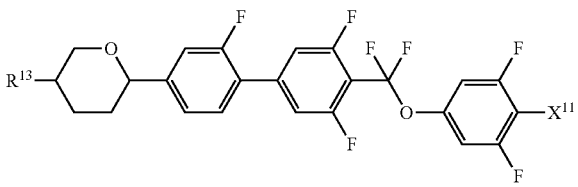
(7-54) 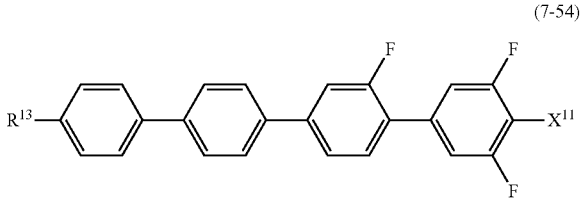
(7-55) 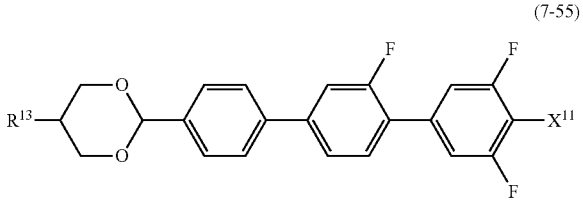

(7-56)
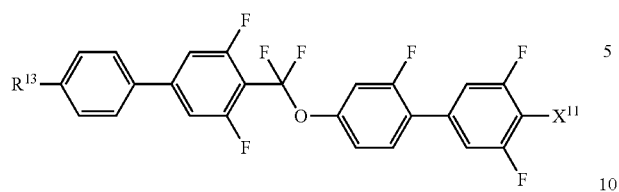

(7-57)
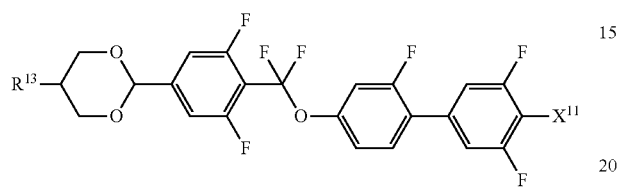

Compounds (5) to (7) have the large positive dielectric anisotropy and a superb stability to heat, light and so forth, and therefore are used for preparing a composition for the mode such as the IPS mode, the FFS mode and the OCB mode. A content of compounds (5) to (7) is suitably in the range of approximately 1% by weight to approximately 99% by weight, preferably in the range of approximately 10% by weight to approximately 97% by weight, and further preferably in the range of approximately 40% by weight to approximately 95% by weight, based on the weight of the liquid crystal composition. When the compounds are added to a composition having the negative dielectric anisotropy, a content of the compounds is preferably approximately 30% by weight or less based on the weight of the liquid crystal composition. When compounds (5) to (7) is added thereto, an elastic constant of the composition and a voltage-transmittance curve of the device can be adjusted.

Compound (8) has —C≡N or —C≡C—C≡N as a right terminal group. Specific examples of preferred compounds include compounds (8-1) to (8-64). In the compounds, $R^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine; and $X^{12}$ is —C≡N or —C≡C—C≡N.

(8-1)
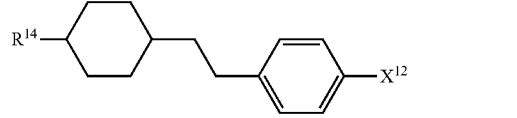

(8-2)

(8-3)

(8-4)
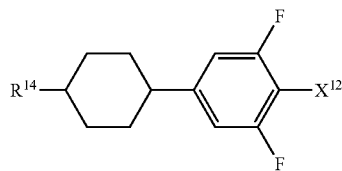

(8-5)
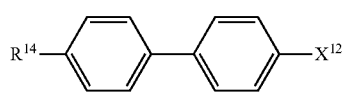

(8-6)

(8-7)
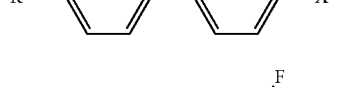

(8-8)
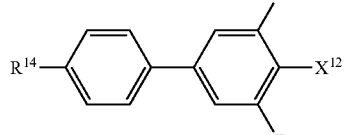

(8-9)
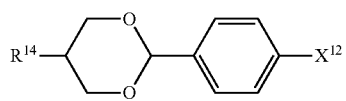

(8-10)
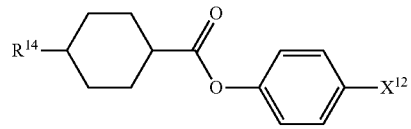

(8-11)
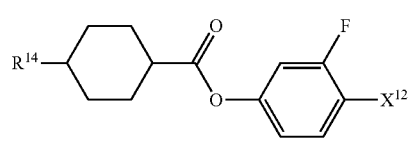

(8-12)
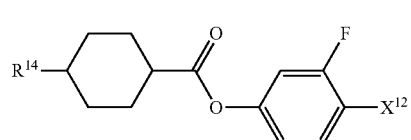

(8-13)
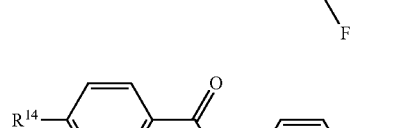

(8-14)
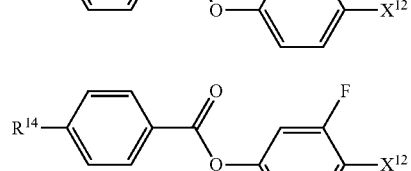

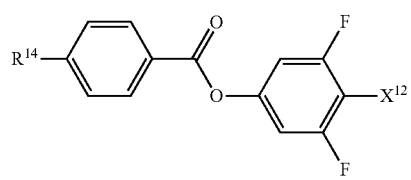
(8-15)
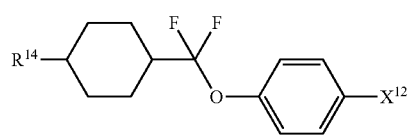
(8-16)
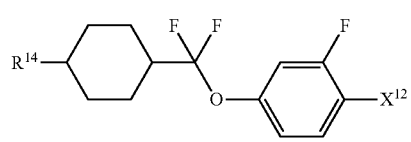
(8-17)
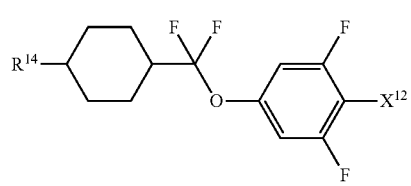
(8-18)
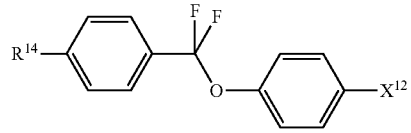
(8-19)
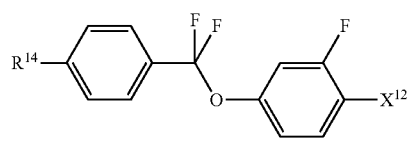
(8-20)
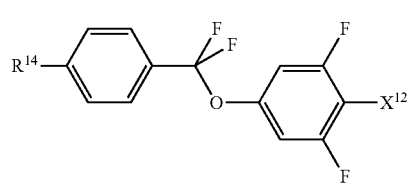
(8-21)
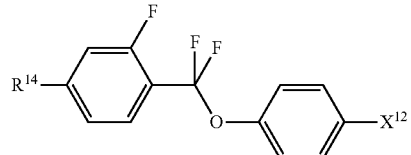
(8-22)
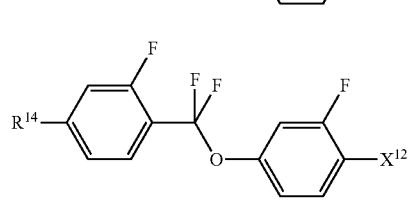
(8-23)
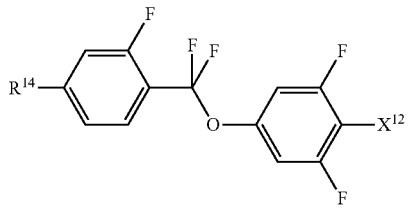
(8-24)
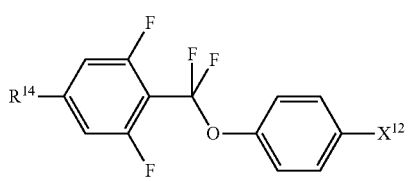
(8-25)
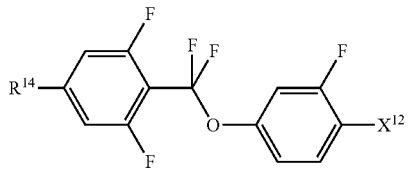
(8-26)
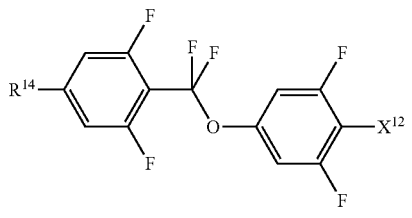
(8-27)
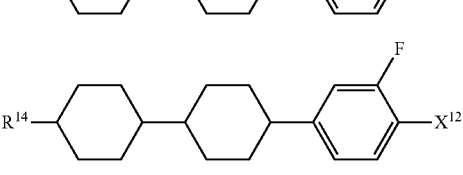
(8-28)
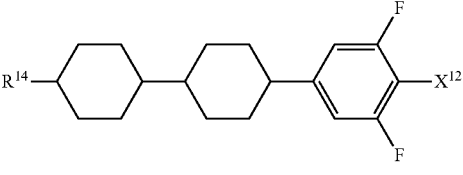
(8-29)
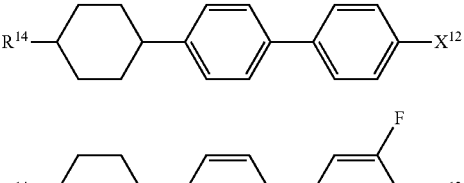
(8-30)
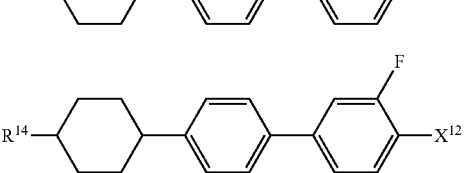
(8-31)
(8-32)
(8-33)

(8-34) 
(8-35) 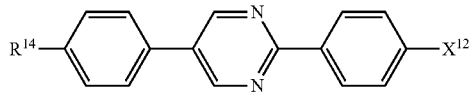
(8-36) 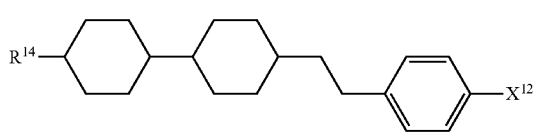
(8-37) 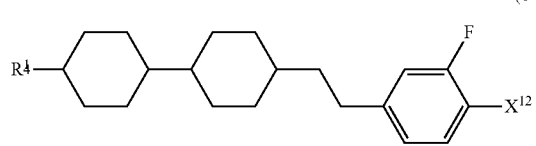
(8-38) 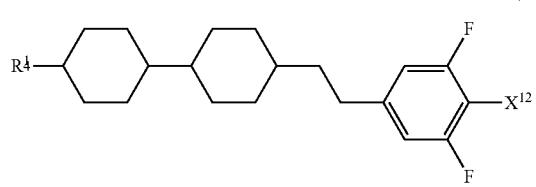
(8-39) 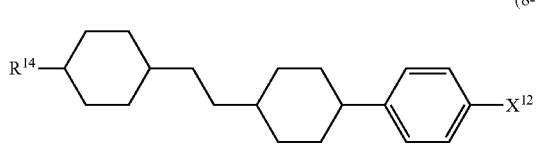
(8-40) 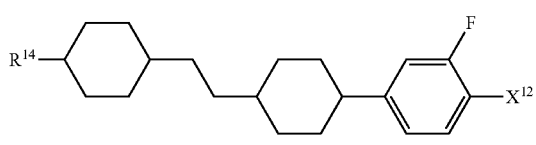
(8-41) 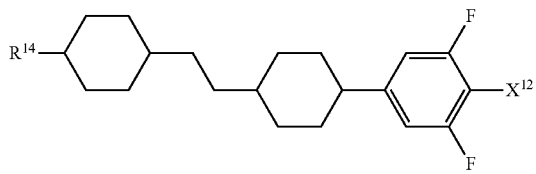
(8-42) 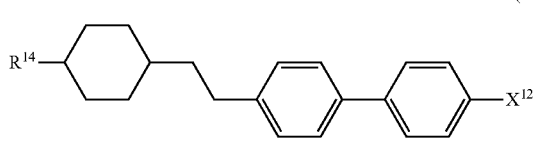
(8-43) 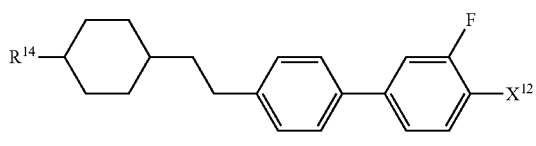
(8-44) 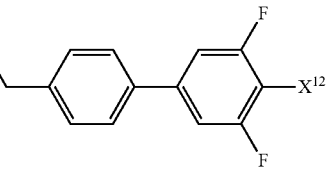
(8-45) 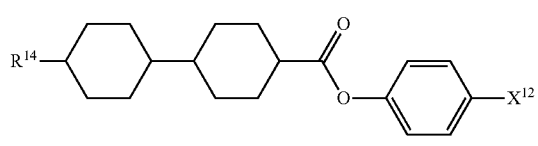
(8-46) 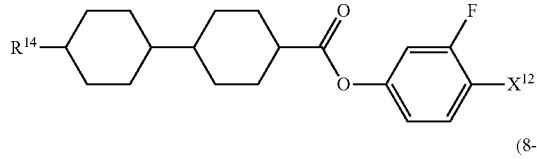
(8-47) 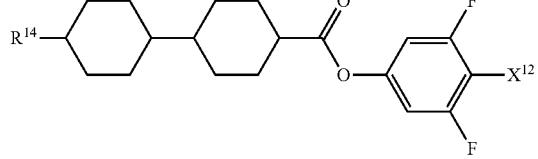
(8-48) 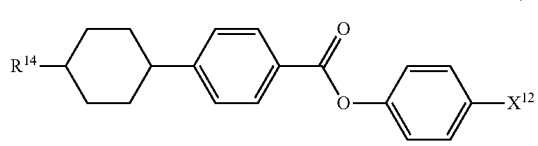
(8-49) 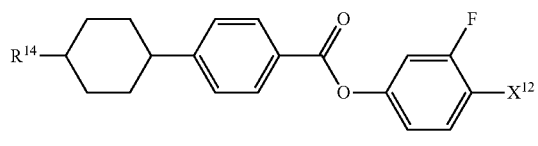
(8-50) 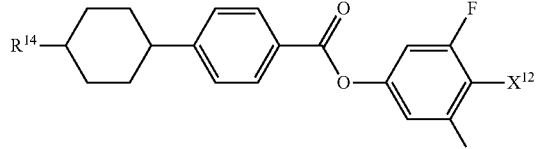
(8-51) 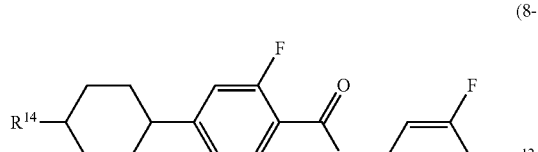
(8-52) 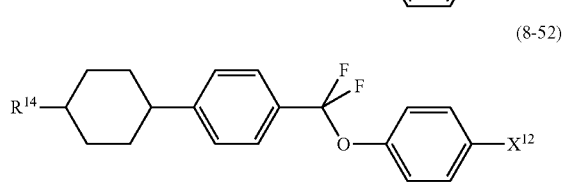

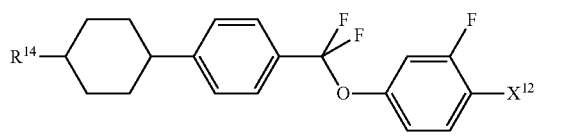 (8-53)

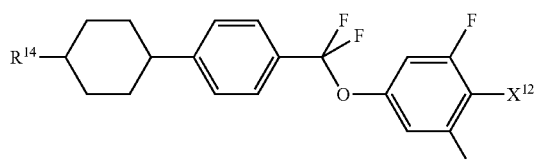 (8-54)

(8-55)

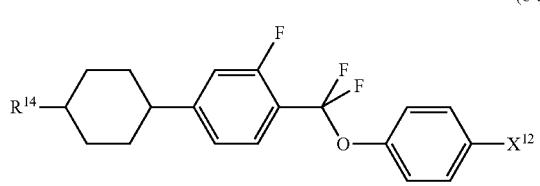 (8-56)

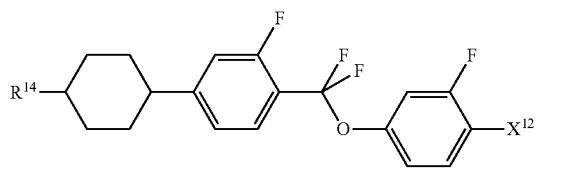 (8-57)

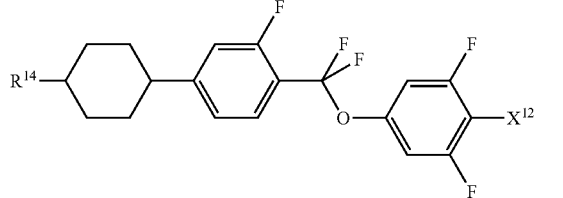 (8-58)

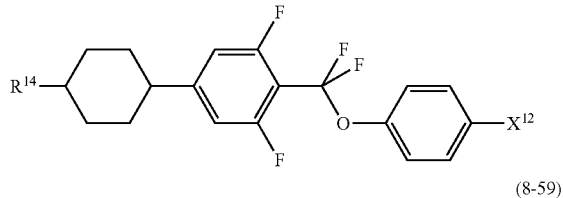 (8-59)

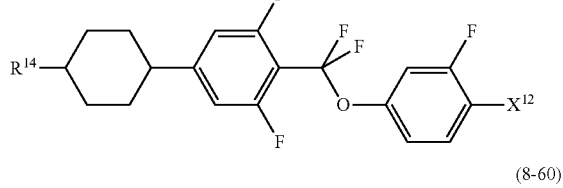 (8-60)

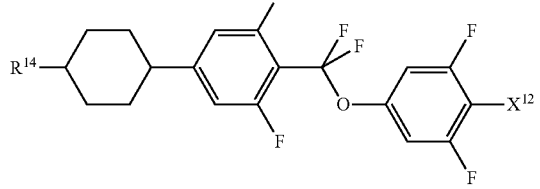

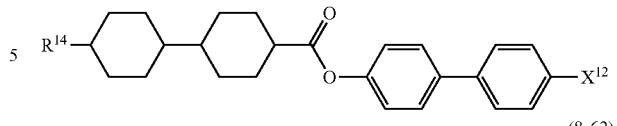 (8-61)

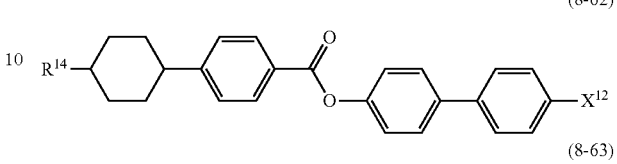 (8-62)

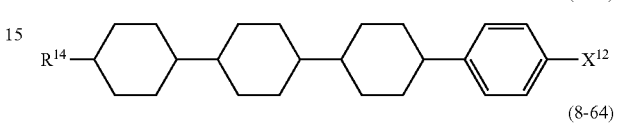 (8-63)

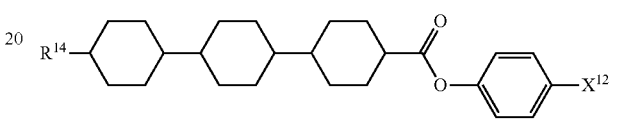 (8-64)

Compound (8) has the positive dielectric anisotropy a value of which is large, and therefore is mainly used for preparing a composition for the mode such as the TN mode and the STN mode. The dielectric anisotropy of the composition can be increased by adding compound (8) thereto. Compound (8) is effective in extending the temperature range of the liquid crystal phase, adjusting the viscosity or adjusting the optical anisotropy. The compound is also useful for adjusting the voltage-transmittance curve of the device.

When a composition for the TN mode, the STN mode or the like is prepared, a content of compound (8) is suitably in the range of approximately 1% by weight to approximately 99% by weight, preferably in the range of approximately 10% by weight to approximately 97% by weight, and further preferably in the range of approximately 40% by weight to approximately 95% by weight, based on the weight of the liquid crystal composition. When compound (8) is added to the composition having the negative dielectric anisotropy, a content of the compound is preferably approximately 30% by weight or less based on the weight of the liquid crystal composition. When compound (8) is added thereto, the elastic constant of the composition and the voltage-transmittance curve of the device can be adjusted.

Compounds (9) to (15) have phenylene in which hydrogen in a lateral position are replaced by two halogen atoms, such as 2,3-difluoro-1,4-phenylene. Specific examples of preferred compounds include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds, $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, at least one of hydrogen may be replaced by fluorine; and $R^{17}$ is hydrogen, fluorine, alkyl having 1 to 10 carbons or alkenyl having 2 to 10 carbons, and in the alkyl and the alkenyl, at least one of —$CH_2$— may be replaced by —O—, at least one of hydrogen may be replaced by fluorine.

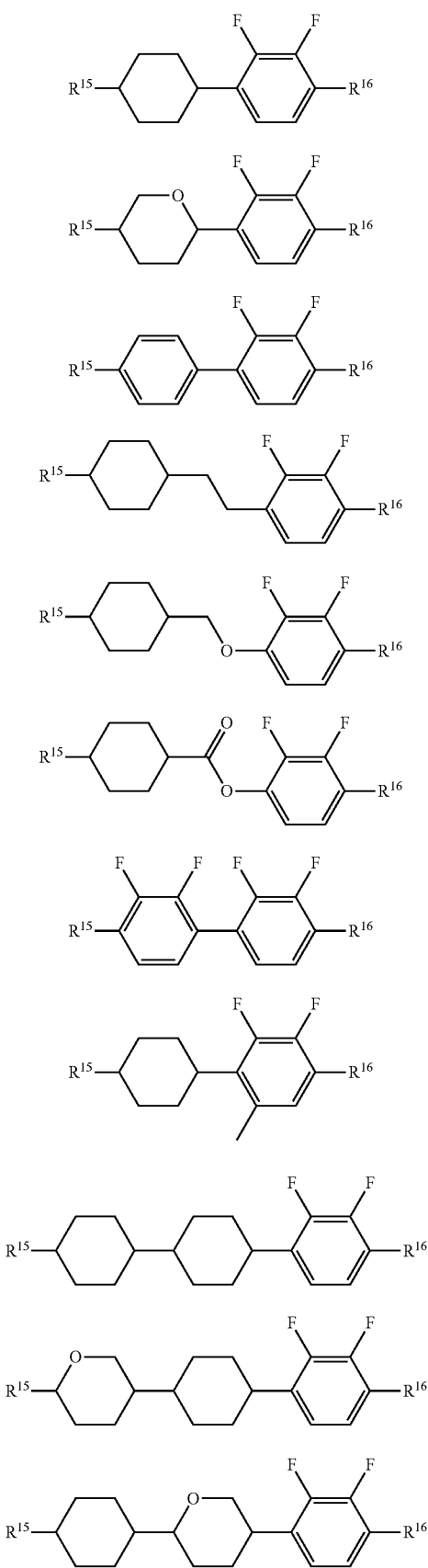
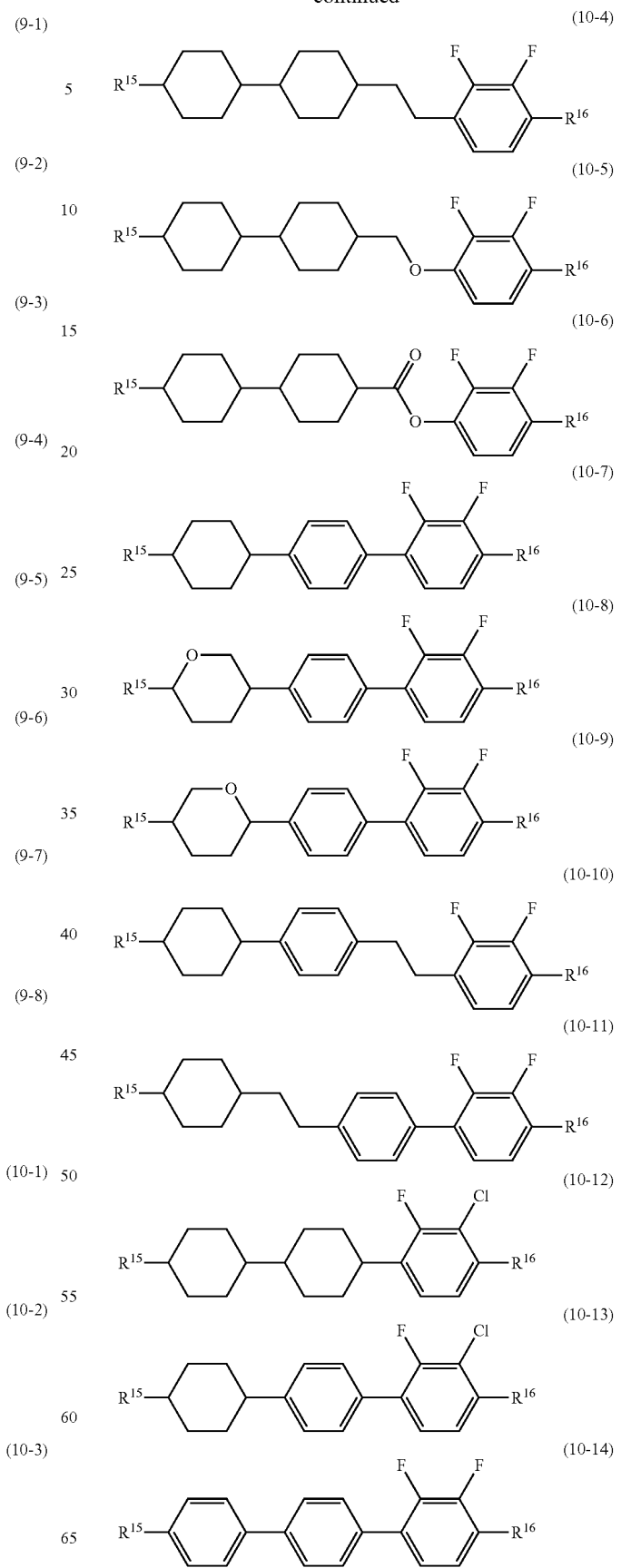

(10-15)
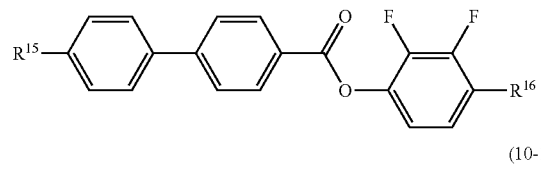
(10-16)
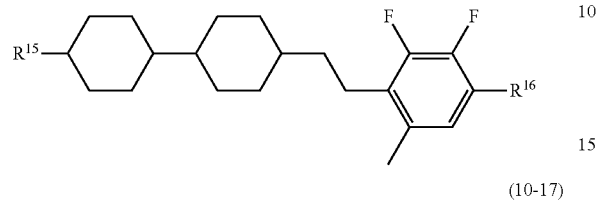
(10-17)
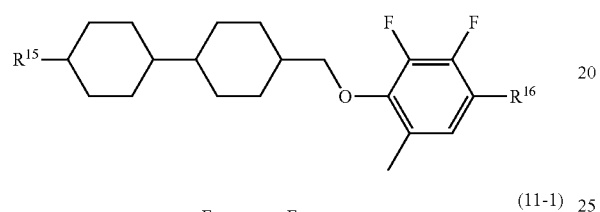
(11-1)
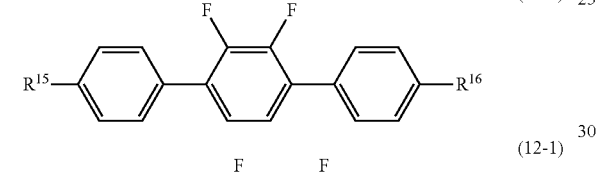
(12-1)
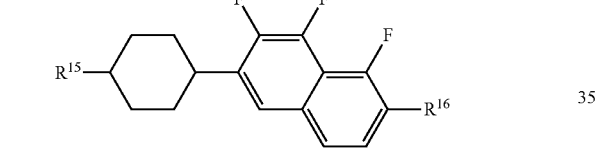
(12-2)
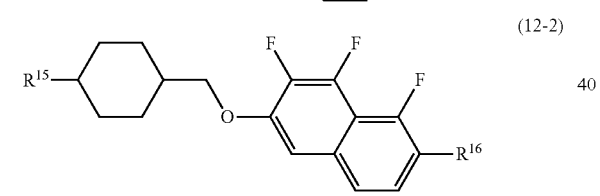
(12-3)
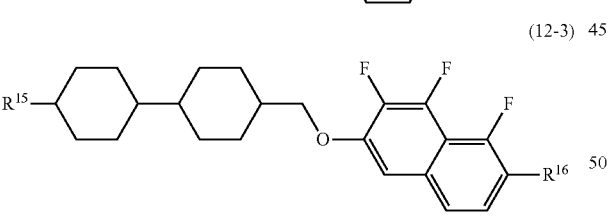
(13-1)
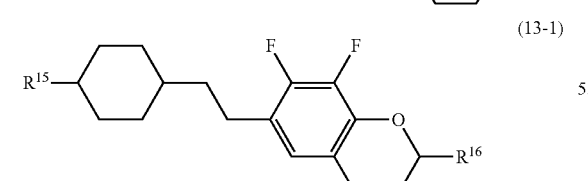
(13-2)
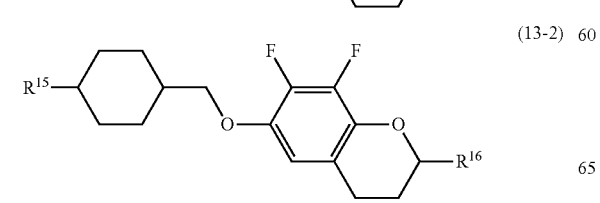
(13-3)
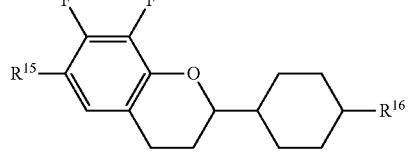
(13-4)
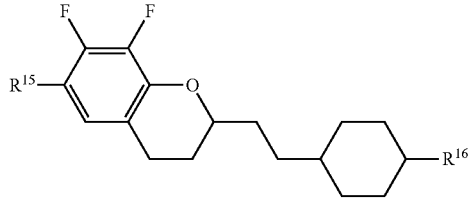
(13-5)
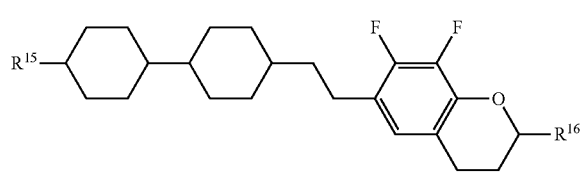
(13-6)
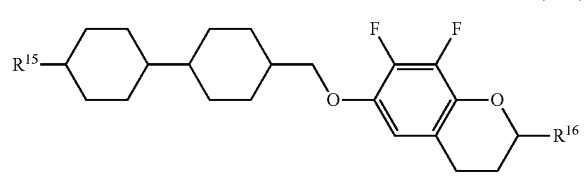
(13-7)
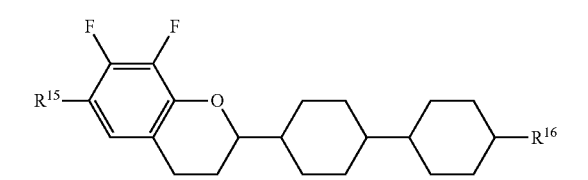
(13-8)
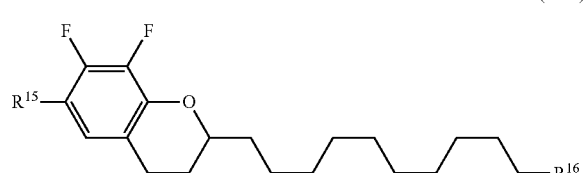
(13-9)
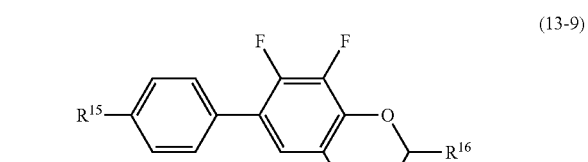
(13-10)
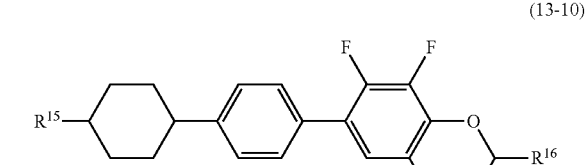

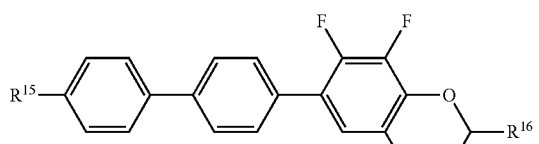 (13-11)

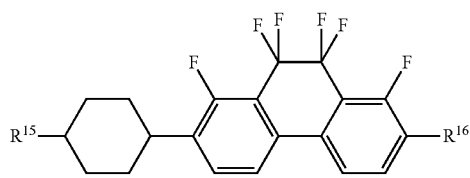 (14-1)

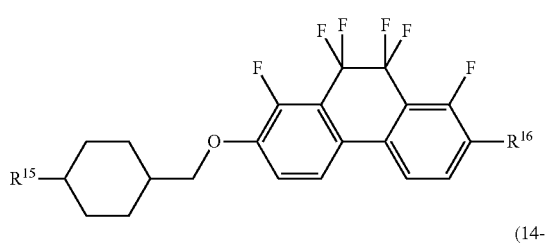 (14-2)

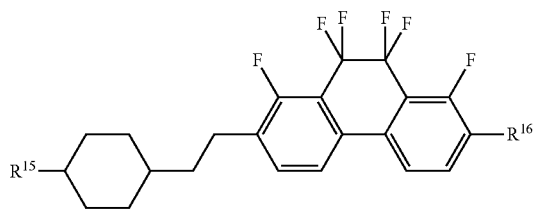 (14-3)

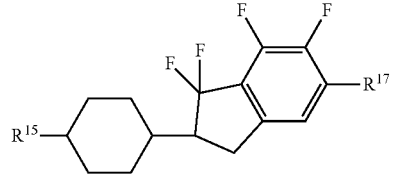 (15-1)

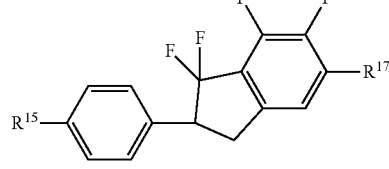 (15-2)

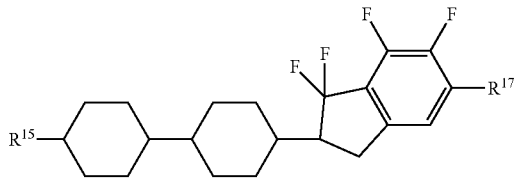 (15-3)

Compounds (9) to (15) have the large negative dielectric anisotropy. The compounds are used for preparing a composition for the mode such as the IPS mode, the VA mode and the PSA mode. As a content of the compound is increased, the dielectric anisotropy of the composition negatively increases, but the viscosity also increases. Thus, as long as a desired value of threshold voltage of the device is met, the content is preferably as small as possible. Therefore, in consideration of the dielectric anisotropy being approximately −5, the content is preferably approximately 40% by weight or more in order to allow sufficient voltage drive.

In the compounds, compound (9) is a bicyclic compound, and therefore effective mainly in decreasing the viscosity, adjusting the optical anisotropy or increasing the dielectric anisotropy. Compounds (10) and (11) are a tricyclic compound, and therefore effective in increasing the maximum temperature, the optical anisotropy or the dielectric anisotropy. Compounds (12) to (15) are effective in increasing the dielectric anisotropy.

When a composition for the mode such as the IPS mode, the VA mode and the PSA mode is prepared, a content of compounds (9) to (15) is preferably approximately 40% by weight or more, and further preferably in the range of approximately 50% by weight to approximately 95% by weight, based on the weight of the liquid crystal composition. When compounds (9) to (15) are added to a composition having the positive dielectric anisotropy, a content of the compound is preferably approximately 30% by weight or less based on the weight of the liquid crystal composition. When the compound is added thereto, the elastic constant of the composition and the voltage-transmittance curve of the device can be adjusted.

The liquid crystal composition is prepared by a method for dissolving necessary components at a temperature higher than room temperature, or the like. According to an application, an additive may be added to the composition. Specific examples of the additive include the optically active compound, the antioxidant, the ultraviolet light absorber, the light stabilizer, the heat stabilizer, the antifoaming agent, the polymerizable compound, the polymerization initiator and the polymerization inhibitor. Such additives are well known to those skilled in the art, and described in literature.

The optically active compound is effective in inducing a helical structure in liquid crystal molecules to give a required twist angle, thereby being effective in preventing a reverse twist. A helical pitch can be adjusted by adding the optically active compound thereto. Two or more optically active compounds may be added for the purpose of adjusting temperature dependence of the helical pitch. Specific examples of a preferred optically active compound include compounds (Op-1) to (Op-18) described below. In compound (Op-18), ring J is 1,4-cyclohexylene or 1,4-phenylene, and $R^{28}$ is alkyl having 1 to 10 carbons.

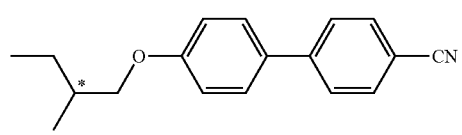 (Op-1)

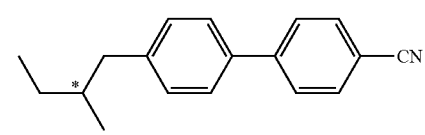 (Op-2)

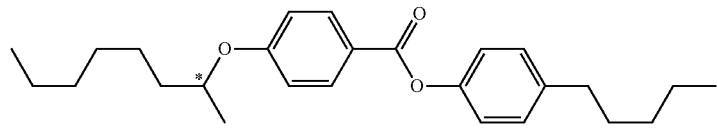
(Op-3)
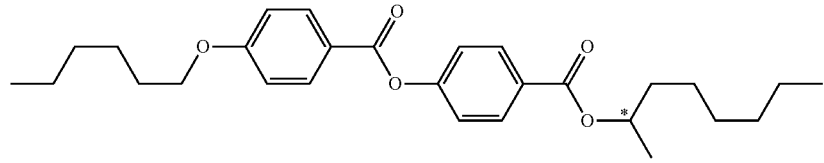
(Op-4)
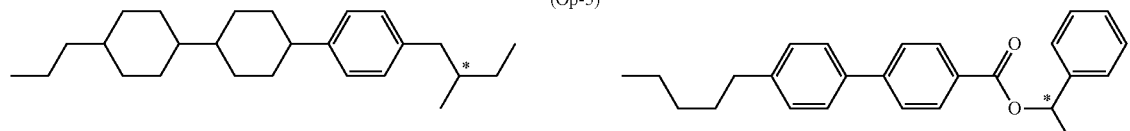
(Op-5) (Op-6)
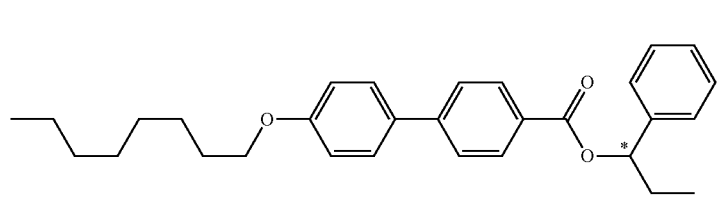
(Op-7)
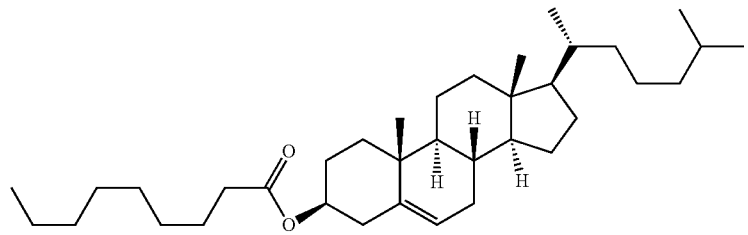
(Op-8)
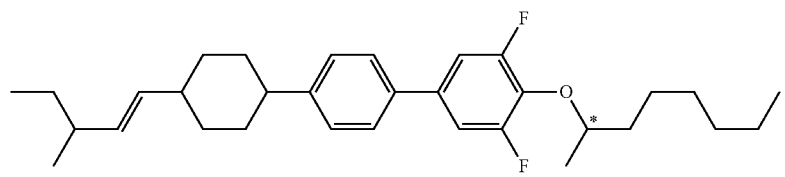
(Op-9)
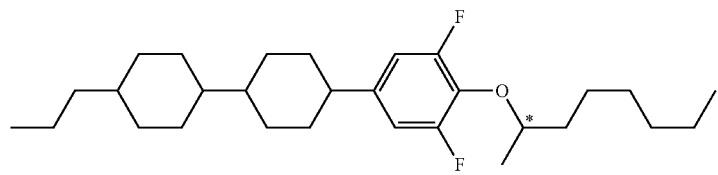
(Op-10)
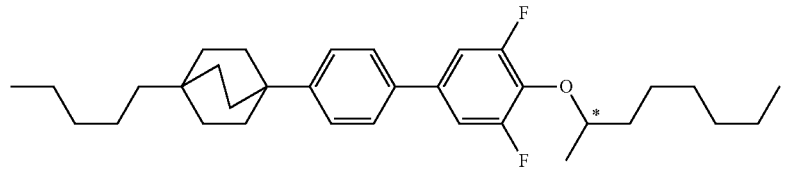
(Op-11)
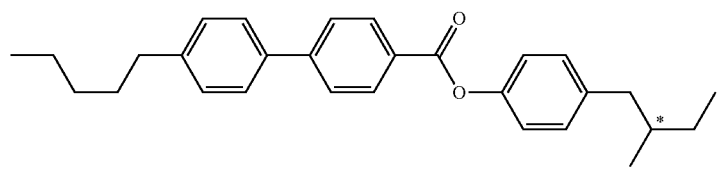
(Op-12)

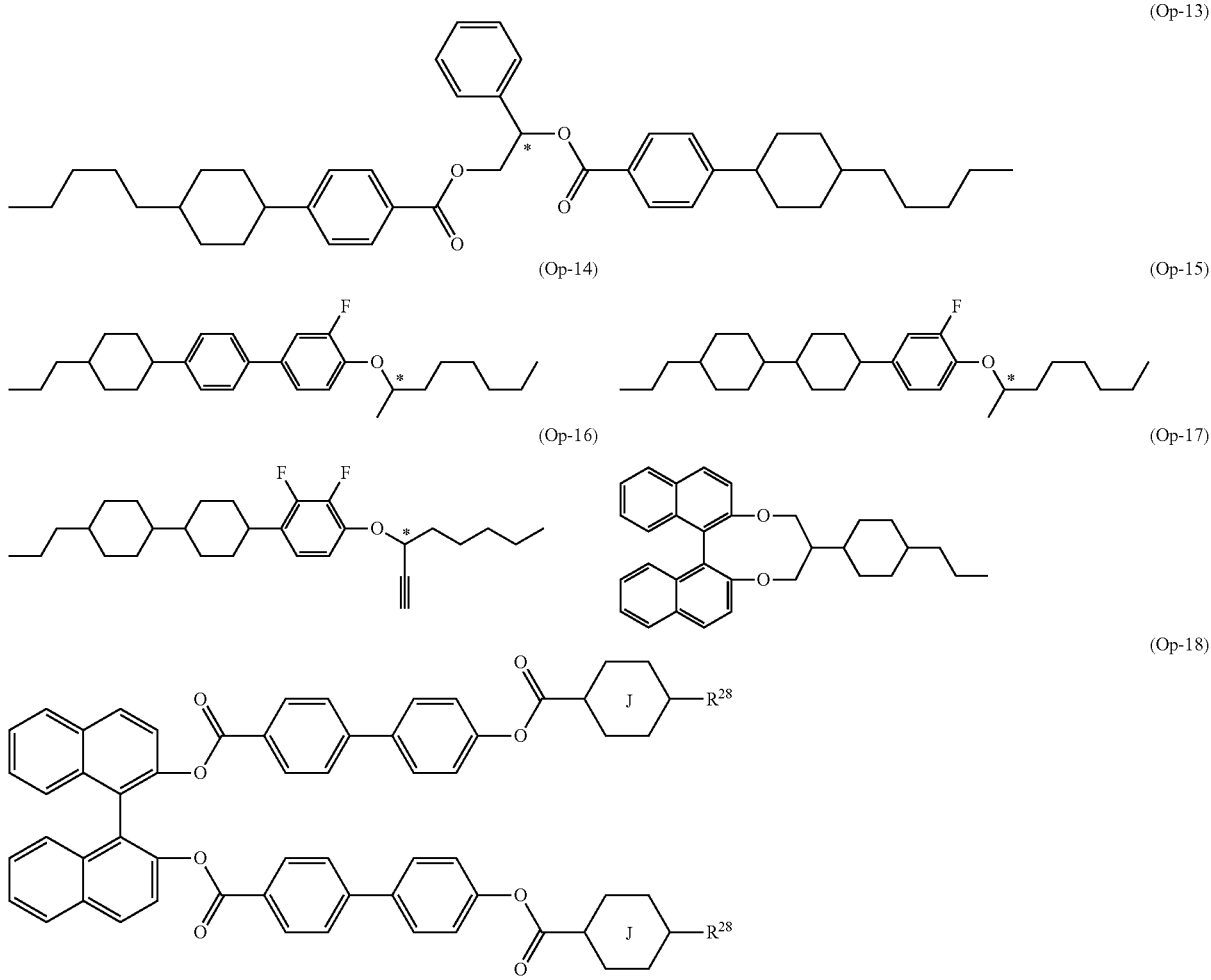

The antioxidant is effective for maintaining a large voltage holding ratio. Specific examples of a preferred antioxidant include compounds (AO-1) and (AO-2) described below; and IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease of the maximum temperature. Specific examples of a preferred ultraviolet light absorber include a benzophenone derivative, a benzoate derivative and a triazole derivative. Specific examples include compounds (AO-3) and (AO-4) described below; TINUVIN329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

A light stabilizer such as amine having steric hindrance is preferred for maintaining the large voltage holding ratio. Specific examples of a preferred light stabilizer include compounds (AO-5) and (AO-6) described below; and TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). The defoaming agent is effective for preventing foam formation. Specific examples of a preferred de foaming agent include dimethyl silicone oil and methylphenyl silicone oil.

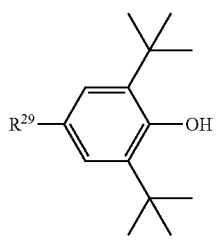

(AO-1)

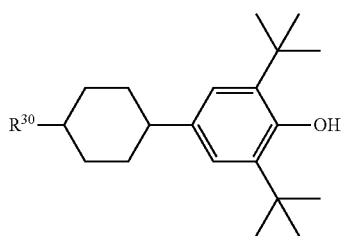

(AO-2)

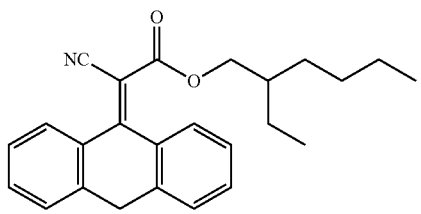
(AO-3)

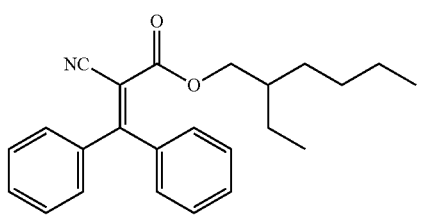
(AO-4)

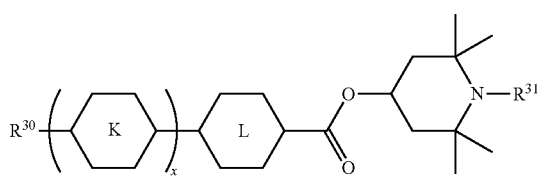
(AO-5)

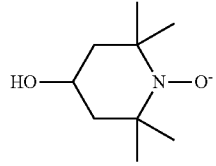
(AO-6)

In compound (AO-1), $R^{29}$ is alkyl having 1 to 20 carbons, alkoxy having 1 to 20 carbons, —COOR$^{32}$ or —CH$_2$CH$_2$COOR$^{32}$, and $R^{32}$ is alkyl having 1 to 20 carbons. In compounds (AO-2) and (AO-5), $R^{30}$ is alkyl having 1 to 20 carbons. In compound (AO-5), $R^{31}$ is hydrogen, methyl or O· (oxygen radical), ring K and ring L are 1,4-cyclohexylene or 1,4-phenylene, and x is 0, 1 or 2.

The polymerizable compound is polymerized while the compound is three-dimensionally controlled to allow shortening of a response time of the device and an improvement in image persistence. Specific examples of a preferred polymerizable compound include acrylate, methacrylate, a vinyl compound, a vinyloxy compound, propenyl ether, an epoxy compound (oxirane, oxetane) and vinyl ketone. Specific examples of a further preferred compound include a compound having at least one acryloyloxy and a compound having at least one methacryloyloxy. Specific examples of a still further preferred compound include a compound having both of acryloyloxy and methacryloyloxy.

Specific additional examples of other polymerizable compounds include compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

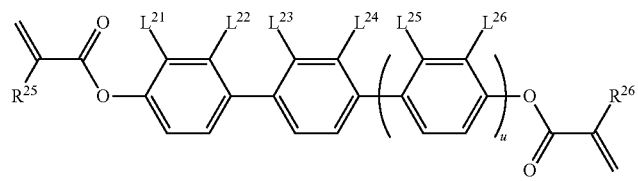
(M-1)

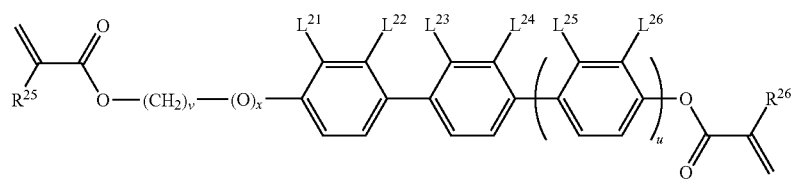
(M-2)

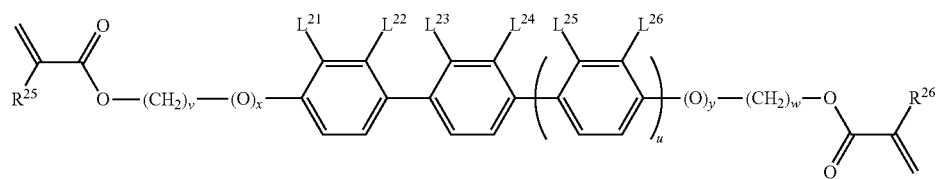
(M-3)

-continued
(M-4)
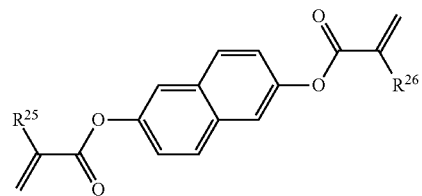
(M-5)
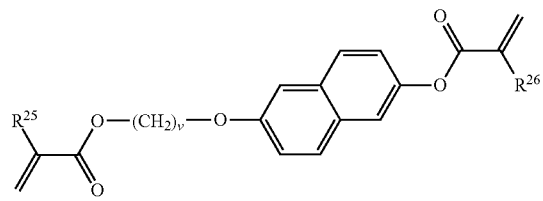
(M-6)
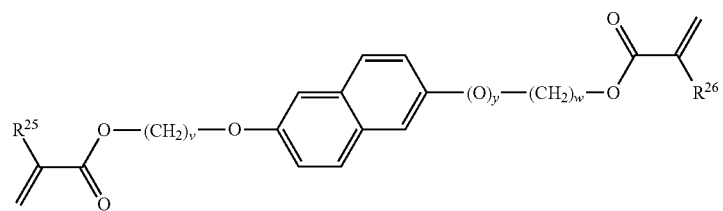
(M-7)
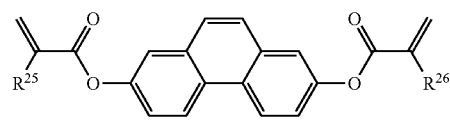
(M-8)
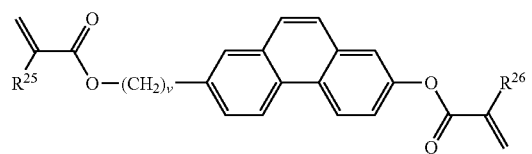
(M-9)
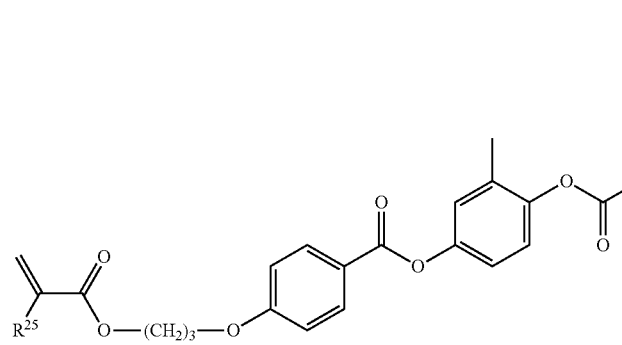
(M-10)
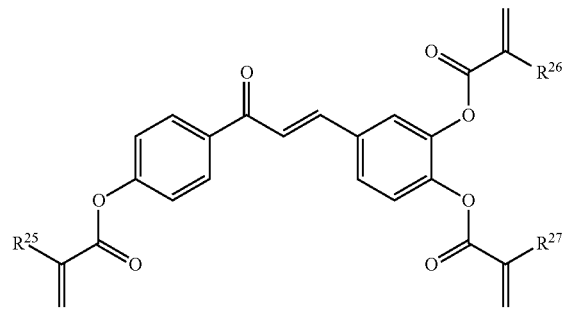
(M-11)
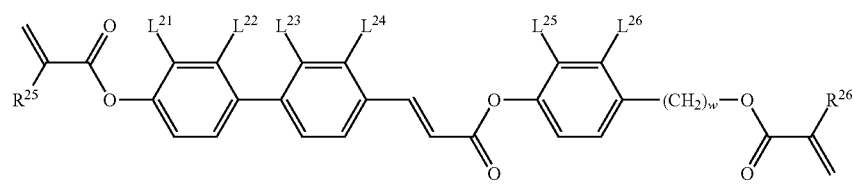
(M-12)
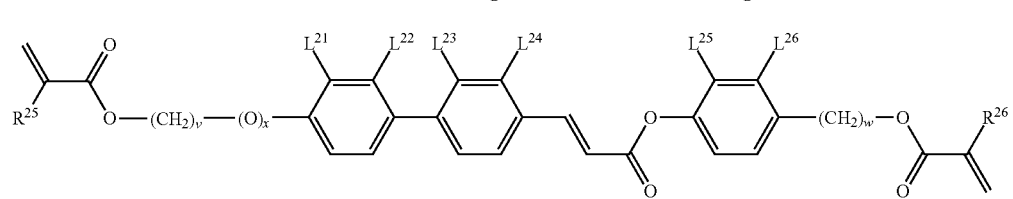

The polymerizable compound can be rapidly polymerized by adding the polymerizable initiator. An amount of a remaining polymerizable compound can be decreased by optimizing a reaction temperature. Specific examples of a photoradical polymerization initiator include TPO, 1173 and 4265 from Darocur series, and 184, 369, 500, 651, 784, 819, 907, 1300, 1700, 1800, 1850, and 2959 from Irgacure series of BASF SE.

Specific additional examples of the photoradical polymerization initiator include 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole/mercaptobenzimidazole mixture, 1-(4-isopropylphenyl)-2-hydroxy-2-methylpropane-1-one, benzyldimethyl ketal, 2-methyl-1-[4-(methylthio)phenyl]-2-morpholinopropane-1-one, a 2,4-diethylxanthone-methyl p-dimethylaminobenzoate mixture and a benzophenone-methyltriethanolamine mixture.

Upon storing the polymerizable compound, the polymerization inhibitor may be added thereto. The polymerizable compound is ordinarily added to the composition without removing the polymerization inhibitor. Specific examples of the polymerization inhibitor include hydroquinone, a hydroquinone derivative such as methylhydroquinone, 4-tert-butylcatechol, 4-methoxyphenol and phenothiazine.

4. Liquid Crystal Display Device

A liquid crystal composition having the large positive dielectric anisotropy can be used for a liquid crystal display device having an operating mode such as the PC mode, the TN mode, the STN mode, the OCB mode and the PSA mode, and driven by an active matrix (AM mode). The composition can also be used for a liquid crystal display device having an operating mode such as the PC mode, the TN mode, the STN mode, the OCB mode, the VA mode and the IPS mode, and driven by a passive matrix (PM) mode. The AM mode device and the PM mode device can be applied to any of a reflective type, a transmissive type and transflective type.

A liquid crystal composition having the large negative dielectric anisotropy has the negative dielectric anisotropy, and therefore can be suitably used for a liquid crystal display device that has an operating mode such as the VA mode, the IPS mode and the PSA mode, and is driven by an AM mode. The composition can be particularly suitably used for the liquid crystal display device that has the VA mode and is driven by the AM mode.

The composition can also be used for a nematic curvilinear aligned phase (NCAP) device prepared by microencapsulating a nematic liquid crystal, a polymer dispersed liquid crystal display device (PDLCD) and a polymer network liquid crystal display device (PNLCD), in which a three-dimensional network polymer is formed in the liquid crystal. When an amount of adding the polymerizable compound is in the range approximately 0.1% by weight to approximately 2% by weight based on the weight of the liquid crystal composition, the liquid crystal display device having the PSA mode can be prepared. The device having the PSA mode can be operated in a driving mode such as the active matrix (AM) or the passive matrix (PM). The device having the polymer dispersed mode can also be prepared by increasing an amount of adding the polymerizable compound.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. The invention is not limited by the Examples.

1. Example of Compound (1)

Compound (1) was prepared according to methods shown in Example 1, or the like. The thus prepared compound was identified by methods such as an NMR analysis. Characteristics of the compound were measured by methods as described below.

NMR Analysis:

For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, measurement was carried out using $CFCl_3$ as an internal standard and under conditions of 24 times of accumulation. In the explanation of nuclear magnetic resonance spectra, symbols s, d, t, q, quin, sex, m and br stand for a singlet, a doublet, a triplet, a quartet, a quintet, a sextet, a multiplet and being broad, respectively.

HPLC Analysis:

For measurement, Prominence (LC-20AD; SPD-20A) made by Shimadzu Corporation was used. As a column, YMC-Pack ODS-A (length: 150 mm, bore: 4.6 mm, particle diameter: 5 μm) made by YMC GmbH was used. As an eluate, acetonitrile and water were appropriately mixed and used. As a detector, a UV detector, an RI detector, a CORONA detector or the like was appropriately used. When the UV detector was used, a detection wavelength was adjusted to 254 nm. A sample was dissolved in acetonitrile and prepared to be a 0.1 wt % solution, and 1 microliter of the solution was injected into a sample injector. As a recorder, C-R7Aplus made by Shimadzu Corporation was used.

Ultraviolet-Visible Spectrophotometry:

For measurement, PharmaSpec UV-1700 made by Shimadzu Corporation was used. A detection wavelength was adjusted to 190 to 700 nm. A sample was dissolved in acetonitrile and prepared to be a solution of 0.01 mmol per liter, and measurement was carried out by putting the solution in a quartz cell (optical path length: 1 cm).

Sample for Measurement:

When phase structure and a transition temperature (a clearing point, a melting point, a polymerization starting temperature or the like) were measured, a liquid crystal compound itself was used as a sample. When characteristics such as a maximum temperature of a nematic phase, viscosity, optical anisotropy and dielectric anisotropy were measured, a mixture prepared by mixing the compound with a base liquid crystal was used as a sample.

When a sample in which the compound was mixed with the base liquid crystal was used, measurement was carried out according to a method described below. The sample was prepared by mixing 15% by weight of the compound and 85% by weight of the base liquid crystal. Then, extrapolated values were calculated from measured values of the sample, according to an extrapolation method, expressed by an equation below, and the extrapolated values were described. {Extrapolated value}={100× (measured value of a sample)−(% by weight of base liquid crystal)×(measured value of the base liquid crystal)}/(% by weight of the compound).

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight), and physical properties of the sample at a ratio at which no crystals (or no smectic phase) precipitated at 25° C. were measured. In addition, unless otherwise noted, the ratio of the compound to the base liquid crystal was 15% by weight:85% by weight.

When the dielectric anisotropy of the compound was positive, base liquid crystal (i) described below was used. Ratios of components of the base liquid crystal are expressed in terms of weight percent (% by weight).

Base Liquid Crystal (i):

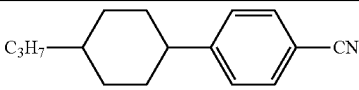

When the dielectric anisotropy of the compound was negative, base liquid crystal (ii) described below was used.

Base Liquid Crystal (ii):

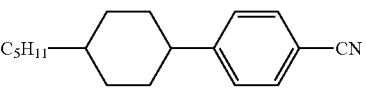

Measuring Methods:

Characteristics were measured according to the methods described below. Most of the measuring methods are applied as described in the Standard of the Japan Electronics and Information Technology Industries Association (JEITA EIAJ ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc. or a high sensitivity differential scanning calorimeter, X-DSC7000, made by SII NanoTechnology, Inc. was used. A sample was heated and then cooled at a rate of 3° C. per minute. A starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to the liquid may be occasionally abbreviated as "clearing point."

The crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. A higher limit of the temperature range of the nematic phase may be occasionally abbreviated as "maximum temperature." When the sample was a mixture of compound (1) and the base liquid crystal, the maximum temperature was expressed in terms of a symbol $T_{NI}$. When the sample was a mixture of compound (1) and a compound such as compounds (2) to (15), the maximum temperature was expressed in terms of a symbol NI.

(4) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., $T_c$ was expressed as $T_c \le -20°$ C. A lower limit of the temperature range of the nematic phase may be occasionally abbreviated as "minimum temperature."

(5) Compatibility of Compounds

Several compounds having a similar structure were mixed to prepare a base liquid crystal having the nematic phase. A compound to be measured was added to the base liquid crystal. One example of a mixing ratio is 15% by weight of the compound and 85% by weight of the base liquid crystal. The composition was stored for 30 days at a low temperature such as −20° C. and −30° C. Whether or not part of the composition changed to the crystals (or the smectic phase) was observed. A mixing ratio and a storage temperature were changed, when necessary. From the thus measured results, conditions under which the crystals (or the smectic phase) precipitated or conditions under which no crystals (or no smectic phase) precipitated were determined. The conditions serve as a measure of compatibility.

(6) Viscosity (Bulk Viscosity; η; Measured at 20° C.; mPa·s)

Viscosity was measured using a cone-plate (E type) rotational viscometer made by Tokyo Keiki, Inc.

(7) Optical Anisotropy (Refractive Index Anisotropy; Δn; Measured at 25° C.)

Measurement was carried out by an Abbe refractometer having a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: $\Delta n = n\| - n\perp$.

(8) Specific Resistance (ρ; Measured at 25° C.; Ωcm)

Into a vessel equipped with electrodes, 1.0 mL of a sample was injected. A direct current voltage (10 V) was applied to the vessel, and a direct current after 10 seconds was measured. Specific resistance was calculated from the following equation: (specific resistance)={(voltage)×(electric capacity of the vessel)}/{(direct current)×(dielectric constant of vacuum)}.

(9) Voltage Holding Ratio (VHR-1; Measured at 25° C.; %):

A TN device used for measurement had a polyimide alignment film, and a distance (cell gap) between two glass substrates was 5 micrometers. A sample was put in the device, and the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(10) Voltage Holding Ratio (VHR-2; Measured at 80° C.; %)

A voltage holding ratio was measured according to procedures identical with the procedures described above except that measurement was carried out at 80° C. in place of 25° C. The thus obtained results were expressed in terms of a symbol VHR-2.

The method of measuring the physical properties may be occasionally different between a sample having the positive dielectric anisotropy and a sample having the negative dielectric anisotropy. The measuring methods when the dielectric anisotropy is positive were described in sections (11a) to (15a). The methods when the dielectric anisotropy is negative were described in sections (11b) to (15b).

(11a) Viscosity (Rotational Viscosity; γ1; Measured at 25° C.; mPa·s)

Positive dielectric anisotropy: Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device with which the rotational viscosity was measured and by a method described below.

(11b) Viscosity (Rotational Viscosity; γ1; Measured at 25° C.; mPa·s)

Negative dielectric anisotropy: Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. As dielectric anisotropy required for the calculation, a value measured in a section of dielectric anisotropy described below was used.

(12a) Dielectric Anisotropy (Δ∈; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in the major axis direction of liquid crystal molecules was measured. Sine waves (0.5 V, 1 kHz) were applied to the device, and after 2 seconds, a dielectric constant (∈⊥) in the minor axis direction of the liquid crystal molecules was measured. A value of dielectric anisotropy was calculated from an equation: $\Delta\in = \in\| - \in\perp$.

(12b) Dielectric Anisotropy (Δ∈; Measured at 25° C.)

Negative dielectric anisotropy: A value of dielectric anisotropy was calculated from an equation: $\Delta\in = \in\| - \in\perp$. A dielectric constant (∈∥ and ∈⊥) was measured as described below.

(1) Measurement of dielectric constant (∈∥): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5V, 1 kHz) were applied to the device, and after 2 seconds, a dielectric constant (∈∥) in the major axis direction of liquid crystal molecules was measured.

(2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(13a) Elastic Constant (K; Measured at 25° C.; pN)

Positive dielectric anisotropy: HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is a mean value of the thus determined $K_{11}$, $K_{22}$ and $K_{33}$.

(13b) Elastic Constant ($K_{11}$ and $K_{33}$; Measured at 25° C.; pN)

Negative dielectric anisotropy: Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(14a) Threshold Voltage (Vth; Measured at 25° C.; V)

Positive dielectric anisotropy: An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 90% transmittance.

(14b) Threshold Voltage (Vth; Measured at 25° C.; V)

Negative dielectric anisotropy: An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage was expressed in terms of a voltage at 10% transmittance.

(15a) Response Time (τ; Measured at 25° C.; ms)

Positive dielectric anisotropy: An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 μm and a twist angle was 80 degrees. Rectangular waves (60 Hz, 5 V, 0.5 sec) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr; millisecond) is a period of time required for the change in transmittance from 90% to 10%. A fall time (τf: millisecond) is a period of time required for the change in transmittance from 10% to 90%. Response time was presented by a sum of the thus obtained rise time and fall time.

(15b) Response Time (τ; Measured at 25° C.; ms)

Negative dielectric anisotropy: An LCD-5100 luminance meter made by Otsuka Electronics Co., Ltd. was used for measurement. A light source was a halogen lamp. A low-pass filter was set at 5 kHz. A sample was put in a normally black mode PVA device in which a distance (cell gap) between two glass substrates was 3.2 micrometers and a rubbing direction was anti-parallel. The device was sealed with an ultraviolet-curable adhesive. The device was applied with a voltage of a little exceeding a threshold voltage for 1 minute, and then was irradiated with an ultraviolet light of 23.5 mW/cm² for 8 minutes, while applying a voltage of 5.6 V. Rectangular waves (60 Hz, 10 V, 0.5 sec) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time is a period of time required for a change from 90% transmittance to 10% transmittance (fall time; millisecond).

Example 1

Synthesis of 6-(4-ethoxy-2,3-difluorophenyl)-3-(4-propylcyclohexyl)-3,4-di hydro-2H-pyran (No. 160)

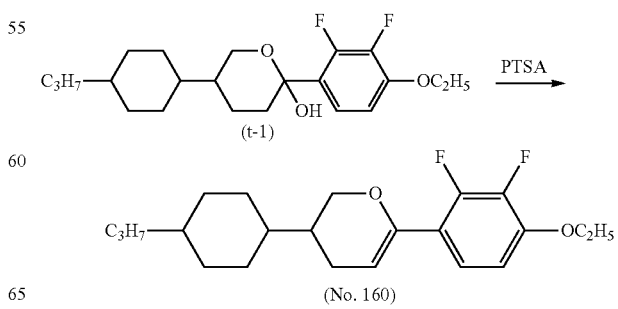

In toluene, 2-(4-ethoxy-2,3-difluorophenyl)-5-(4-propyl-cyclohexyl)tetrahydro-2H-pyran-2-ol (t-1) (1.4 g, 3.66 mmol) prepared by a known method and sodium p-toluenesulfonate monohydrate (0.010 g, 0.05 mmol) were heated under reflux for 2 hours. A reaction liquid was poured into a saturated aqueous sodium bicarbonate solution and subjected to extraction with toluene. An extracted organic layer was washed with water and saturated brine, and dried over magnesium sulfate, and then a solvent was distilled off with an evaporator. A residue was purified by silica gel chromatography and recrystallization to give compound (No. 160) (0.6 g, 1.64 mmol) (yield: 45%).

$^1$H-NMR (CDCl$_3$; δ ppm): 7.20 (td, 1H), 6.67 (td, 1H), 5.37 (td, 1H), 4.30 (ddd, 1H), 4.11 (q, 2H), 3.73 (t, 1H), 2.24 (dddd, 1H), 1.99 (dddd, 1H), 1.84-1.67 (m, 5H), 1.46 (t, 3H), 1.30 (six, 2H), 1.22-1.13 (m, 4H), 1.03 (qt, 2H), 0.91-0.83 (m, 5H).

Phase transition temperature: C 90.7 S$_A$ 143.8 N 158.5 I.

Compound (No. 160) was mixed with base liquid crystal (ii) in a ratio of 15% by weight, and the measurement results of the resulting mixture are shown below.

Maximum temperature (NI)=142.6° C.; dielectric anisotropy (Δ∈)=−4.14; optical anisotropy (Δn)=0.147; viscosity (η)=65.1 mPa·s.

Example 2

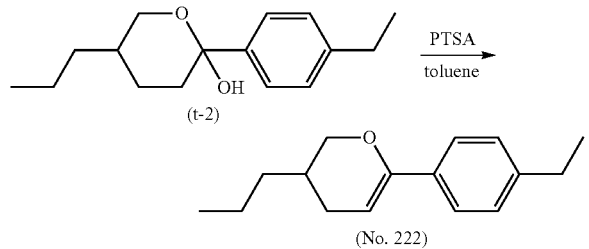

(t-2)

(No. 222)

In toluene, compound (t-2) (9.1 g, 36.64 mmol) prepared by a known method and sodium p-toluenesulfonate monohydrate (0.273 g, 1.44 mmol) were heated under reflux for 2 hours. A reaction liquid was poured into a saturated aqueous sodium bicarbonate solution and subjected to extraction with toluene. An extracted organic layer was washed with water and saturated brine, and dried over magnesium sulfate, and then a solvent was distilled off with an evaporator. A residue was purified by silica gel chromatography and recrystallization to give compound (No. 222) (3.0 g, 13.02 mmol) (yield: 35%).

$^1$H-NMR (CDCl$_3$; δ ppm): 7.37 (d, 2H), 7.30 (d, 2H), 4.91 (m, 1H), 4.29 (ddd, 1H), 3.70 (t, 1H), 2.62 (q, 2H), 2.21 (dddd, 1H), 1.96 (dddd, 1H), 1.71-1.65 (m, 1H), 1.43-1.05 (m, 7H), 0.93 (t, 3H).

Compound (No. 222) was mixed with base liquid crystal (ii) in a ratio of 15% by weight, and the measurement results of the resulting mixture are shown below.

Maximum temperature (NI)=−70.7° C.; dielectric anisotropy (Δ∈)=2.57; optical anisotropy (Δn)=0.063; viscosity (η)=14.7 mPa·s.

Example 3

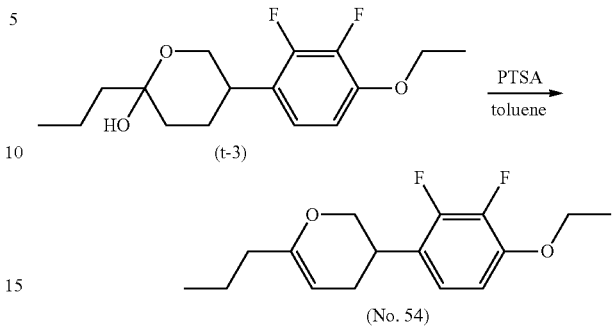

(t-3)

(No. 54)

In toluene, compound (t-3) (10.5 g, 34.96 mmol) prepared by a known method and sodium p-toluenesulfonate monohydrate (0.315 g, 1.83 mmol) were heated under reflux for 2 hours. A reaction liquid was poured into a saturated aqueous sodium bicarbonate solution and subjected to extraction with toluene. An extracted organic layer was washed with water and saturated brine, and dried over magnesium sulfate, and then a solvent was distilled off with an evaporator. A residue was purified by silica gel chromatography and recrystallization to give compound (No. 54) (4.8 g, 16.99 mmol) (yield: 48%).

$^1$H-NMR (CDCl$_3$; δ ppm): 7.20 (td, 1H), 6.67 (td, 1H), 4.77 (dddd, 1H), 4.53-4.54 (m, 1H), 4.13-4.07 (m, 3H), 3.38 (tt, 1H), 2.58 (tdd, 1H), 2.33 (dddd, 1H), 1.94 (t, 2H), 1.44 (t, 3H), 1.36 (six, 2H), 0.98 (t, 3H).

Compound (No. 54) was mixed with base liquid crystal (ii) in a ratio of 15% by weight, and the measurement results of the resulting mixture are shown in below.

Maximum temperature (NI)=−28.7° C.; dielectric anisotropy (Δ∈)=−7.75; optical anisotropy (Δn)=0.101; viscosity (η)=50.4 mPa·s.

Comparative Example 1

For comparison, comparative compound (R-1) was prepared according to the reaction formula described in Mol. Cryst. Liq. Cryst., Vol. 494, pp. 58-67, 2008, and the thus prepared compound was identified.

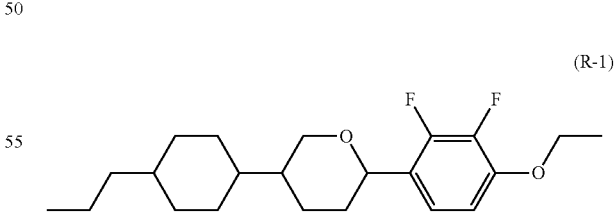

(R-1)

Physical properties of compound (R-1) were as follows. Phase transition temperature: C 107.7 N 164 I.

Compound (R-1) was mixed with base liquid crystal (ii) in a ratio of 15% by weight, and the resulting mixture was measured.

Maximum temperature (NI)=138.6° C.; dielectric anisotropy (Δ∈)=−3.76;

TABLE 1

Comparison of Maximum Temperature (NI) and Dielectric Anisotropy (ΔE)

| Liquid crystal compound | Structural formula | NI | ΔE |
|---|---|---|---|
| No. 160 | | 142.6 | −4.14 |
| Comparative compound (R-1) | | 138.6 | −3.76 |

From Table 1, high values are found to be shown in both of NI and Δ∈ in a case of compound (No. 160). Accordingly, the dihydropyran compound of the invention can be concluded to have larger NI and Δ∈ in comparison with a conventional tetrahydropyran compound.

Compounds shown below can be prepared with reference to the methods described in Example 1 and the description in "2. Synthetic method."

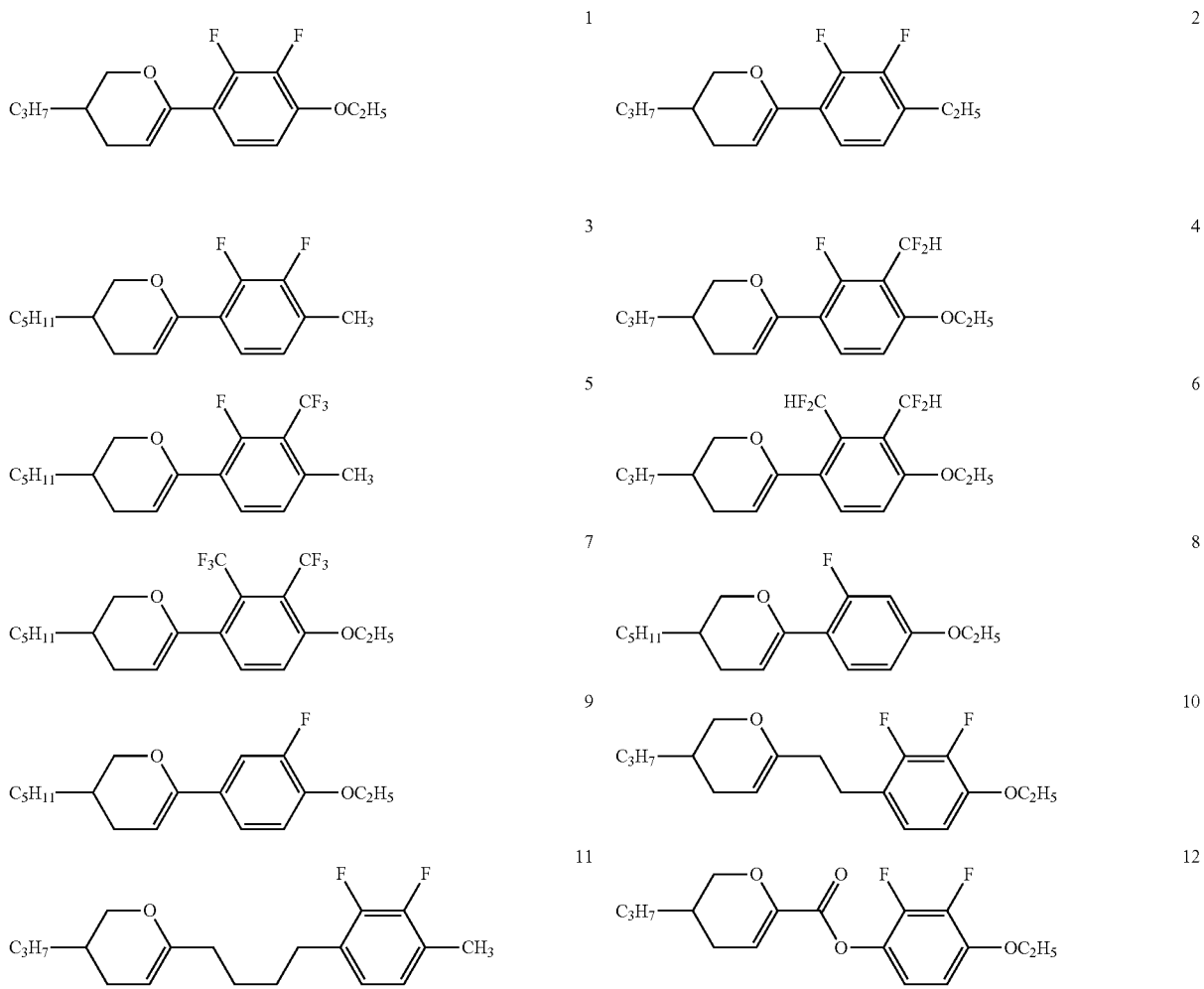

-continued

-continued
31
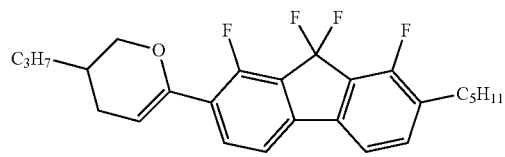
32
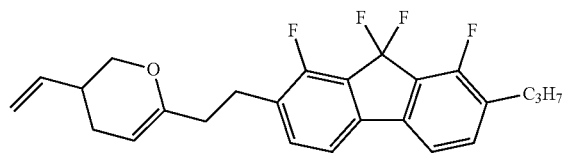
33
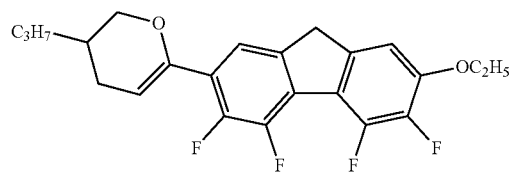
34
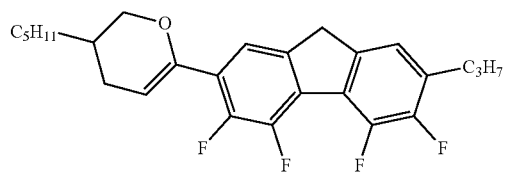
35
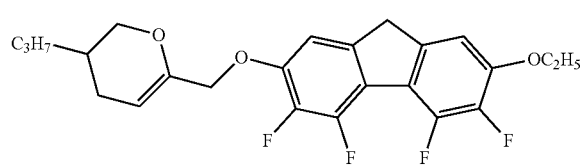
36
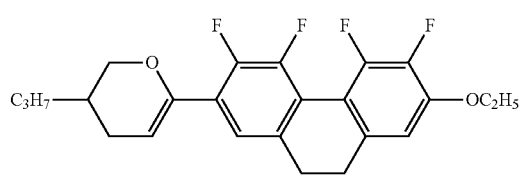
37
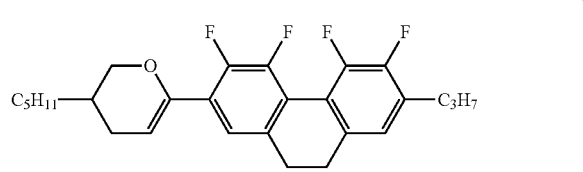
38
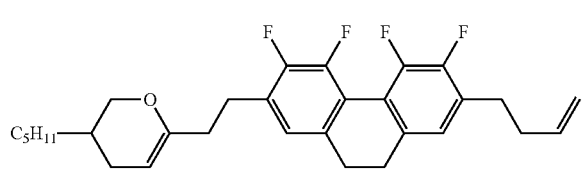
39
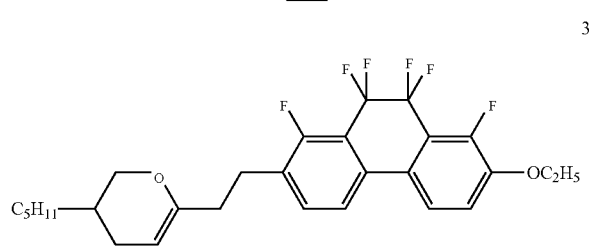
40
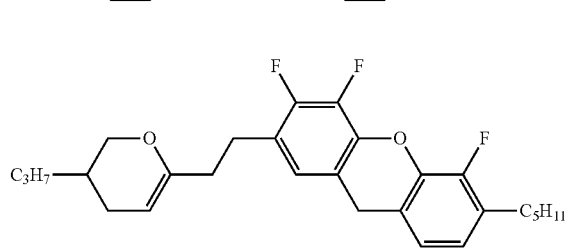
41
42
43
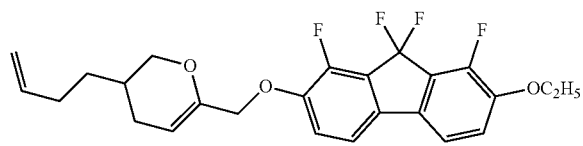
44
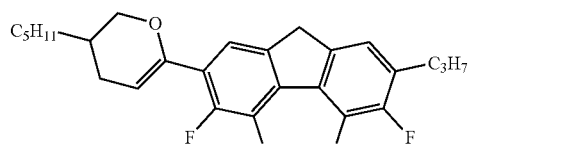
45
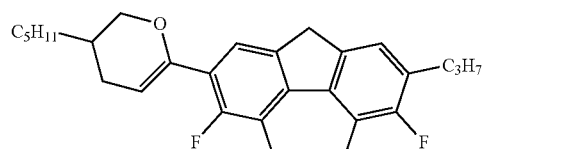
46
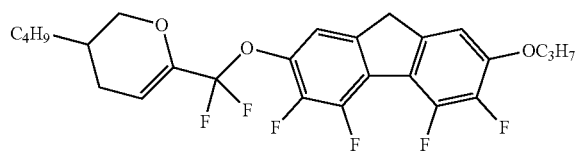

-continued
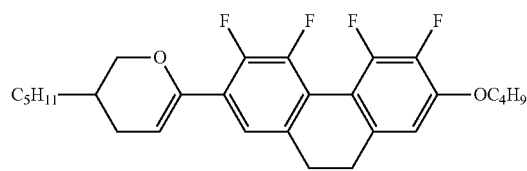
47
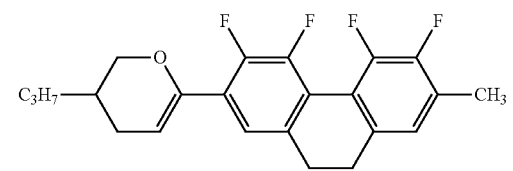
48
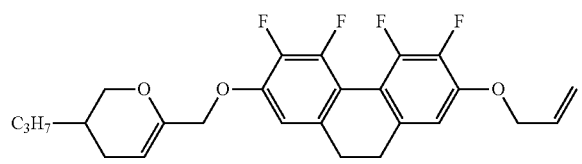
49
50
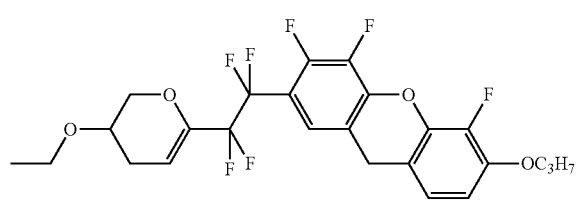
51
52
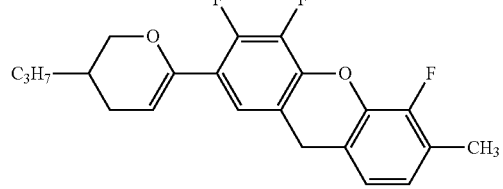
53
54
55
56
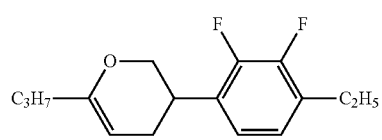
57
58
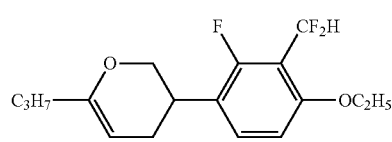
59
60
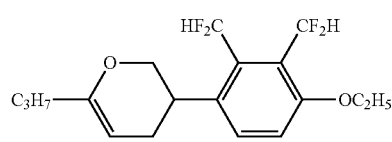
61
62
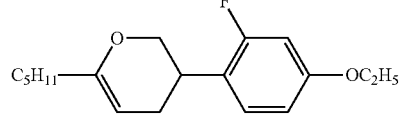
63
64
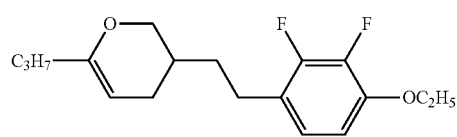

-continued
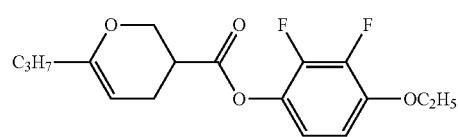
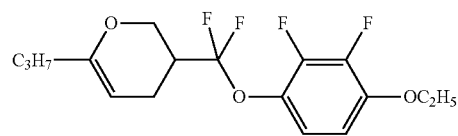
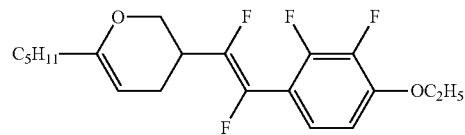
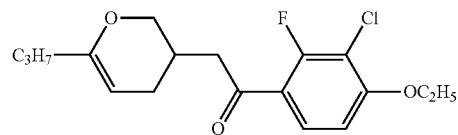
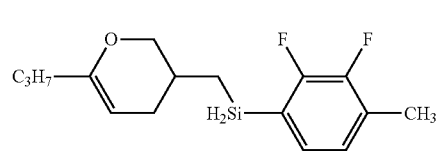
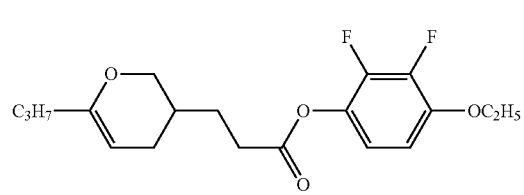
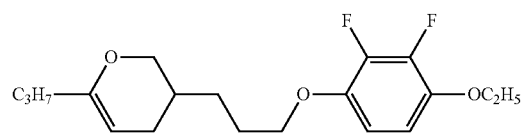
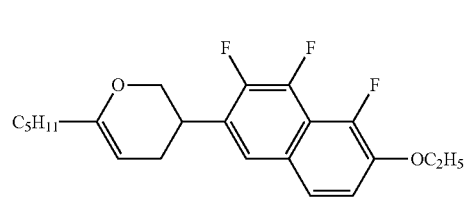
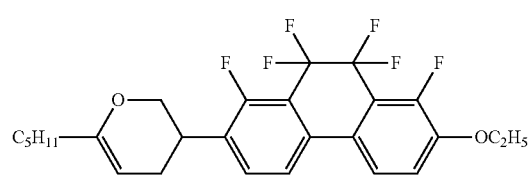
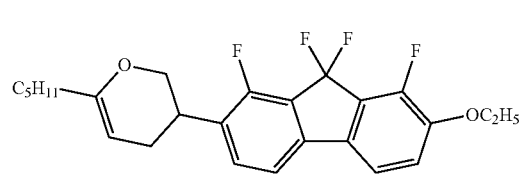
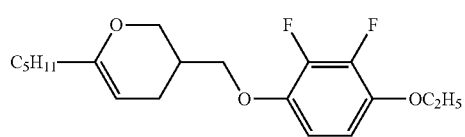
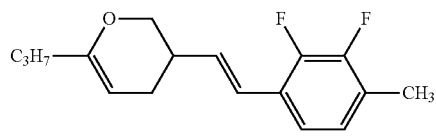
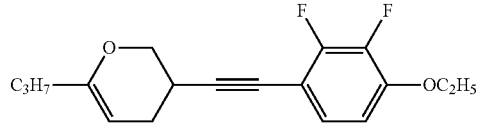
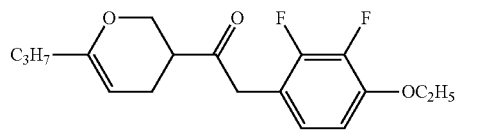
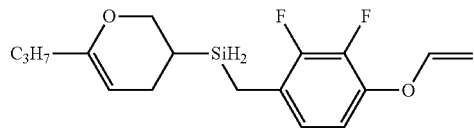
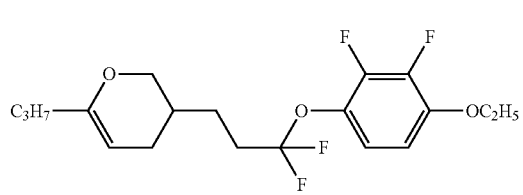
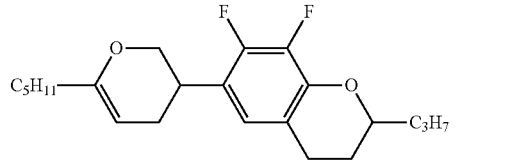
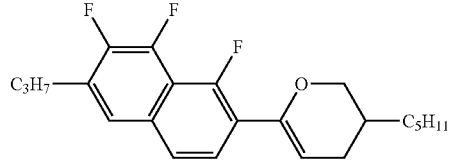
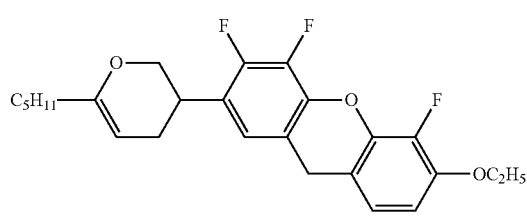
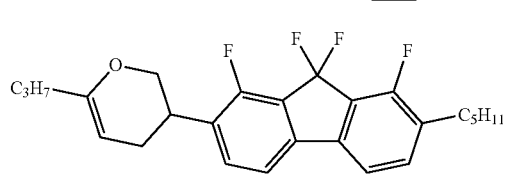

-continued
| 115 | 116 |
|---|---|
| 85 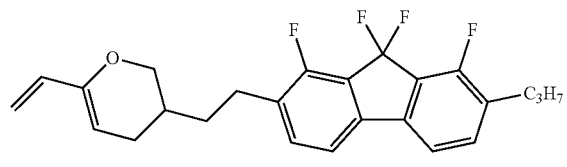 | 86 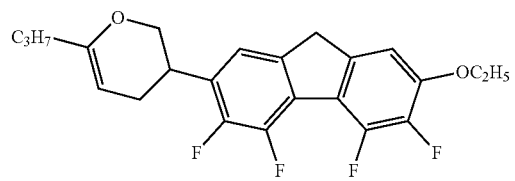 |
| 87 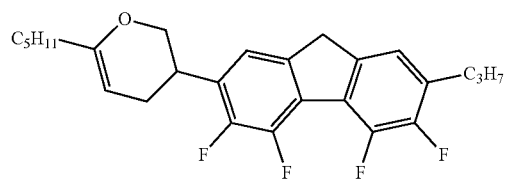 | 88 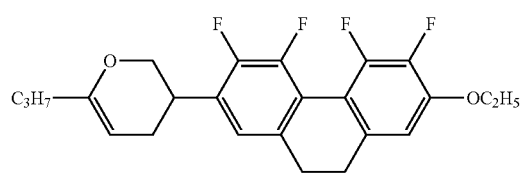 |
| 89 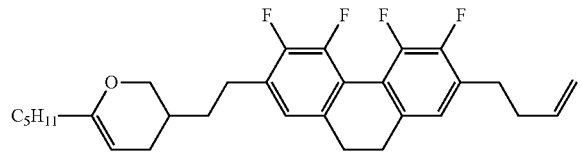 | 90 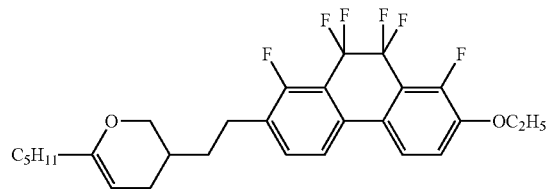 |
| 91 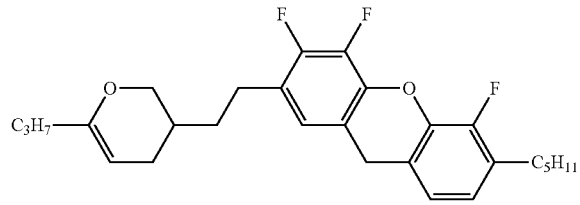 | 92  |
| 93 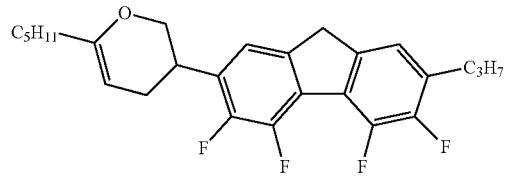 | 94 |
| 95 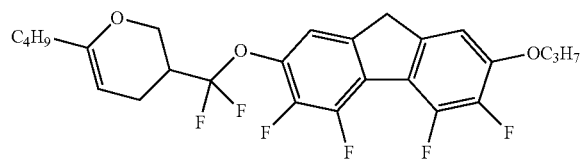 | 96 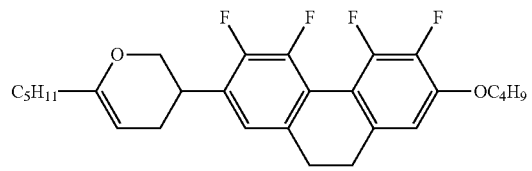 |
| 97 | 98 |
| 99 | 100 |

-continued
101
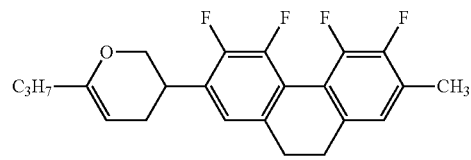
102
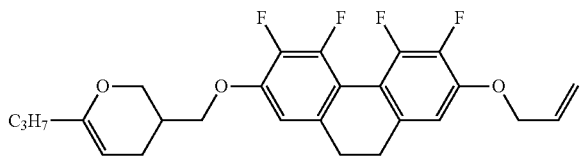
103
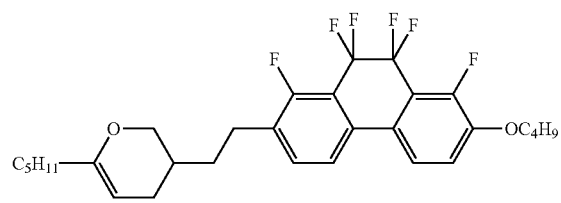
104
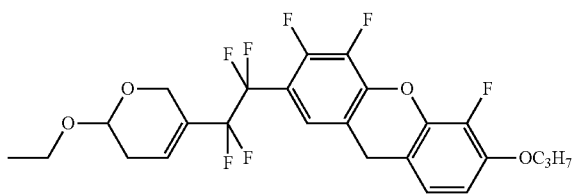
105
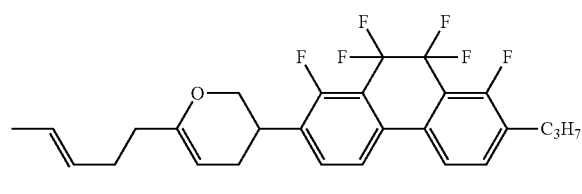
106
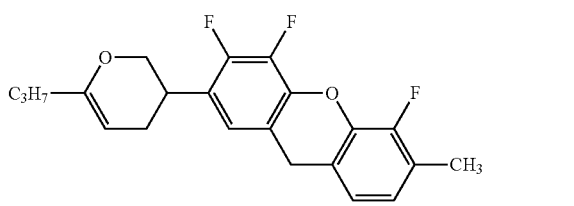
107
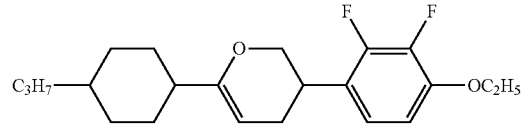
108
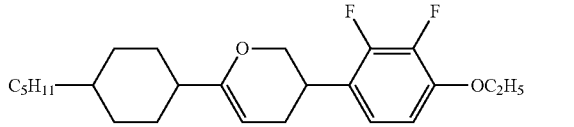
109
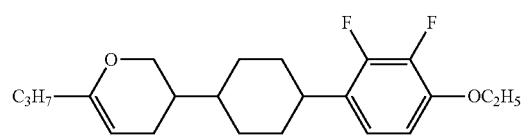
110
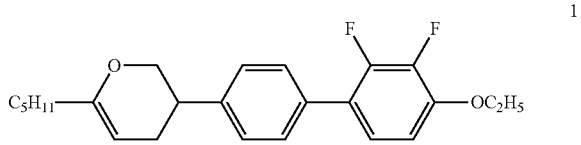
111
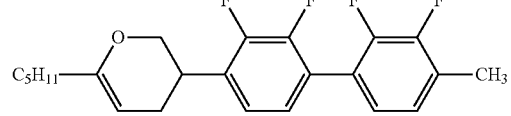
112
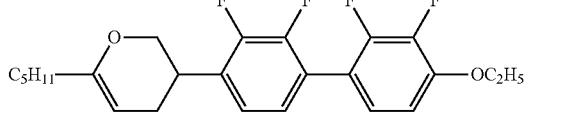
113
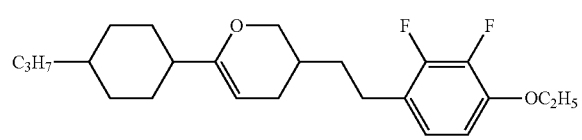
114
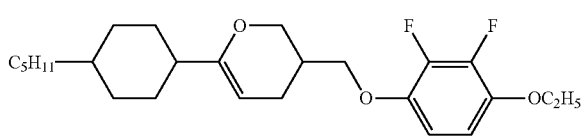
115
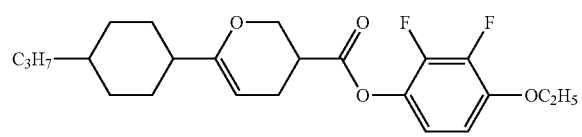
116
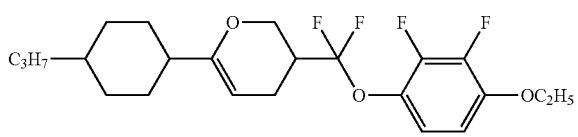
117
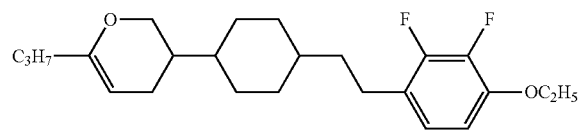
118

-continued
119
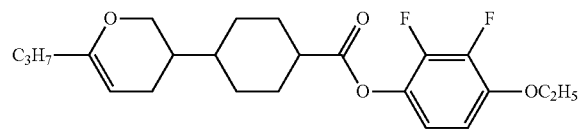
120
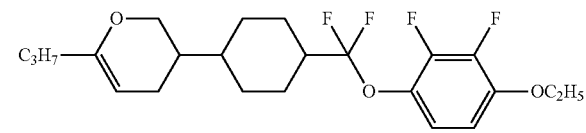
121
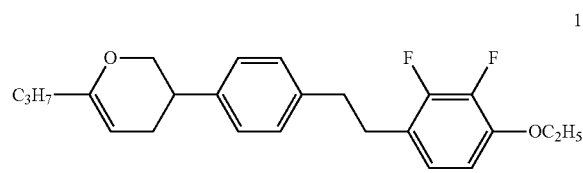
122
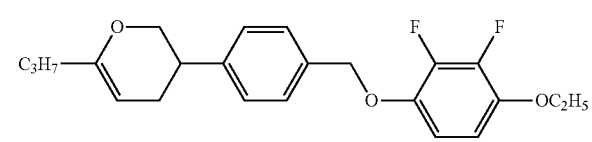
123
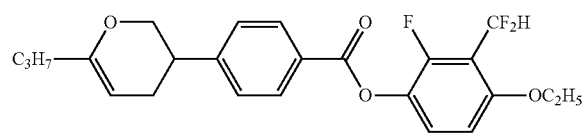
124
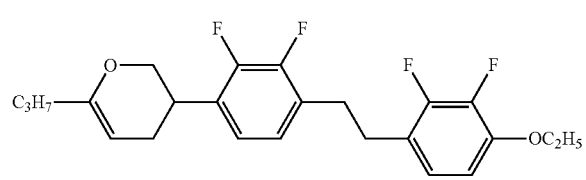
125
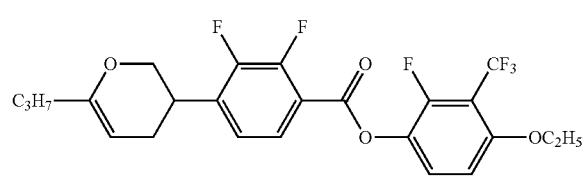
127
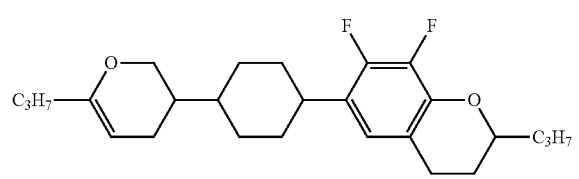
129
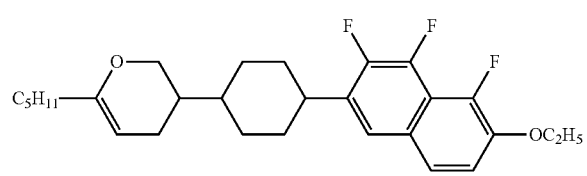
131
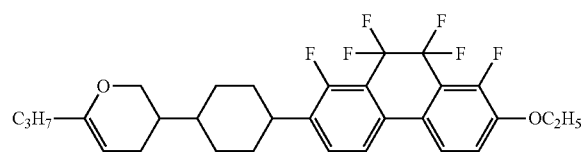
133
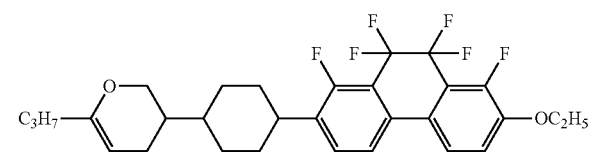

-continued
135
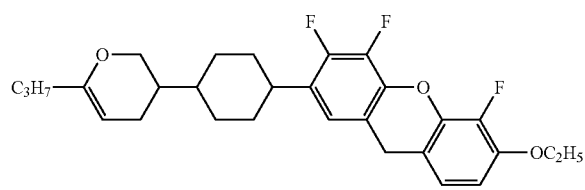
136
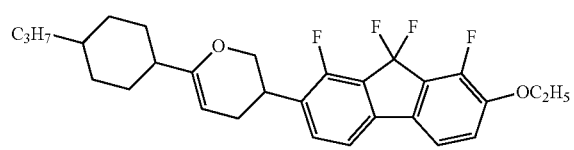
137
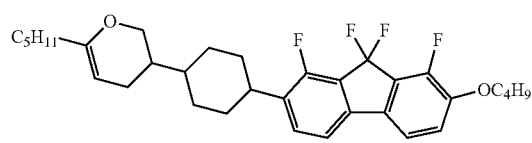
138
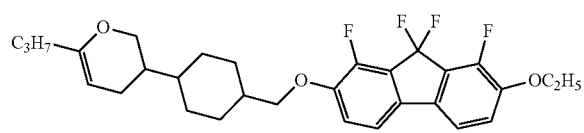
139
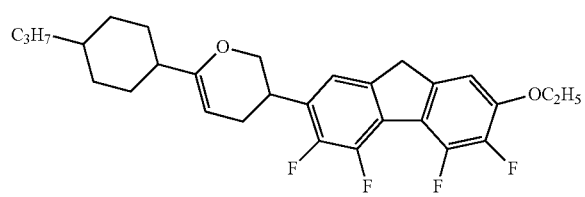
140
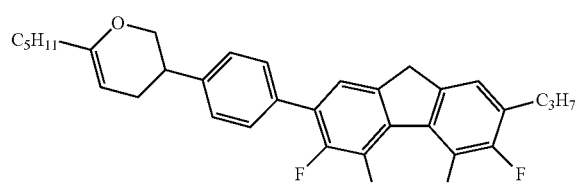
141
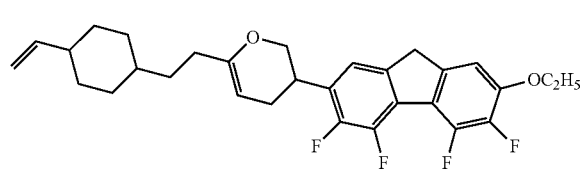
142
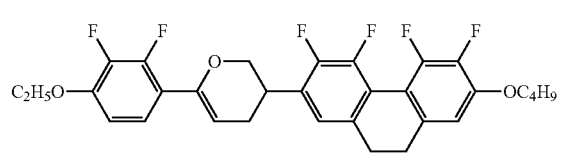
143
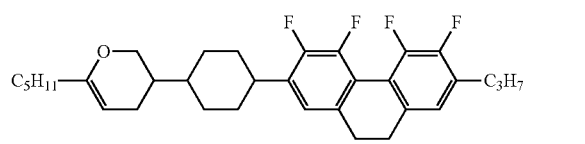
144
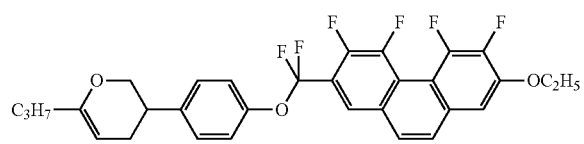
145
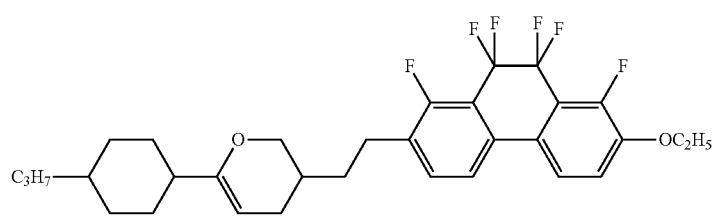
146
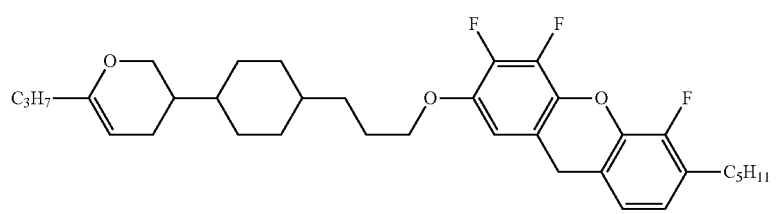
147
148
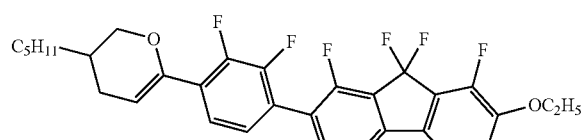

-continued
149
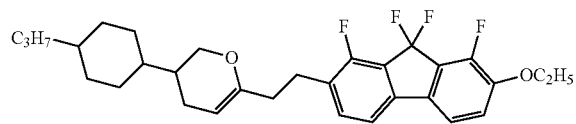
150
151
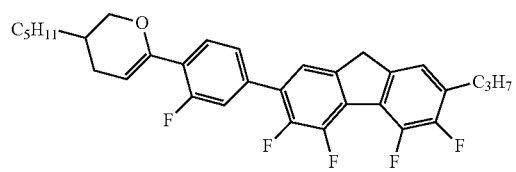
152
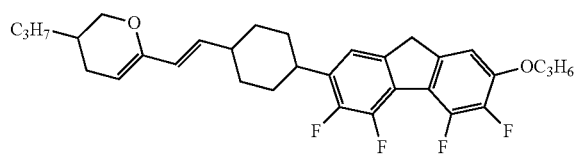
153
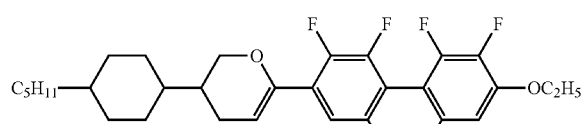
154
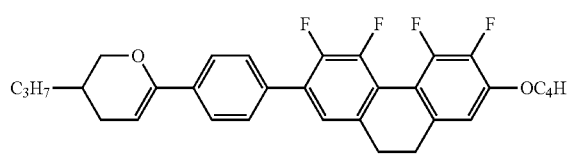
155
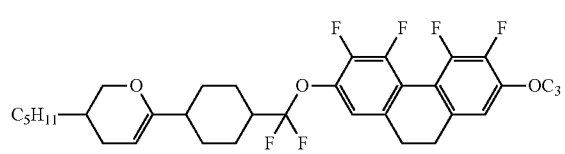
156
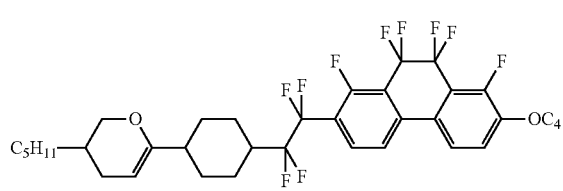
157
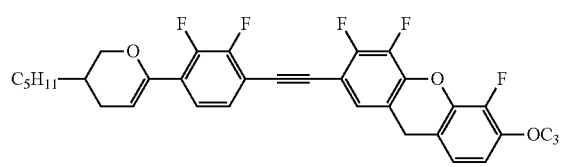
158
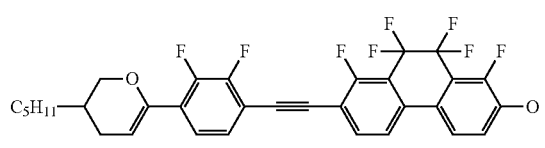
159
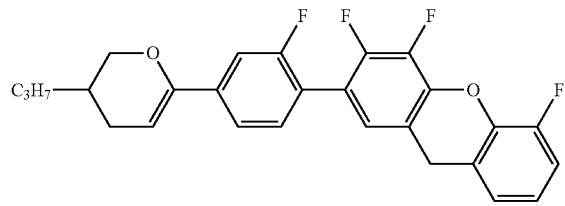
160
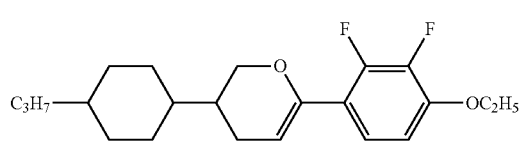
C 90.7 SA 143.8 N 158.5 I NI = 142.6° C.;
Δε = −4.14; Δn = 0.147;
η = 65.1 mPa·s.
161
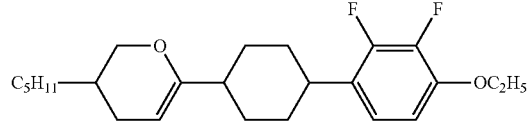
162
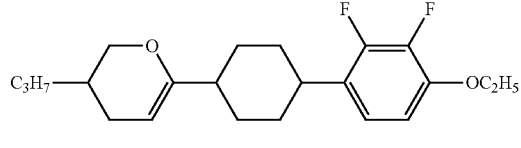
163
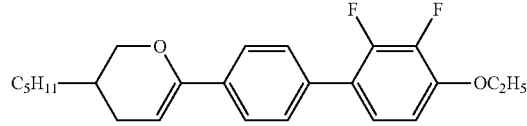
164
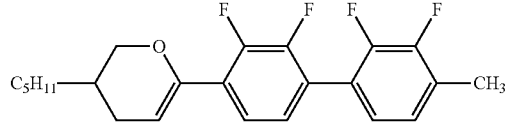
165
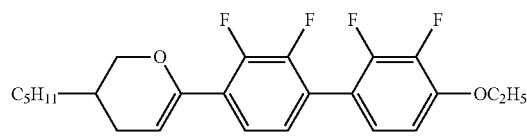
166
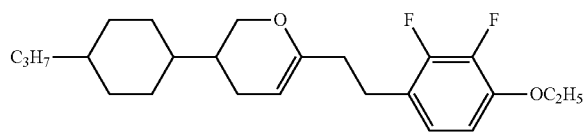

-continued
167
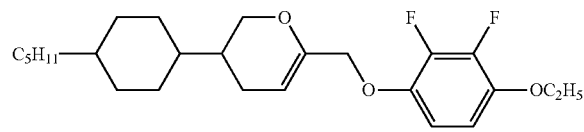
168
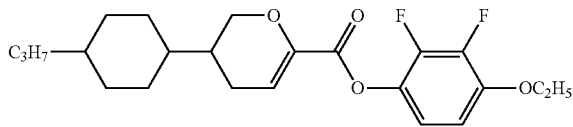
169
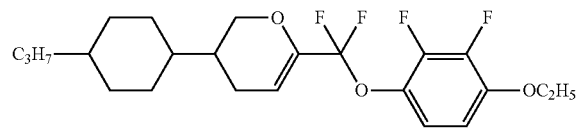
170
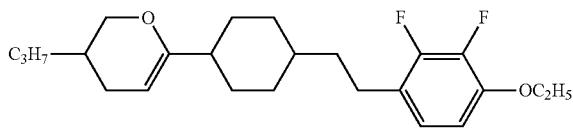
171
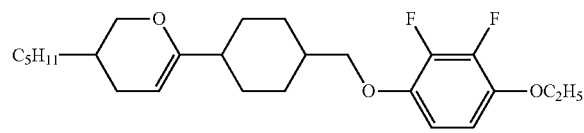
172
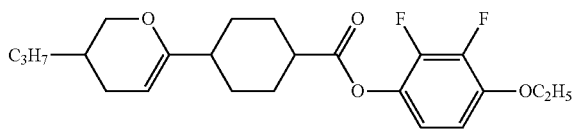
173
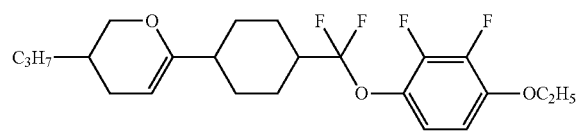
174
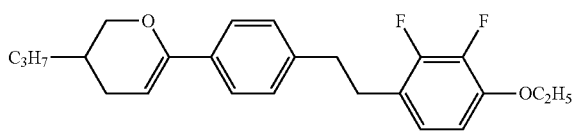
175
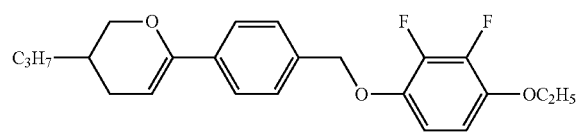
176
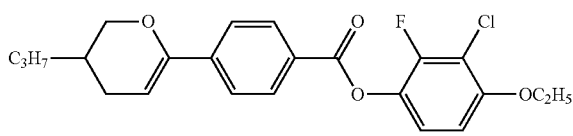
177
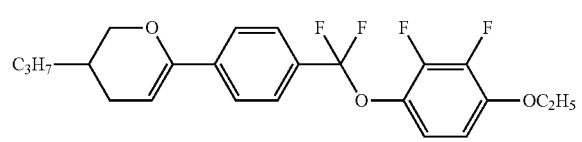
178
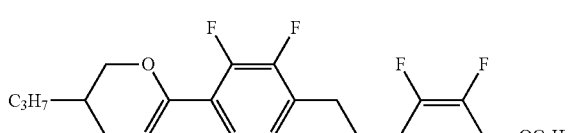
179
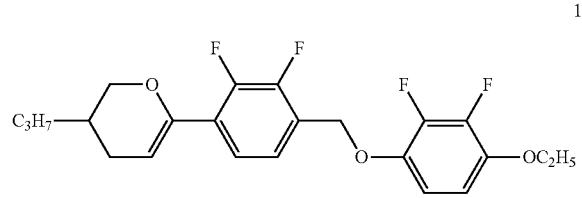
180
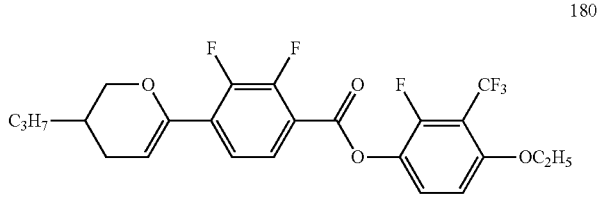
181
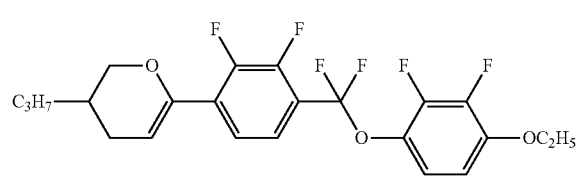
182
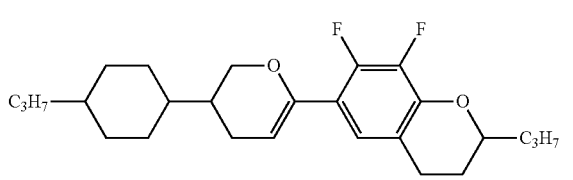
183
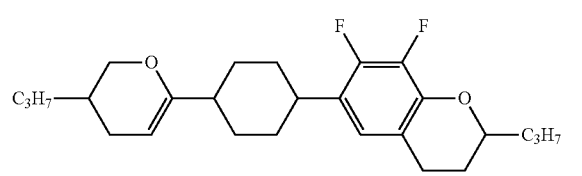
184
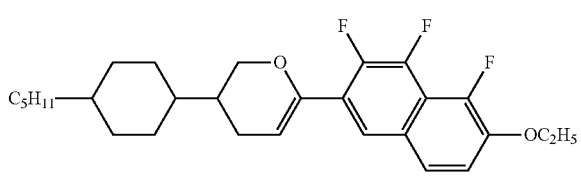

-continued
185
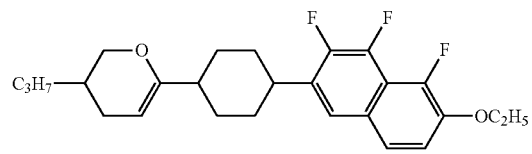
186
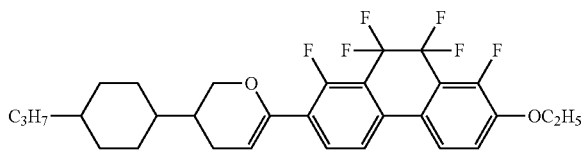
187
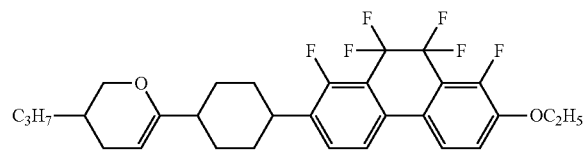
188
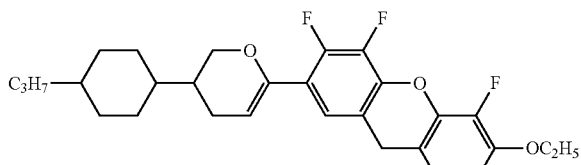
189
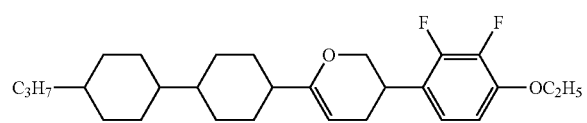
190
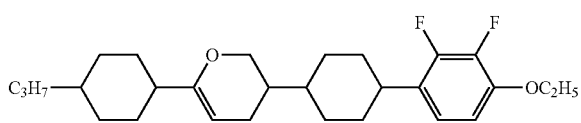
191
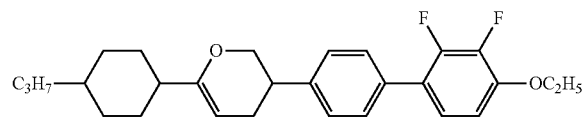
192
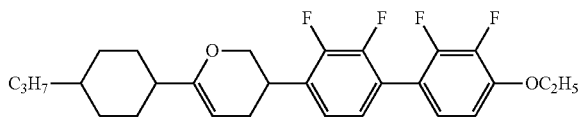
193
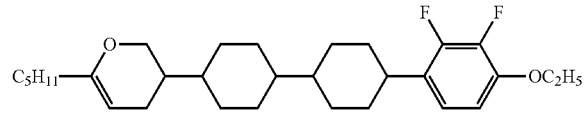
194
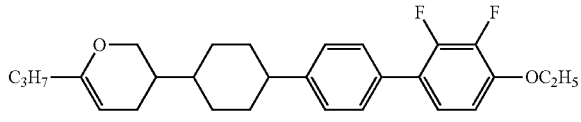
195
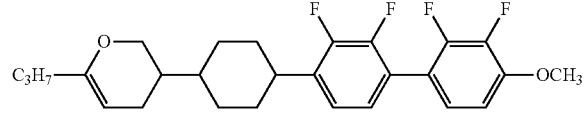
196
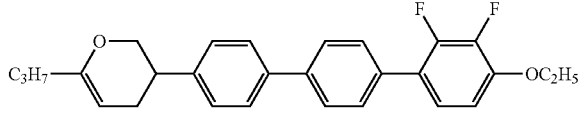
197
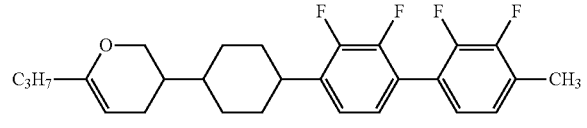
198
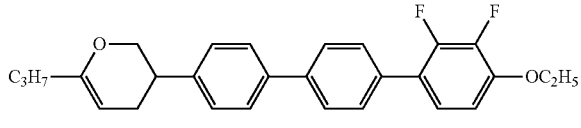
199
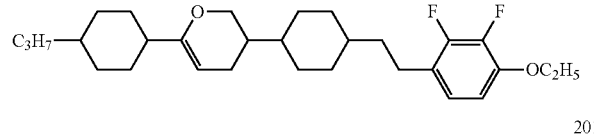
200
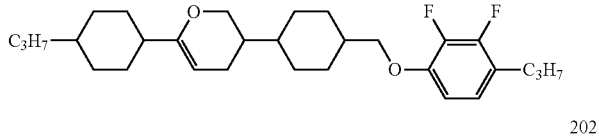
201
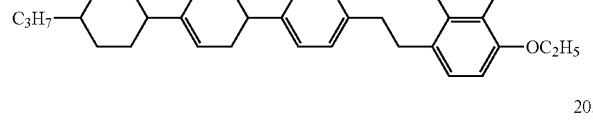
202
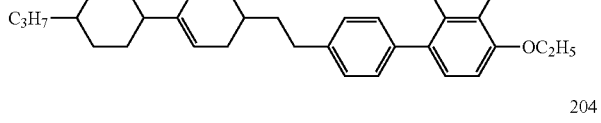
203
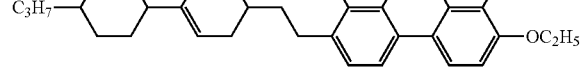
204
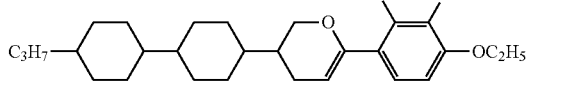

-continued
205
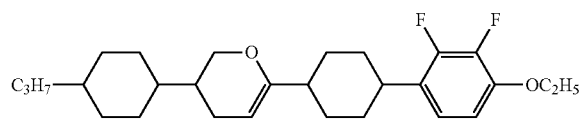
206
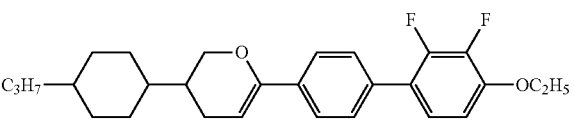
207
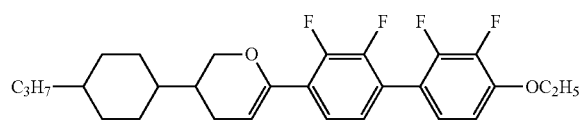
208
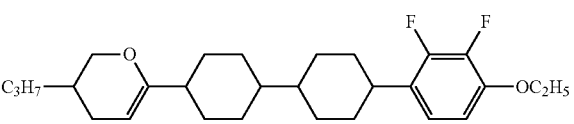
209
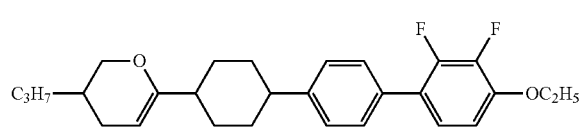
210
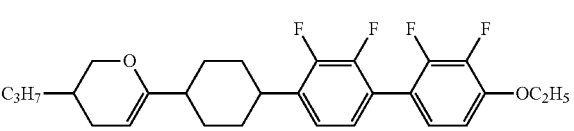
211
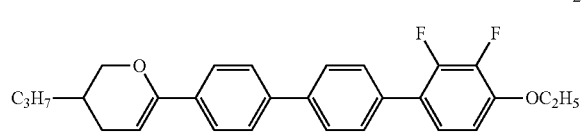
212
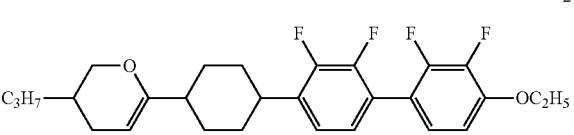
213
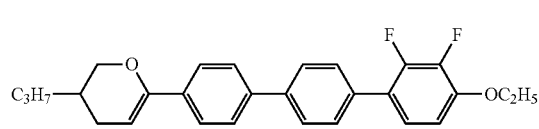
214
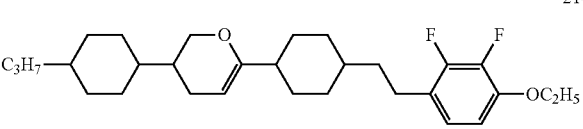
215
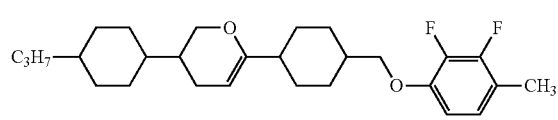
216
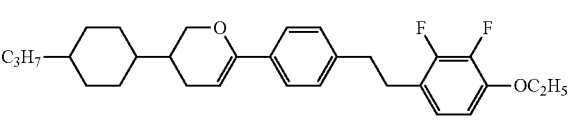
217
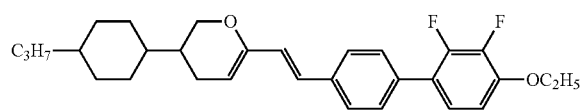
218
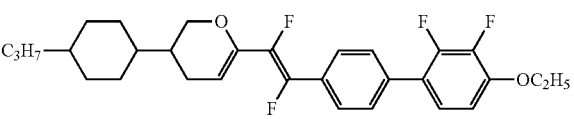
219
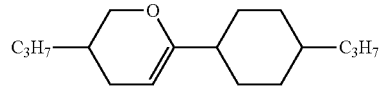
220
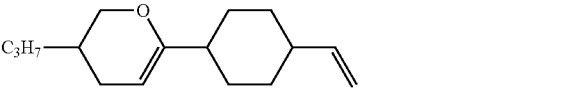
221
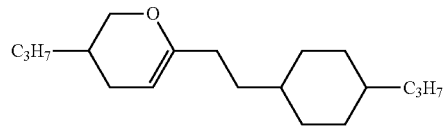
222
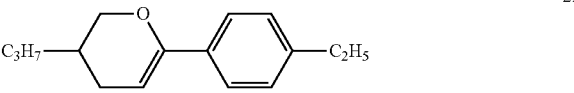
223
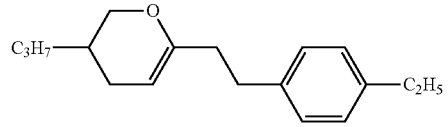
224
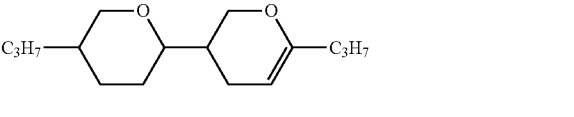
225
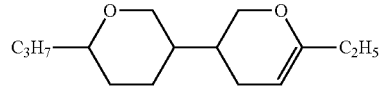
226
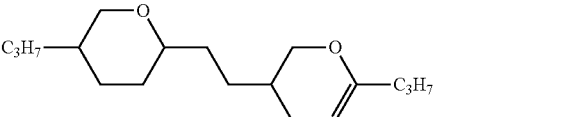

-continued

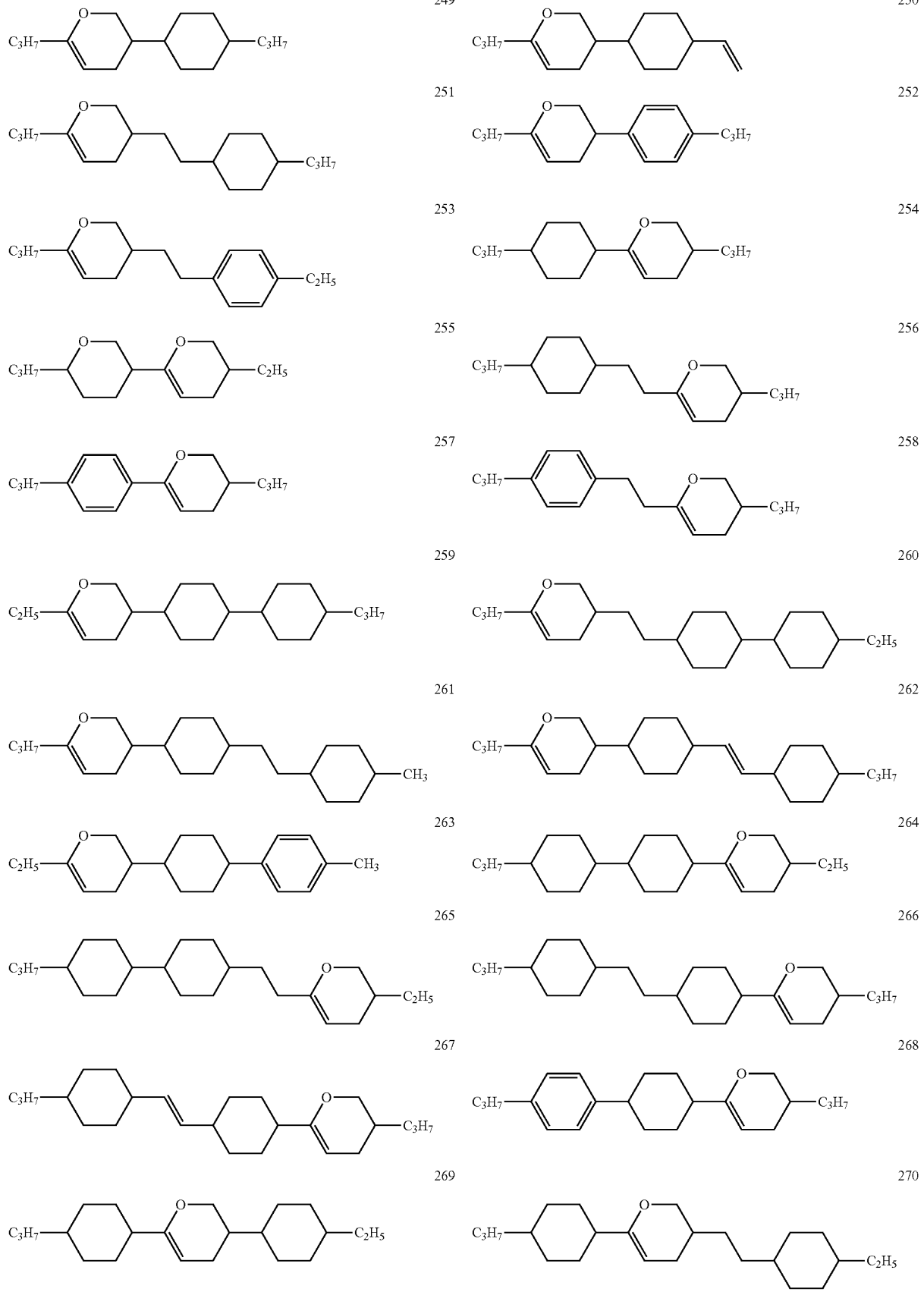

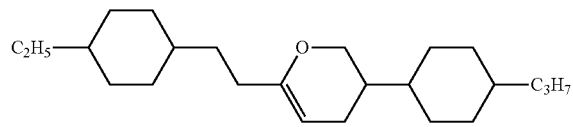

271

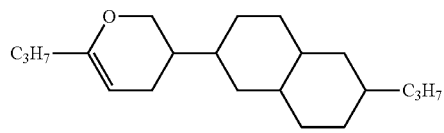

272

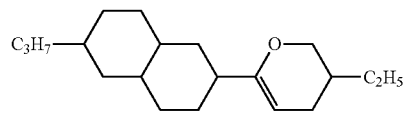

273

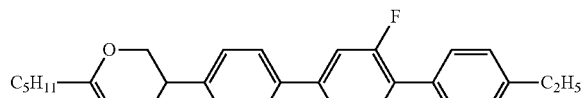

274

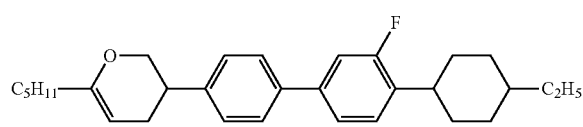

275

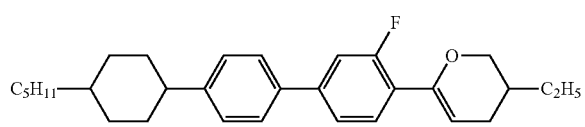

276

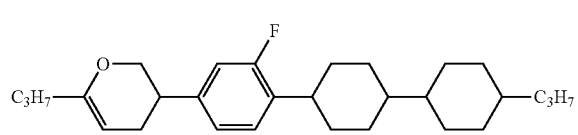

277

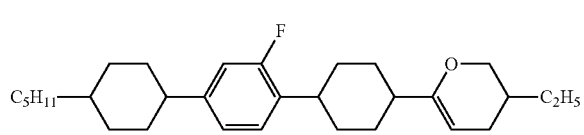

278

2. Example of Liquid Crystal Composition

Compounds in Examples were described using symbols according to definitions in Table 2 below. In Table 2, a configuration of 1,4-cyclohexylene is trans. A parenthesized number next to a symbolized compound in Examples corresponds to the number of a compound. A symbol (-) means any other liquid crystal compound. A ratio (percentage) of a liquid crystal compound is expressed in terms of weight percent (% by weight) based on the weight of the liquid crystal composition. Values of characteristics of the composition were summarized in a last part. Characteristics were measured according to the methods described above, and measured values were directly described without extrapolation.

TABLE 2

Method for Description of Compounds using Symbols
R—(A$_1$)—Z$_1$— . . . —Z$_n$—(A$_n$)—R'

| 1) Left-terminal Group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_nH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right-terminal Group —R' | Symbol |
|---|---|
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —F | —F |
| —Cl | —CL |

TABLE 2-continued

Method for Description of Compounds using Symbols
R—(A$_1$)—Z$_1$— . . . —Z$_n$—(A$_n$)—R'

| | |
|---|---|
| —$OCF_3$ | —OCF3 |
| —$OCF_2H$ | —OCF2H |
| —$CF_3$ | —CF3 |
| —CF=CH—$CF_3$ | —FVCF3 |
| —C≡N | —C |

| 3) Bonging Group —Zn— | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

| 4) Ring Structure —An— | Symbol |
|---|---|
| (cyclohexane) | H |
| (benzene) | B |
| (fluorobenzene) | B(F) |
| (difluorobenzene) | B(2F) |

TABLE 2-continued

Method for Description of Compounds using Symbols
R—(A₁)—Z₁— . . . —Zₙ—(Aₙ)—R'

| Structure | Symbol |
|---|---|
| 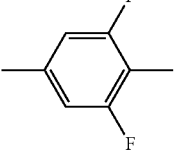 | B(F,F) |
| 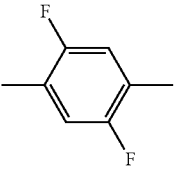 | B(2F,5F) |
| 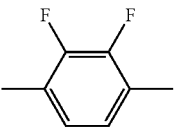 | B(2F,3F) |
| 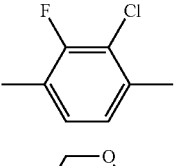 | B(2F,3CL) |
| 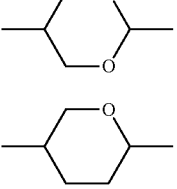 | G |
| 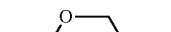 | dh |
| 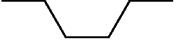 | Dh |
|  | ch |
|  | Py |
| 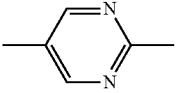 | chO |
|  | ChO |
| 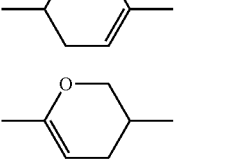 | Cro(7F,8F) |

TABLE 2-continued

Method for Description of Compounds using Symbols
R—(A₁)—Z₁— . . . —Zₙ—(Aₙ)—R'

5) Examples of Description

Example 1 3-HchOB(2F,3F)—O2

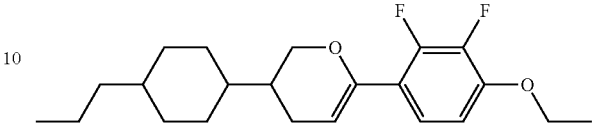

Example 2 3-HChOB(2F,3F)—O2

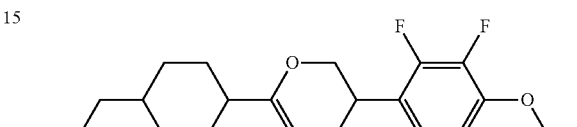

Example 3

| | | |
|---|---|---|
| 3-HchOB(2F,3F)-O2 | (No. 160) | 5% |
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 9% |
| 4-PyBB-F | (6-80) | 9% |
| 5-PyBB-F | (6-80) | 9% |
| 5-HBB(F)B-2 | (4-5) | 9% |
| 5-HBB(F)B-3 | (4-5) | 9% |

NI = 97.5° C.; Δn = 0.186; Δ∈ = 7.2; η = 40.3 mPa · s.

Example 4

| | | |
|---|---|---|
| 3-HChOB(2F,3F)-O2 | (No. 107) | 5% |
| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 3% |
| 5-HHEB-F | (6-10) | 4% |
| 2-HHB(F)-F | (6-2) | 5% |
| 3-HHB(F)-F | (6-2) | 6% |
| 5-HHB(F)-F | (6-2) | 6% |
| 3-HHB(F,F)-F | (6-3) | 5% |

Example 5

| | | |
|---|---|---|
| 3-ChOB(2F,3F)-O2 | (No. 54) | 5% |
| 5-HB-CL | (5-2) | 16% |
| 3-HH-4 | (2-1) | 12% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |

-continued

| | | |
|---|---|---|
| 4-HHB(F)-F | (6-2) | 9% |
| 5-HHB(F)-F | (6-2) | 9% |
| 7-HHB(F)-F | (6-2) | 8% |
| 5-BBB(F)-F | (6-22) | 4% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

Example 6

| | | |
|---|---|---|
| 3-chOB-2 | (No. 222) | 5% |
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 6% |
| 3-HBB(F,F)-F | (6-24) | 19% |
| 5-HBB(F,F)-F | (6-24) | 20% |
| 3-H2BB(F,F)-F | (6-27) | 9% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |

Example 7

| | | |
|---|---|---|
| 3-chOH-V | (No. 220) | 5% |
| 5-HB-F | (5-2) | 12% |
| 6-HB-F | (5-2) | 9% |
| 7-HB-F | (5-2) | 7% |
| 2-HHB-OCF3 | (6-1) | 4% |
| 3-HHB-OCF3 | (6-1) | 7% |
| 4-HHB-OCF3 | (6-1) | 5% |
| 5-HHB-OCF3 | (6-1) | 5% |
| 3-HH2B-OCF3 | (6-4) | 4% |
| 5-HH2B-OCF3 | (6-4) | 4% |
| 3-HHB(F,F)-OCF2H | (6-3) | 4% |
| 3-HHB(F,F)-OCF3 | (6-3) | 5% |
| 3-HH2B(F)-F | (6-5) | 3% |
| 3-HBB(F)-F | (6-2) | 10% |
| 5-HBB(F)-F | (6-2) | 10% |
| 5-HBBH-3 | (4-1) | 3% |
| 3-HB(F)BH-3 | (4-2) | 3% |

Example 8

| | | |
|---|---|---|
| 3-HchOB(2F,3F)-O2 | (No. 160) | 5% |
| 5-HB-CL | (5-2) | 3% |
| 7-HB(F)-F | (5-3) | 7% |
| 3-HH-4 | (2-1) | 9% |
| 3-HH-EMe | (2-2) | 21% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 5% |
| 2-H2GB(F,F)-F | (6-106) | 4% |
| 3-H2GB(F,F)-F | (6-106) | 5% |
| 5-GHB(F,F)-F | (6-109) | 5% |

NI = 83.6° C.; Δn = 0.068; Δ∈ = 4.9; η = 21.2 mPa · s.

Example 9

| | | |
|---|---|---|
| 3-HChOB(2F,3F)-O2 | (No. 160) | 5% |
| 3-HB-O1 | (2-5) | 15% |
| 3-HH-4 | (2-1) | 5% |
| 3-HB(2F,3F)-O2 | (9-1) | 12% |
| 5-HB(2F,3F)-O2 | (9-1) | 10% |
| 2-HHB(2F,3F)-1 | (10-1) | 12% |
| 3-HHB(2F,3F)-1 | (10-1) | 10% |
| 3-HHB(2F,3F)-O2 | (10-1) | 13% |
| 5-HHB(2F,3F)-O2 | (10-1) | 12% |
| 3-HHB-1 | (3-1) | 6% |

Example 10

| | | |
|---|---|---|
| 3-ChOB(2F,3F)-O2 | (No. 54) | 5% |
| 2-HH-5 | (2-1) | 3% |
| 3-HH-4 | (2-1) | 15% |
| 3-HH-5 | (2-1) | 4% |
| 3-HB-O2 | (2-5) | 12% |
| 3-H2B(2F,3F)-O2 | (9-4) | 15% |
| 5-H2B(2F,3F)-O2 | (9-4) | 10% |
| 3-HHB(2F,3CL)-O2 | (10-1) | 5% |
| 2-HBB(2F,3F)-O2 | (10-7) | 3% |
| 3-HBB(2F,3F)-O2 | (10-7) | 9% |
| 5-HBB(2F,3F)-O2 | (10-7) | 9% |
| 3-HHB-1 | (3-1) | 3% |
| 3-HHB-3 | (3-1) | 4% |
| 3-HHB-O1 | (3-1) | 3% |

Example 11

| | | |
|---|---|---|
| 3-chOB(2F,3F)-2 | (No. 2) | 5% |
| 2-HH-3 | (2-1) | 17% |
| 3-HH-4 | (2-1) | 8% |
| 1-BB-3 | (2-8) | 9% |
| 3-HB-O2 | (2-5) | 2% |
| 3-BB(2F,3F)-O2 | (9-3) | 9% |
| 5-BB(2F,3F)-O2 | (9-3) | 6% |
| 2-HH1OB(2F,3F)-O2 | (10-5) | 13% |
| 3-HH1OB(2F,3F)-O2 | (10-5) | 21% |
| 3-HHB-1 | (3-1) | 5% |
| 3-HHB-O1 | (3-1) | 3% |
| 5-B(F)BB-2 | (3-8) | 2% |

Example 12

| | | |
|---|---|---|
| 3-chOH-V | (No. 220) | 5% |
| 2-HH-3 | (2-1) | 16% |
| 7-HB-1 | (2-5) | 10% |
| 5-HB-O2 | (2-5) | 8% |
| 3-HB(2F,3F)-O2 | (9-1) | 15% |
| 5-HB(2F,3F)-O2 | (9-1) | 13% |
| 3-HHB(2F,3CL)-O2 | (10-1) | 3% |
| 4-HHB(2F,3CL)-O2 | (10-1) | 3% |
| 5-HHB(2F,3CL)-O2 | (10-1) | 2% |
| 3-HH1OCro(7F,8F)-5 | (13-6) | 5% |
| 5-HBB(F)B-2 | (4-5) | 10% |
| 5-HBB(F)B-3 | (4-5) | 10% |

Example 13

| 3-HchOB(2F,3F)-O2 | (No. 160) | 5% |
|---|---|---|
| 2-HH-3 | (2-1) | 6% |
| 3-HH-V1 | (2-1) | 10% |
| 1V2-HH-1 | (2-1) | 8% |
| 1V2-HH-3 | (2-1) | 7% |
| 3-BB(2F,3F)-O2 | (9-3) | 8% |
| 5-BB(2F,3F)-O2 | (9-3) | 4% |
| 3-H1OB(2F,3F)-O2 | (9-5) | 7% |
| 2-HH1OB(2F,3F)-O2 | (10-5) | 8% |
| 3-HH1OB(2F,3F)-O2 | (10-5) | 16% |
| 3-HDhB(2F,3F)-O2 | (10-3) | 7% |
| 3-HHB-1 | (3-1) | 3% |
| 2-BB(2F,3F)B-3 | (11-1) | 11% |

NI = 84.8° C.; Δn = 0.110; Δ∈ = −4.4; η = 22.9 mPa · s.

Example 14

| 3-HChOB(2F,3F)-O2 | (No. 107) | 3% |
|---|---|---|
| 3-ChOB(2F,3F)-O2 | (No. 54) | 4% |
| 1V2-BEB(F,F)-C | (5-9) | 6% |
| 3-HB-C | (2-5) | 15% |
| 2-BTB-1 | (2-10) | 10% |
| 5-HH-VFF | (2-1) | 28% |
| 3-HHB-1 | (3-1) | 4% |
| VFF-HHB-1 | (3-1) | 6% |
| VFF2-HHB-1 | (3-1) | 11% |
| 3-H2BTB-2 | (3-17) | 5% |
| 3-H2BTB-3 | (3-17) | 4% |
| 3-H2BTB-4 | (3-17) | 4% |

Example 15

| 3-chOB-2 | (No. 222) | 4% |
|---|---|---|
| 3-chOH-V | (No. 220) | 4% |
| 3-GB(F)B(F,F)XB(F,F)-F | (7-57) | 5% |
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 3% |
| 3-HH-V | (2-1) | 38% |
| 3-HH-V1 | (2-1) | 5% |
| 3-HHEH-5 | (3-13) | 3% |
| 3-HHB-1 | (3-1) | 4% |
| V-HHB-1 | (3-1) | 4% |
| V2-BB(F)B-1 | (3-6) | 5% |
| 1V2-BB-F | (5-1) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal composition containing a liquid crystal compound according to the invention satisfies at least one of physical properties such as a high stability to ultraviolet light and heat, a high maximum temperature of a nematic phase, a low minimum temperature of the nematic phase, a small viscosity, a suitable optical anisotropy, a large dielectric anisotropy and a suitable elastic constant, or has a suitable balance regarding at least two of the physical properties thereof. Accordingly, a liquid crystal display device including the composition can be used for a liquid crystal projector, a liquid crystal television or the like.

What is claimed is:
1. A compound represented by formula (1):

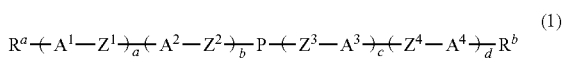

(1)

wherein, in formula (1),
$R^a$ and $R^b$ are independently alkyl having 1 to 10 carbons, and in the alkyl, at least one of —$CH_2$— may be replaced by —O—, —S—, —CO— or —$SiH_2$—, and at least one of —$CH_2CH_2$— may be replaced by —CH=CH— or —C≡C—;
ring $A^1$, $A^2$, $A^3$ and $A^4$ are independently 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one of —$CH_2$— may be replaced by —O—, —S—, —CO— or —$SiH_2$—, at least one of —$CH_2CH_2$— may be replaced by —CH=CH— or —CH=N—, and in the divalent groups, at least one of hydrogen may be replaced by fluorine, chlorine, —C≡N, —$CF_3$, —$CHF_2$, —$CH_2F$, —$OCF_3$, —$OCHF_2$ or —$OCH_2F$; and
P is a divalent group represented by formula (pr-1) or (pr-2):

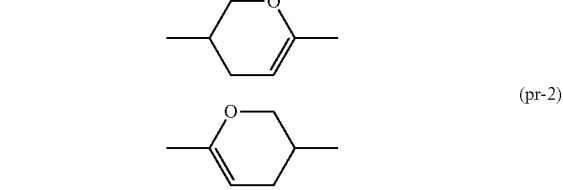

(pr-1)

(pr-2)

wherein, $Z^1$, $Z^2$, $Z^3$ and $Z^4$ are independently a single bond or alkylene having 1 to 6 carbons, and in the alkylene, at least one of —$CH_2$— may be replaced by —O—, —S—, —CO— or —$SiH_2$—, one or two of —$CH_2CH_2$— may be replaced by —CH=CH— or —C≡C—, and in the divalent groups, at least one of hydrogen may be replaced by fluorine or chlorine;
a, b, c and d are independently 0, 1 or 2, and a sum of a, b, c and d is 5 or less;
however, when P is represented by formula (pr-1), $R^a$ is alkyl, $R^b$ is alkoxy, a is 1, b is 0, c and d are 1, $A^1$ is cyclohexylene, $A^3$ and $A^4$ are 2,3-difluorophenylene, $Z^1$ and $Z^4$ are a single bond and $Z^3$ is alkylene having 2 carbons, in the alkylene, at least one of —$CH_2$— may be replaced by —O—, —S—, —CO— or —$SiH_2$—, or one of —$CH_2CH_2$— may be replaced by —CH=CH— or —C≡C—, and in the divalent groups, at least one of hydrogen may be replaced by fluorine or chlorine;
moreover, when P is represented by formula (pr-2), $R^a$ is alkoxy, $R^b$ is alkyl, a and b are 1, c is 1, d is 0, $A^1$ and $A^2$ are 2,3-difluorophenylene, $A^3$ is cyclohexylene, $Z^1$ and $Z^3$ are a single bond and $Z^2$ is alkylene having 2 carbons, in the alkylene, at least one of —$CH_2$— may be replaced by —O—, —S—, —CO— or —$SiH_2$—, or one of —$CH_2CH_2$— may be replaced by —CH=CH— or —C≡C—, and in the divalent groups, at least one of hydrogen may be replaced by fluorine or chlorine.

2. The compound according to claim 1, represented by formulas (1-1) to (1-3):

(1-1)

(1-2)

(1-3)

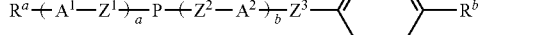

wherein, in formulas (1-1) to (1-3), $R^a$ and $R^b$ are independently hydrogen or alkyl having 1 to 10 carbons, and in the alkyl, at least one of —$CH_2$— may be replaced by —O— or —S—, and at least one of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, tetrahydro-2H-pyran-2-one-3,6-diyl, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene, 2,3-dichloro-1,4-phenylene, pyridine-2,5-diyl, pyrimidine-2,5-diyl or naphthalene-2,6-diyl, and in the divalent groups, at least one of hydrogen may be replaced by fluorine, chlorine, —$CF_3$, —$CHF_2$, —$CH_2F$, —$OCF_3$, —$OCHF_2$ or —$OCH_2F$; and P is a divalent group represented by formula (pr-1) or (pr-2):

(pr-1)

(pr-2)

wherein, $Z^1$, $Z^2$ and $Z^3$ are a single bond, —COO—, —OCO—, —$CH_2O$—, —$OCH_2$—, —$CF_2O$—, —$OCF_2$—, —$CH_2CH_2$—, —CH=CH—, —CF=CH—, —CH=CF—, —CF=CF—, —C≡C—, —$CH_2CO$—, —$COCH_2$—, —$CH_2SiH_2$—, —$SiH_2CH_2$—, —$(CH_2)_4$—, —$(CH_2)_2COO$—, —$(CH_2)_2OCO$—, —$OCO(CH_2)_2$—, —$COO(CH_2)_2$—, —$(CH_2)_2CF_2O$—, —$(CH_2)_2OCF_2$—, —$OCF_2(CH_2)_2$—, —$CF_2O(CH_2)_2$—, —$(CH_2)_3O$— or —$O(CH_2)_3$—;

$Y^1$, $Y^2$ and $Y^3$ are independently hydrogen, fluorine, chlorine, —$CF_3$, —$CHF_2$, —$CH_2F$, —$OCF_3$, —$OCHF_2$ or —$OCH_2F$; and a and b are independently 0, 1, 2 or 3, and a sum of a and b is 4 or less; and in formula (1-1), when $R^a$ is alkyl, $R^b$ is alkoxy, a and b are 1, $A^1$ is cyclohexylene, $A^2$ is 2,3-difluorophenylene, $Z^1$ and $Z^3$ are a single bond, $Z^2$ is —$CH_2CH_2$— and $Y^1$ and $Y^2$ are fluorine, P is a divalent group represented by formula (pr-2).

3. The compound according to claim 2, represented by any one of formulas (1-11a) to (1-13a) and formulas (1-11b) to (1-13b):

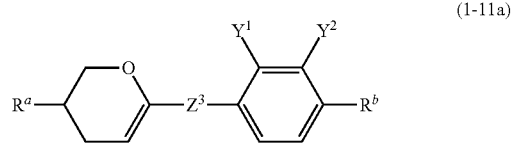

(1-11a)

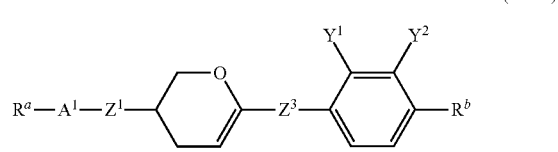

(1-12a)

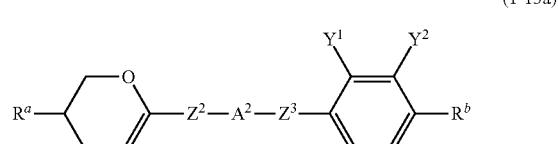

(1-13a)

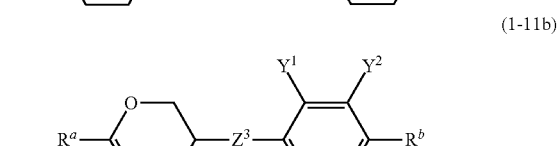

(1-11b)

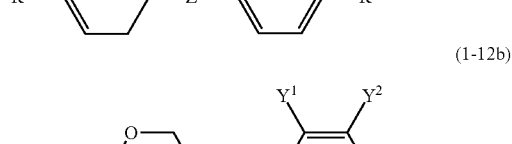

(1-12b)

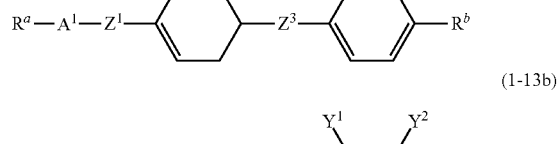

(1-13b)

wherein, in formulas (1-11a) to (1-13a) and formulas (1-11b) to (1-13b), $R^a$ and $R^b$ are independently alkyl having 1 to 10 carbons, and in the alkyl, one or two of —$CH_2$— may be replaced by —O— or —S—, and one or two of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene, pyridine-2,5-diyl, pyrimidine-2,5-diyl or naphthalene-2,6-diyl;

$Z^1$, $Z^2$ and $Z^3$ are independently a single bond, —$CH_2CH_2$—, —COO—, —OCO—, —$CH_2O$—, —$OCH_2$—, —$CF_2O$—, —$OCF_2$—, —CH=CH—, —CF=CH—, —CH=CF—, —CF=CF—, —C≡C—, —$(CH_2)_4$—, —$(CH_2)_2COO$—, —OCO$(CH_2)_2$—, —$(CH_2)_2CF_2O$—, —$OCF_2(CH_2)_2$—, —$(CH_2)_3O$— or —$O(CH_2)_3$—; and $Y^1$ and $Y^2$ are independently fluorine or chlorine.

4. The compound according to claim 3, wherein, in formulas (1-11a) to (1-13a) and formulas (1-11b) to (1-13b), $R^a$ and $R^b$ are independently alkyl having 1 to 10 carbons, alkenyl having 2 to 10 carbons or alkoxy having 1 to 9 carbons;

ring $A^1$ and $A^2$ are independently 1,4-cyclohexylene, tetrahydropyran-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene or pyrimidine-2,5-diyl;

$Z^1$, $Z^2$ and $Z^3$ are independently a single bond, —$CH_2CH_2$—, —COO—, —OCO—, —$CH_2O$—, —$OCH_2$—, —$CF_2O$—, —$OCF_2$—, —CH=CH—, —CF=CF—, —C≡C— or —$(CH_2)_4$—; and $Y^1$ and $Y^2$ are independently fluorine or chlorine.

5. The compound according to claim 2, represented by any one of formulas (1-21a) to (1-23a) and formulas (1-21b) to (1-23b):

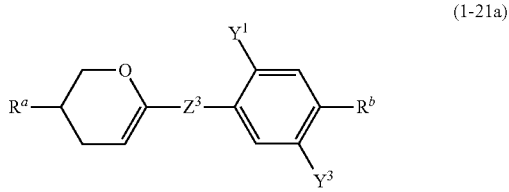
(1-21a)

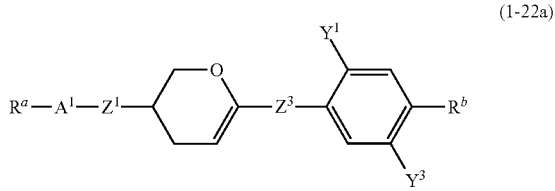
(1-22a)

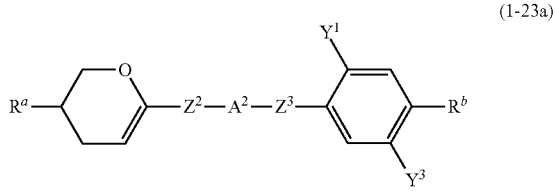
(1-23a)

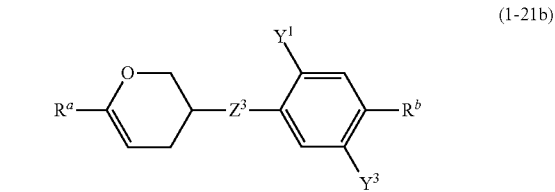
(1-21b)

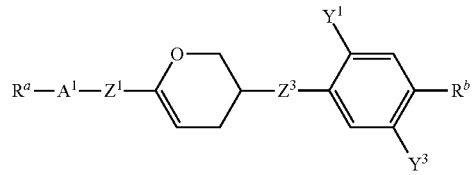
(1-22b)

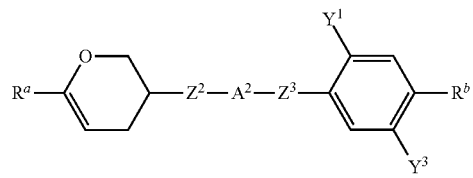
(1-23b)

wherein, in formulas (1-21a) to (1-23a) and formulas (1-21b) to (1-23b), $R^a$ and $R^b$ are independently alkyl having 1 to 10 carbons, and in the alkyl, one or two of —$CH_2$— may be replaced by —O— or —S—, and one or two of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, pyridine-2,5-diyl, pyrimidine-2,5-diyl or naphthalene-2,6-diyl;

$Z^1$, $Z^2$ and $Z^3$ are independently a single bond, —$CH_2CH_2$—, —COO—, —OCO—, —$CH_2O$—, —$OCH_2$—, —$CF_2O$—, —$OCF_2$—, —CH=CH—, —CF=CH—, —CH=CF—, —CF=CF—, —C≡C—, —$(CH_2)_4$—, —$(CH_2)_2COO$—, —OCO$(CH_2)_2$—, —$(CH_2)_2CF_2O$—, —$OCF_2(CH_2)_2$—, —$(CH_2)_3O$— or —$O(CH_2)_3$—; and $Y^1$ and $Y^3$ are independently hydrogen, fluorine or chlorine.

6. The compound according to claim 5, wherein, in formulas (1-21a) to (1-23a) and formulas (1-21b) to (1-23b), $R^a$ and $R^b$ are independently alkyl having 1 to 10 carbons, alkenyl having 2 to 10 carbons or alkoxy having 1 to 9 carbons;

ring $A^1$ and $A^2$ are independently 1,4-cyclohexylene, tetrahydropyran-2,5-diyl, 1,4-phenylene, 2-fluoro-1,4-phenylene, 2,5-difluoro-1,4-phenylene, 2,6-difluoro-1,4-phenylene, 2-chloro-1,4-phenylene or pyrimidine-2,5-diyl;

$Z^1$, $Z^2$ and $Z^3$ are independently a single bond, —$CH_2CH_2$—, —COO—, —OCO—, —$CH_2O$—, —$OCH_2$—, —$CF_2O$—, —$OCF_2$—, —CH=CH—, —CF=CF—, —C≡C— or —$(CH_2)_4$—; and $Y^1$ and $Y^3$ are independently hydrogen or fluorine.

7. The compound according to claim 2, represented by any one of formulas (1-31) to (1-36):

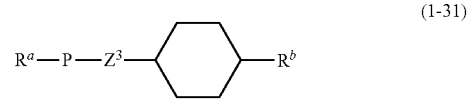
(1-31)

(1-32)
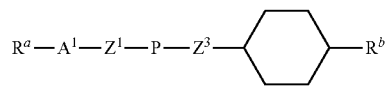

(1-33)
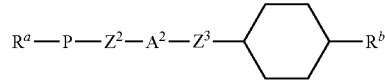

(1-34)
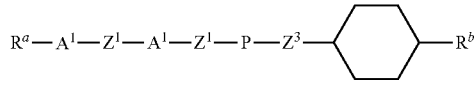

(1-35)
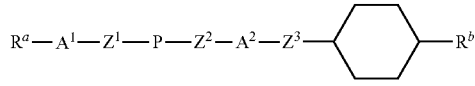

(1-36)
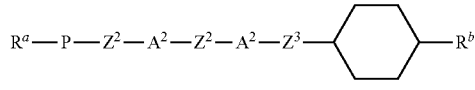

wherein, in formulas (1-31) to (1-36), $R^a$ and $R^b$ are independently alkyl having 1 to 10 carbons, and in the alkyl, one or two of —$CH_2$— may be replaced by —O— or —S—, and one or two of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-fluoro-3-chloro-1,4-phenylene, pyridine-2,5-diyl, pyrimidine-2,5-diyl or naphthalene-2,6-diyl; and P is a divalent group represented by formula (pr-1) or (pr-2):

(pr-1)
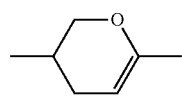

(pr-2)
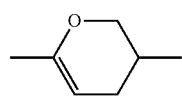

wherein, $Z^1$, $Z^2$ and $Z^3$ are independently a single bond, —$CH_2CH_2$—, —COO—, —OCO—, —$CH_2O$—, —$OCH_2$—, —$CF_2O$—, —$OCF_2$—, —CH=CH—, —CF=CH—, —CH=CF—, —CF=CF—, —C≡C—, —$(CH_2)_4$—, —$(CH_2)_2COO$—, —$OCO(CH_2)_2$—, —$(CH_2)_2CF_2O$—, —$OCF_2(CH_2)_2$—, —$(CH_2)_3O$— or —$O(CH_2)_3$—.

8. The compound according to claim 2, represented by any one of formulas (1-14) to (1-16) and formulas (1-24) to (1-26):

(1-14)
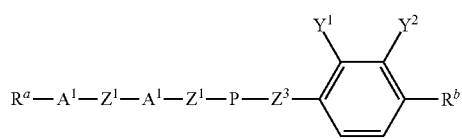

(1-15)
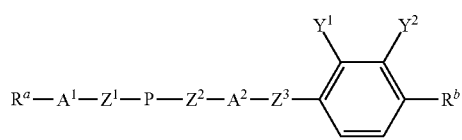

(1-16)
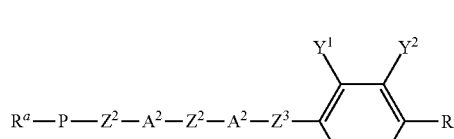

(1-24)
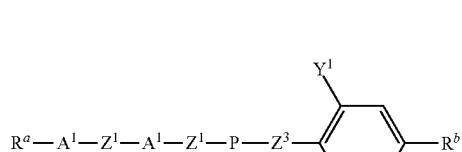

(1-25)

(1-26)
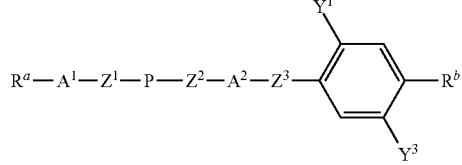

wherein, in formulas (1-14) to (1-16) and formulas (1-24) to (1-26), $R^a$ and $R^b$ are independently alkyl having 1 to 10 carbons, and in the alkyl, one or two of —$CH_2$— may be replaced by —O— or —S—, and one or two of —$CH_2CH_2$— may be replaced by —CH=CH— or —C≡C—;

ring $A^1$ and $A^2$ are independently 1,4-cyclohexylene, 1,4-cyclohexene-1,4-diyl, tetrahydropyran-2,5-diyl, decahydronaphthalene-2,6-diyl, 1,2,3,4-tetrahydronaphthalene-2,6-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, pyridine-2,5-diyl, pyrimidine-2,5-diyl or naphthalene-2,6-diyl; and P is a divalent group represented by formula (pr-1) or (pr-2):

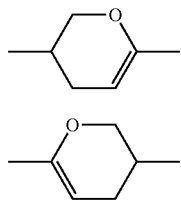
(pr-1)

(pr-2)

wherein, $Z^1$, $Z^2$ and $Z^3$ are independently a single bond, —CH$_2$CH$_2$—, —COO—, —OCO—, —CH$_2$O—, —OCH$_2$—, —CF$_2$O—, —OCF$_2$—, —CH=CH—, —CF=CH—, —CH=CF—, —CF=CF—, —C≡C—, —(CH$_2$)$_4$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O— or —O(CH$_2$)$_3$—; and in formulas (1-14) to (1-16), $Y^1$ and $Y^2$ are independently fluorine or chlorine, and in formulas (1-24) to (1-26), $Y^1$ and $Y^3$ are independently hydrogen, fluorine or chlorine.

9. The compound according to claim 8, wherein, in formulas (1-14) to (1-16) and formulas (1-24) to (1-26) according to claim 8, R$^a$ and R$^b$ are independently alkyl having 1 to 10 carbons, alkenyl having 2 to 10 carbons or alkoxy having 1 to 9 carbons;

ring A$^1$ and A$^2$ are independently 1,4-cyclohexylene, tetrahydropyran-2,5-diyl, 1,4-phenylene, 2-fluoro-1,4-phenylene, 2,5-difluoro-1,4-phenylene, 2,6-difluoro-1,4-phenylene, 2-chloro-1,4-phenylene or pyrimidine-2,5-diyl;

$Z^1$, $Z^2$ and $Z^3$ are independently a single bond, —CH$_2$CH$_2$—, —COO—, —OCO—, —CH$_2$O—, —OCH$_2$—, —CF$_2$O—, —OCF$_2$—, —CH=CH—, —CF=CF—, —C≡C— or —(CH$_2$)$_4$—; and $Y^1$ and $Y^2$ are independently hydrogen or fluorine.

10. The compound according to claim 2, represented by any one of formula (1-111a), formula (1-121a), formula (1-131a), formula (1-141a), formula (1-151a), formula (1-161a), formula (1-111b), formula (1-121b), formula (1-131b), formula (1-141b), formula (1-151b) and formula (1-161b):

(1-111a)
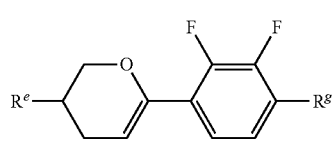

(1-111b)
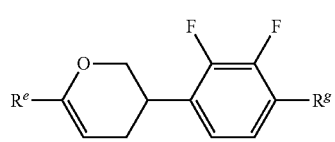

(1-121a)
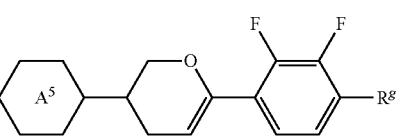

(1-121b)
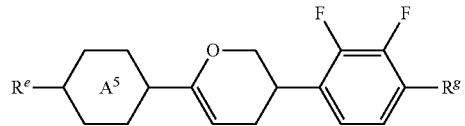

(1-131a)
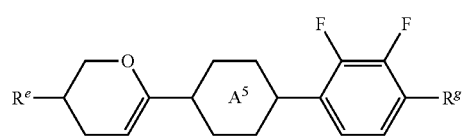

(1-131b)
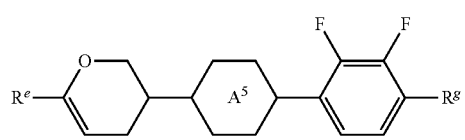

(1-141a)
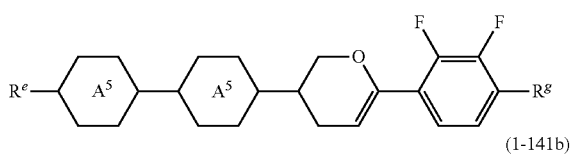

(1-141b)
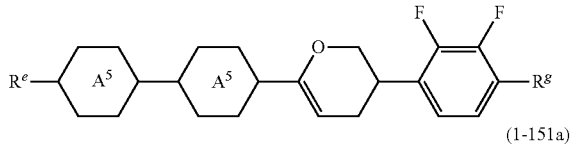

(1-151a)
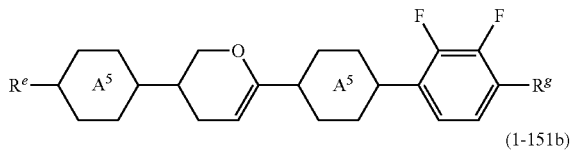

(1-151b)
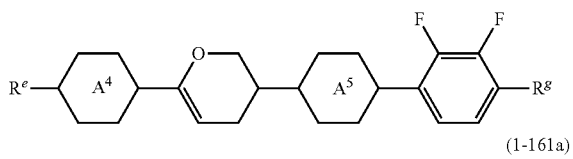

(1-161a)
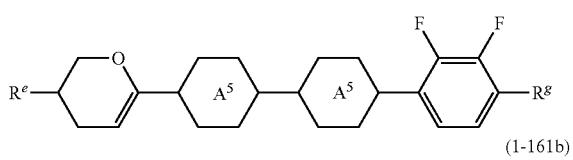

(1-161b)

wherein, in formula (1-111a), formula (1-121a), formula (1-131a), formula (1-141a), formula (1-151a), formula (1-161a), formula (1-111b), formula (1-121b), formula (1-131b), formula (1-141b), formula (1-151b) and formula (1-161b), R$^e$ and R$^g$ are independently alkyl having 1 to 10 carbons, alkenyl having 2 to 10 carbons or alkoxy having 1 to 9 carbons; and ring A$^5$ is 1,4-cyclohexylene, 1,4-phenylene, 2-fluoro-1,4-phenylene or 2,3-difluoro-1,4-phenylene.

11. The compound according to claim 2, represented by any one of formula (1-211a), formula (1-212a), formula (1-213a), formula (1-231a), formula (1-311a), formula (1-331a), formula (1-361a), formula (1-211b), formula (1-212b), formula (1-213b), formula (1-231b), formula (1-311b), formula (1-331b) and formula (1-361b):

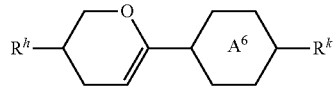
(1-211a)

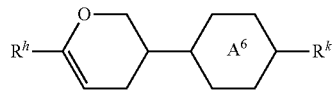
(1-211b)

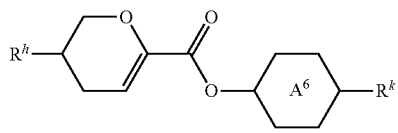
(1-212a)

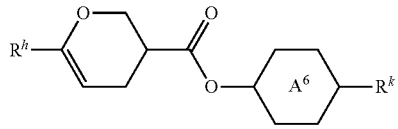
(1-212b)

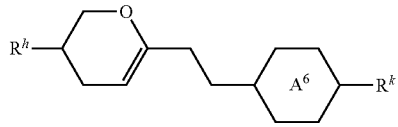
(1-213a)

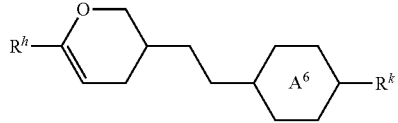
(1-213b)

(1-231a)

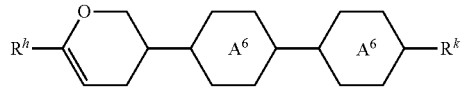
(1-231b)

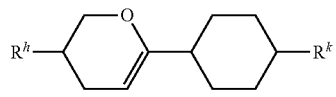
(1-311a)

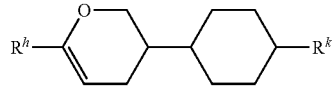
(1-311b)

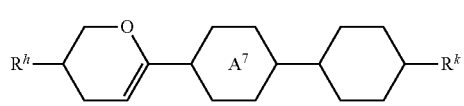
(1-331a)

(1-331b)

-continued

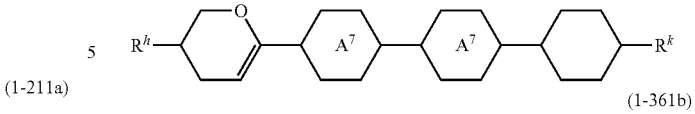
(1-361a)

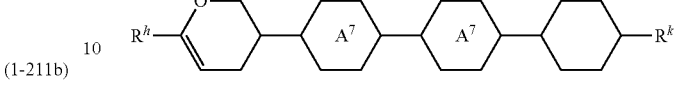
(1-361b)

wherein, $R^h$ and $R^k$ are independently alkyl having 1 to 10 carbons, alkenyl having 2 to 10 carbons or alkoxy having 1 to 9 carbons; and
ring $A^6$ is 1,4-cyclohexylene, 1,4-phenylene or 2-fluoro-1,4-phenylene; and ring $A^7$ is 1,4-phenylene or 2-fluoro-1,4-phenylene.

12. A liquid crystal composition, containing the compound according to claim 2.

13. A liquid crystal composition having a nematic phase and containing at least one compound selected from the group of compounds represented by formula (1) as a first component and at least one compound selected from the group of compounds represented by formulas (2) to (4) as a second component:

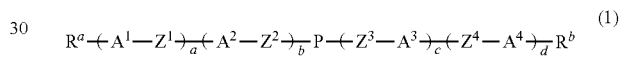
(1)

wherein, in formula (1),
$R^a$ and $R^h$ are independently alkyl having 1 to 10 carbons, and in the alkyl, at least one of —$CH_2$— may be replaced by —O—, —S—, —CO— or —$SiH_2$—, and at least one of —$CH_2CH_2$— may be replaced by —CH=CH— or —C≡C—;
ring $A^1$, $A^2$, $A^3$ and $A^4$ independently 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one of —$CH_2$— may be replaced by —O—, —S—, —CO— or —$SiH_2$—, at least one of —$CH_2CH_2$— may be replaced by —CH=CH— or —CH=N—, and in the divalent groups, at least one of hydrogen may be replaced by fluorine, chlorine, —C≡N, —$CF_3$, —$CHF_2$, —$CH_2F$, —$OCF_3$, —$OCHF_2$ or —$OCH_2F$; and
P is a divalent group represented by formula (pr-1) or (pr-2):

(pr-1)

(pr-2)

wherein, $Z^1$, $Z^2$, $Z^3$ and $Z^4$ are independently a single bond or alkylene having 1 to 6 carbons, and in the alkylene, at least one of —CH$_2$— may be replaced by —O—, —S—, —CO— or —SiH$_2$—, one or two of —CH$_2$CH$_2$— may be replaced by —CH=CH— or —C≡C—, and in the divalent groups, at least one of hydrogen may be replaced by fluorine or chlorine; and a, b, c and d are independently 0, 1 or 2, and a sum of a, b, c and d is 5 or less;

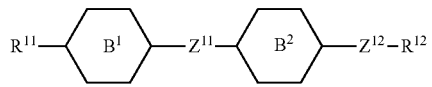
(2)

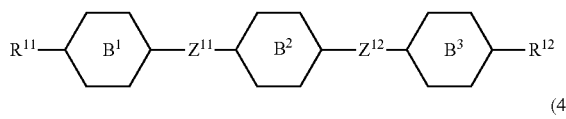
(3)

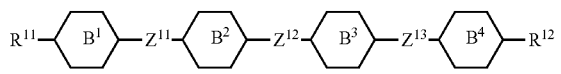
(4)

wherein, in formulas (2) to (4),
R$^{11}$ and R$^{12}$ are independently alkyl having 1 to 10 carbons or alkenyl having 2 to 10 carbons, and in the alkyl or the alkenyl, at least one of —CH$_2$— may be replaced by —O—, and at least one of hydrogen may be replaced by fluorine;
ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and
Z$^{11}$, Z$^{12}$ and Z$^{13}$ are independently a single bond, —CH$_2$CH$_2$—, —CH=CH—, —C≡C— or —COO—.

14. The liquid crystal composition according to claim 13, further containing at least one compound selected from the group of compounds represented by formulas (5) to (7) as a third component:

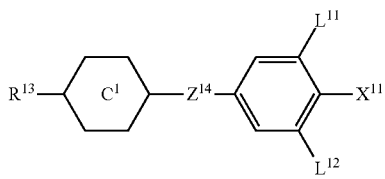
(5)

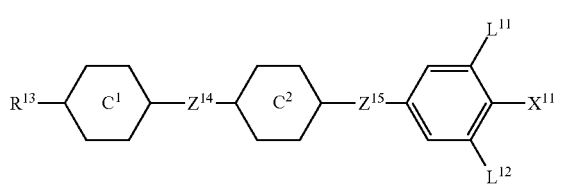
(6)

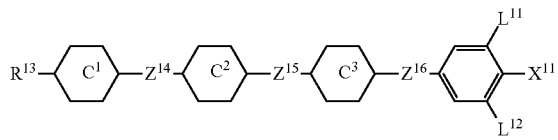
(7)

wherein, in formulas (5) to (7),
R$^{13}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;
X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring C$^1$, ring C$^2$ and ring C$^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
Z$^{14}$, Z$^{15}$ and Z$^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and
L$^{11}$ and L$^{12}$ are independently hydrogen or fluorine.

15. The liquid crystal composition according to claim 13, further containing at least one compound selected from the group of compounds represented by formula (8) as the third component:

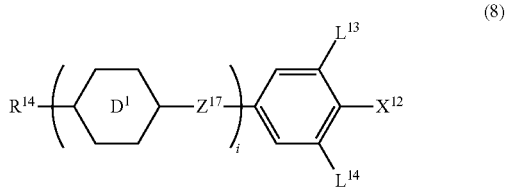
(8)

wherein, in formula (8),
R$^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;
X$^{12}$ is —C≡N or —C≡C—C≡N;
ring D$^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
Z$^{17}$ is a single bond, —CH$_2$CH$_2$—, —COO—, —CF$_2$O—, —OCF$_2$— or —CH$_2$O—;
L$^{13}$ and L$^{14}$ are independently hydrogen or fluorine; and
i is 1, 2, 3 or 4.

16. The liquid crystal composition according to claim 13, further containing at least one compound selected from the group of compounds represented by formulas (9) to (15) as the third component:

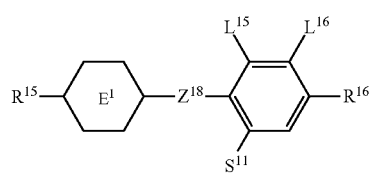
(9)

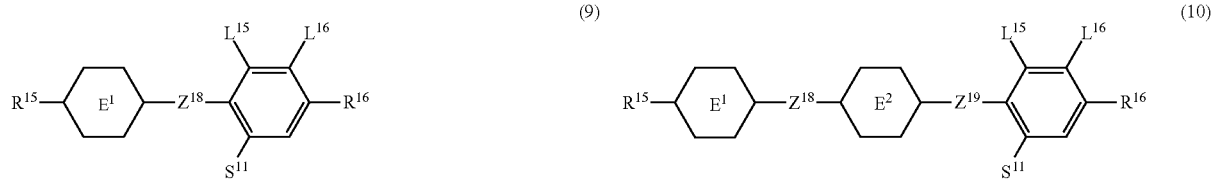
(10)

-continued

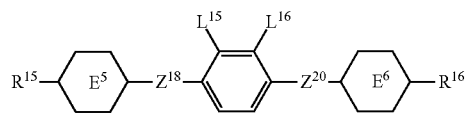 (11)

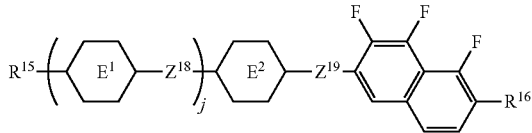 (12)

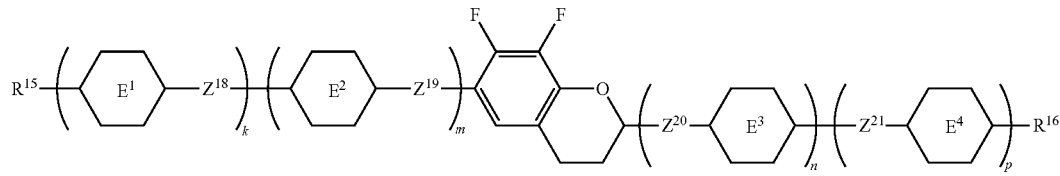 (13)

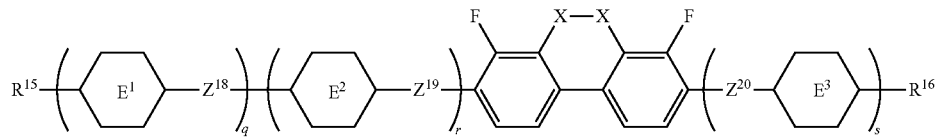 (14)

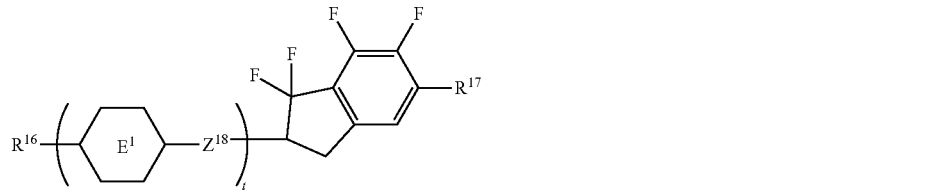 (15)

wherein, in formulas (9) to (15), $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$R^{17}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

17. A liquid crystal display device, including the liquid crystal composition according to claim 12.

* * * * *